(12) United States Patent
Follmann et al.

(10) Patent No.: US 9,023,849 B2
(45) Date of Patent: May 5, 2015

(54) SUBSTITUTED FUSED IMIDAZOLES AND PYRAZOLES AND USE THEREOF

(71) Applicant: Bayer Intellectual Property GmbH, Monheim (DE)

(72) Inventors: Markus Follmann, Köln (DE); Johannes-Peter Stasch, Solingen (DE); Gorden Redlich, Bochum (DE); Nils Griebenow, Dormagen (DE); Dieter Lang, Velbert (DE); Frank Wunder, Wuppertal (DE); Holger Paulsen, Hilden (DE); Walter Hübsch, Wuppertal (DE); Alexandros Vakalopoulos, Hilden (DE); Adrian Tersteegen, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/736,692

(22) Filed: Jan. 8, 2013

(65) Prior Publication Data

US 2013/0210824 A1 Aug. 15, 2013

(30) Foreign Application Priority Data

Jan. 11, 2012 (DE) .......................... 10 2012 200 352

(51) Int. Cl.
| | | |
|---|---|---|
| *A61K 31/5365* | (2006.01) | |
| *C07D 253/00* | (2006.01) | |
| *C07D 487/04* | (2006.01) | |
| *C07D 519/00* | (2006.01) | |
| *A61K 31/519* | (2006.01) | |
| *A61K 31/53* | (2006.01) | |
| *A61K 45/06* | (2006.01) | |

(52) U.S. Cl.
CPC ............ *C07D 487/04* (2013.01); *C07D 519/00* (2013.01); *A61K 31/519* (2013.01); *A61K 31/53* (2013.01); *A61K 45/06* (2013.01)

(58) Field of Classification Search
CPC .......................... C07D 253/00; A61K 31/5365
USPC .................................. 544/180, 215; 514/241
See application file for complete search history.

(56) References Cited

U.S. PATENT DOCUMENTS

| | | | |
|---|---|---|---|
| 5,976,523 A | 11/1999 | Awaya et al. | |
| 6,180,656 B1 | 1/2001 | Furstner et al. | |
| 6,451,805 B1 | 9/2002 | Straub et al. | |
| 6,743,798 B1 | 6/2004 | Straub et al. | |
| 6,833,364 B1 | 12/2004 | Straub et al. | |
| 6,903,089 B1 | 6/2005 | Stasch et al. | |
| 7,173,037 B2 | 2/2007 | Alonso-Alija et al. | |
| 7,410,973 B2 | 8/2008 | Fuerer et al. | |
| 7,414,136 B2 | 8/2008 | Matsumura et al. | |
| 8,242,272 B2 | 8/2012 | Jimenez et al. | |
| 8,309,551 B2 | 11/2012 | Schirok et al. | |
| 8,420,656 B2 * | 4/2013 | Follmann et al. ............. 514/256 |
| 8,765,769 B2 | 7/2014 | Follmann et al. | |
| 8,859,569 B2 | 10/2014 | Follmann et al. | |
| 2004/0235863 A1 | 11/2004 | Feurer et al. | |
| 2011/0218202 A1 | 9/2011 | Brockunier et al. | |
| 2011/0224197 A1 | 9/2011 | Henkel et al. | |
| 2013/0072492 A1 | 3/2013 | Raghavan et al. | |
| 2013/0172372 A1 | 7/2013 | Follmann et al. | |
| 2013/0178475 A1 | 7/2013 | Moore et al. | |
| 2013/0338137 A1 | 12/2013 | Follmann et al. | |

FOREIGN PATENT DOCUMENTS

| | | |
|---|---|---|
| CA | 2804470 | 1/2012 |
| CA | 2809911 | 3/2012 |
| CA | 2833698 | 10/2012 |
| CA | 2834901 | 11/2012 |
| CA | 2840886 | 1/2013 |
| CN | 1613849 | 5/2005 |
| EP | 0634413 | 1/1995 |
| WO | 01083490 | 11/2001 |

OTHER PUBLICATIONS

Banholzer et a;,"Zum Mechanisums der thermischen Decarbonylierung von Oxalessigestern," Helv. Chim. Acta., 1959, 42: 2584-2597.

Cheng et al.,"Potential Purine Antagonists VII. Synthesis of 6-Alkylpyrazolo-[3,4-d]pyrimidines," J. Org. Chem., 1958, 23:191-200.

Evgenov et al.,"NO-independent stimulators and activators of soluble guanylate cyclase: discovery and therapeutic potential," Nat. Rev. Drug. Disc, Sep. 2006, 5:543-547.

Goldberg et al., "Stimulation of Human Platelet Guanylate Cyclase by Fatty Acids," J. Biol. Chem., 1977, 252, 1279-1285.

Greene et al.,"The Role of Protective Groups in Organic Synthesis," Greene's Protective Groups in Organic Synthesis, 2007, Fourth Edition, 1-15.

Hassan et al.,"Aryl-Aryl Bond Formation One Century after the Discovery of the Ullmann Reaction," Chem. Rev. 2002, 102: 1359-1469.

Herdemann et al.,"Identification of potent ITK inhibitors through focused compound library design including structural Information," Bioorganic & Medicinal Chemistry Letters, 2010, 20: 6998-7003.

Ko et al., "YC-1, a Novel Activator of Platelet Guanylate Cyclase," Blood, Dec. 1994, 84(12): 4226-4233.

Maarten van den Buuse,"Circadian Rythyms of Blood Pressure, Heart Rate, and Locomotor Activity in Spontaneously Hypertensive Rats as Measured with Radio-Telemetry," Physiology & Behavior, 1994, 55(4):783-787.

(Continued)

*Primary Examiner* — Golam M M Shameem

(74) *Attorney, Agent, or Firm* — Buchanan Ingersoll & Rooney PC

(57) ABSTRACT

The present application relates to novel substituted fused imidazoles and pyrazoles, to processes for preparation thereof, to the use thereof, alone or in combinations, for treatment and/or prophylaxis of diseases and to the use thereof producing medicaments for the treatment and/or prophylaxis of diseases, especially for treatment and/or prophylaxis of cardiovascular disorders.

7 Claims, No Drawings

(56) References Cited

OTHER PUBLICATIONS

Mittendorf et al., "Discovery of Riociguat (BAY 63/2521): A Potent, Oral Stimulator of Soluble Guanylate Cyclase for the Treatment of Pulmonary Hypertension," Chem. Med. Chem., 2009, 4: 853-865.
Malsch et al., "Effect of YC-1, an NO-independent, superoxide-sensitive stimulator of soluble guanylyl cyclase, on smooth muscle responsiveness to nitrovasodilators," But J. Pharm., 1997, 120: 681-689.
Pettibone et al., "A Structurally Novel Stimulator of Guanylate Cyclase with Long-Lasting Hypotensive Activity in the Dog," Euro. J. of Pharmacology, 1985, 116: 307-312.
Robins, Roland K., "Potential Purine Antagonists. I. Synthesis of Some 4,6-Substituted Pyrazolo [3,4-d] pyrimidines," J. Am. Chem. Soc., 1956, 78: 784-790.
Rocaboy et al.,"Syntheses and Reactivities of Disubstituted and Trisubstituted Fluorous Pyridines with High Fluorous Phase Affinities: Solid State, Liquid Crystal, and Ionic Liquid-Phase Properties," J. Org. Chem, 2002, 67(20): 6836-6870.
Sharkovska et al.,"Nitric oxide-independent stimulation of soluble guanylate cyclase reduces organ damage in experimental low-renin and high-renin models," J. Hypertnesion, 2010, 28(8):1666-1675.
Stasch et al.,"Soluble Guanylate Cyclase as an Emerging Therapeutic Target in Cardiopulmonary Disease," Circulation, May 2011, 123: 2263-2273.
Wilson et al.,"Development of a Scaleable Synthesis of a Partial Nicotinic Acid Receptor Agonist," Organic Process Research & Development, 2009, 13: 543-547.
Winn et al., "2-(Alkylamino)nicotinic Acid and Analogs. Potent Angiotensin II Antagonists," J. Med. Chem 1993, 36: 2676-2688.
Witte et al.,"Experimental heart failure in rats: effects on cardiovascular circadian rhythms and on myocardial β-adrenergic signaling," Cardiovascular Research, 2000, 47: 350-358.
Becker et al.,"NO-Independent Regulatory Site of Direct sGC Stimulators like YC-1 and BAY 41/2272," BMC Pharmacology, 2001, 1: 13.
Wunder et al., "A cell-based cGMP assay useful for ultra-high-throughput screening and identification of modulators of the nitric oxide/cGMP pathway," Anal. Biochem., 2005, 339:104-112.
Yu et al., "Vasorelaxant Effect of Isoliquiritigenin, A novel soluble guanylate cyclase activator, in rat aorta," Brit. J. of Pharmacology, 1995, 114: 1587-1594.
Wu et al., "YC-1 inhibited human platelet aggregation through NO-independent activation of soluble guanylate cyclase," Br J. Pharmacol. Oct. 1995, 116(3):1973-1978.
Evgenov et al.,"NO-independent stimulators and activators of soluble guanylate cyclase: discovery and therapeutic potential," Nat. Rev. Drug. Disc, Sep. 2006, 5:755-768.
Badesch et al., "Prostanoid Therapy for Pulmonary Arterial Hypertension," Journal of the American College of Cardiology, Jun. 16, 2004, 43:56S-61S.
Ghofrani et al., "Soluble guanylate cyclase stimulation: an emerging option in pulmonary hypertension therapy," Eur. Respir. Rev., 2009, 18(111):35-41.
Kelley et al., "Synthesis and Anticonvulsant Activity of N-Benzylpyrrolo[2,3-d]-, -pyrazolo[3,4-d]-, and -triazolo[4,5-d] pyrimidines: Imidazole Ring-Modified Analogues of 9-(2-Fluorobenzyl) -6- (methylamino)-9H-purine," J. Med. Chem, 1995, 38:3884-3888.
Oudot et al., "Combination of BAY 60/4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, 2011, 60:1020-1026.
Straub et al., "NO-Independent Stimulators of Soluble Guanylate Cyclase," Bioorg. Med. Chem. Lett., 2001, 11:781-784.
Toche et al., "Synthesis of Pyrazolopyridine 3-Carboxylates by Friedlander Condensation," J. Heterocyclic Chem., 2010, 47:287.
Wunder et al., "Characterization of the First Potent and Selective PDE9 Inhibitor Using a cGMP Reporter Cell Line," Molecular Pharmacology 2005, vol. 68, No. 6, 1775 - 1781.
U.S. Appl. No. 13/704,980, 371(c) date Feb. 28, 2013, published as 20130172372.
U.S. Appl. No. 14/194,224, filed Feb. 28, 2014.
U.S. Appl. No. 14/371,054, filed Jan. 8, 2013.
U.S. Appl. No. 14/371,046, filed Jul. 8, 2014.
U.S. Appl. No. 13/806,425, filed Mar. 7, 2013.

* cited by examiner

SUBSTITUTED FUSED IMIDAZOLES AND PYRAZOLES AND USE THEREOF

The present application relates to novel substituted fused imidazoles and pyrazoles, to processes for preparation thereof, to the use thereof, alone or in combinations, for treatment and/or prophylaxis of diseases and to the use thereof for production of medicaments for treatment and/or prophylaxis of diseases, especially for treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. This is of central importance for the activation mechanism. NO is able to bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

Through the formation of cGMP and the resulting regulation of phosphodiesterases, ion channels and protein kinases, guanylate cyclase plays a crucial role in different physiological processes, more particularly in the relaxation and proliferation of smooth muscle cells, in platelet aggregation and platelet adhesion, and in neuronal signal transmission, and also in the event of disorders based on disruption of the abovementioned processes. Under pathophysiological conditions, the NO/cGMP system can be suppressed, which can lead, for example, to hypertension, platelet activation, increased cell proliferation, endothelial dysfunction, atherosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Therapeutic stimulation of soluble guanylate cyclase has to date been accomplished using exclusively compounds such as organic nitrates, the effect of which is based on NO. This is formed by bioconversion and activates soluble guanylate cyclase by attack at the central iron atom of haem. In addition to the side effects, the development of tolerance is one of the crucial disadvantages of this mode of treatment.

A few years ago, some substances which stimulate soluble guanylate cyclase directly, i.e. without prior release of NO, were described, for example 3-(5'-hydroxymethyl-2'-furyl)-1-benzylindazole [YC-1; Wu et al., *Blood* 84 (1994), 4226; Mülsch et al., *Brit. J. Pharmacol.* 120 (1997), 681]. The more recent stimulators of soluble guanylate cyclase include BAY 41-2272, BAY 41-8543 and riociguat (BAY 63-2521) (see, for example, Stasch J.-P. et al., *Nat. Rev. Drug Disc.* 2006; 5: 755-768; Stasch J.-P. et al., *Chem Med Chem* 2009; 4: 853-865. Stasch J.-P. et al., *Circulation* 2011; 123: 2263-2273). Interestingly, some of these sGC stimulators, for example YC-1 or BAY 41-2272, also exhibit PDE5-inhibitory action in addition to direct guanylate cyclase stimulation. In order to maximize the cGMP pathway, it is pharmacologically desirable to stimulate the synthesis of cGMP and simultaneously to inhibit degradation via PDE-5. This dual principle is particularly advantageous in pharmacological terms (see, for example, Oudout et al., Eur. Urol. 2011, 60, 1020-1026.).

The dual principle is fulfilled in the context of the present invention when the inventive compounds exhibit an effect on recombinant guanylate cyclase reporter cell lines according to the study in B-2 as the minimal effective concentration (MEC) of $\leq 3$ μM and exhibit inhibition of human phosphodiesterase 5 (PDE5) according to the study in B-6 as $IC_{50}>100$ nM.

Phosphodiesterase-5 (PDE5) is the name of one of the enzymes which cleave the phosphoric ester bond in cGMP, forming 5'-guanosine monophosphate (5'-GMP). In humans, phosphodiesterase-5 occurs predominantly in the smooth musculature of the corpus cavernosum penis and the pulmonary arteries. Blockage of cGMP degradation by inhibition of PDE5 (with, for example, sildenafil, vardenafil or tadalafil) leads to increased signals of the relaxation signalling pathways and specifically to increased blood supply in the corpus cavernosum penis and lower pressure in the pulmonary blood vessels. They are used for treatment of erectile dysfunction and of pulmonary arterial hypertension. As well as PDE5, there are further, exclusively cGMP-cleaving phosphodiesterases (Stasch J.-P. et al. *Circulation* 2011).

As stimulators of soluble guanylate cyclase, WO 00/06568 and WO 00/06569 disclose fused pyrazole derivatives, and WO 03/095451 carbamate-substituted 3-pyrimidinylpyrazolopyridines. 3-Pyrimidinylpyrazolopyridines with phenylamide substituents are described in E. M. Becker et al., *BMC Pharmacology* 1 (13), 2001. WO 2004/009590 describes pyrazolopyridines with substituted 4-aminopyrimidines for treatment of CNS disorders. WO 2010/065275 and WO 2011/149921 disclose substituted pyrrolo- and dihydropyridopyrimidines as sGC activators. As sGC stimulators, WO 2012/004259 describes fused aminopyrimidines, and WO 2012/004258, WO 2012/143510 and WO 2012/152629 fused pyrimidines and triazines. WO 2012/28647 discloses pyrazolopyridines with various azaheterocycles for treatment of cardiovascular disorders.

It was an object of the present invention to provide novel substances which act as stimulators of soluble guanylate cyclase and as stimulators of soluble guanylate cyclase and phosphodiesterase-5 inhibitors (dual principle) and have an identical or improved therapeutic profile compared to the compounds known from the prior art, for example with respect to their in vivo properties, for example their pharmacokinetic and pharmacodynamic characteristics and/or their metabolic profile and/or their dose-activity relationship.

The present invention provides compounds of the general formula (I)

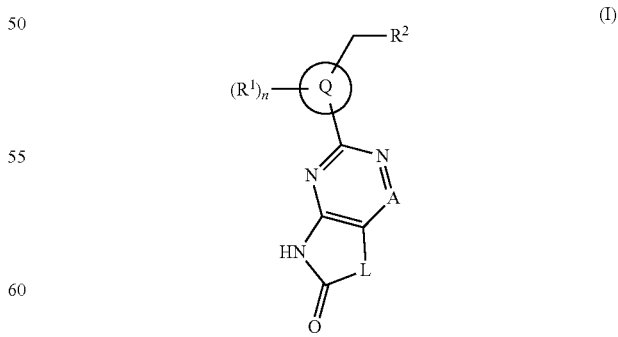

in which
A is nitrogen or $CR^3$
  where
    $R^3$ is hydrogen, deuterium, fluorine, chlorine, iodine, difluoromethyl, trifluoromethyl, $(C_1-C_4)$-alkyl, $(C_2-C_4)$- alkenyl, $(C_2-C_4)$-alkynyl, cyclopropyl, cyclobutyl, phenyl or 5- or 6-membered heteroaryl, in which $(C_1-C_4)$-alkyl, $(C_2-C_4)$-alkenyl, $(C_2-C_4)$-alkynyl, phenyl and 5- or 6-membered heteroaryl may each be substituted by 1 to 3 substituents selected independently from the group comprising fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl, L is a #-$CR^{4A}R^{4B}$—$(CR^{5A}R^{5B})_m$-## group where \# is the attachment site to the carbonyl group, \#\# is the attachment site to the pyrimidine or triazine ring, m is a number 0, 1 or 2, $R^{4A}$ is hydrogen, fluorine, $(C_1-C_4)$-alkyl, hydroxyl or amino, in which $(C_1-C_4)$-alkyl may be substituted by 1 to 3 substituents selected independently from the group of fluorine, trifluoromethyl, hydroxyl, hydroxycarbonyl, $(C_1-C_4)$-alkoxycarbonyl and amino, $R^{4B}$ is hydrogen, fluorine, difluoromethyl, trifluoromethyl, $(C_1-C_6)$-alkyl, cyano, $(C_3-C_7)$-cycloalkyl, difluoromethoxy, trifluoromethoxy or a group of the formula -M-$R^6$, in which $(C_1-C_6)$-alkyl may be substituted by 1 to 3 substituents selected independently from the group of fluorine, cyano, trifluoromethyl, $(C_3-C_7)$-cycloalkyl, difluoromethoxy and trifluoromethoxy, and in which M is a bond or $(C_1-C_4)$-alkanediyl, $R^6$ is —(C=O)$_r$—$OR^7$, —(C=O)$_r$—$NR^7R^8$, —C(=S)—$NR^7R^8$, —$NR^7$—(C=O)—$R^{10}$, —$NR^7$—(C=O)—$OR^{10}$, —$NR$∂—(C=O)—$NR^8R^9$, —$NR^7$—$SO_2$—$NR^8R^9$, —$NR^7$—$SO_2$—$R^{10}$, —$S(O)_s$—$R^{10}$, —$SO_2$—$NR^7R^8$, 4- to 7-membered heterocyclyl, phenyl or 5- or 6-membered heteroaryl, in which r is the number 0 or 1, s is the number 0, 1 or 2, $R^7$, $R^8$ and $R^9$ are each independently hydrogen, $(C_1-C_6)$-alkyl, $(C_3-C_8)$-cycloalkyl, 4- to 7-membered heterocyclyl, phenyl or 5- or 6-membered heteroaryl, or $R^7$ and $R^8$ together with the atom(s) to which they are bonded form a 4- to 7-membered heterocycle, in which the 4- to 7-membered heterocycle may in turn be substituted by 1 or 2 substituents selected independently from the group of cyano, trifluoromethyl, $(C_1-C_6)$-alkyl, hydroxyl, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, or $R^8$ and $R^9$ together with the atom(s) to which they are bonded form a 4- to 7-membered heterocycle, in which the 4- to 7-membered heterocycle may in turn be substituted by 1 or 2 substituents selected independently from the group of cyano, trifluoromethyl, $(C_1-C_6)$-alkyl, hydroxyl, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, $R^{10}$ is $(C_1-C_6)$-alkyl or $(C_3-C_7)$-cycloalkyl, or $R^7$ and $R^{10}$ together with the atom(s) to which they are bonded form a 4- to 7-membered heterocycle, in which the 4- to 7-membered heterocycle may in turn be substituted by 1 or 2 substituents selected independently from the group of cyano, trifluoromethyl, $(C_1-C_6)$-alkyl, hydroxyl, oxo, $(C_1-C_6)$-alkoxy, trifluoromethoxy, $(C_1-C_6)$-alkoxycarbonyl, amino, mono-$(C_1-C_6)$-alkylamino and di-$(C_1-C_6)$-alkylamino, and in which 4- to 7-membered heterocyclyl, phenyl and 5- or 6-membered independently from the group of halogen, cyano, difluoromethyl, trifluoromethyl, $(C_1-C_6)$-alkyl, $(C_3-C_7)$-cycloalkyl, hydroxyl, oxo, thioxo and $(C_1-C_4)$-alkoxy, and in which the aforementioned $(C_1-C_4)$-alkyl, $(C_1-C_6)$-alkyl, $(C_3-C_8)$-cycloalkyl and 4- to 7-membered heterocyclyl groups, unless stated otherwise, may each independently additionally be substituted by 1 to 3 substituents selected independently from the group of fluorine, difluoromethyl, trifluoromethyl, $(C_1-C_6)$-alkyl, $(C_3-C_7)$-cycloalkyl, hydroxyl, difluoromethoxy, trifluoromethoxy, $(C_1-C_4)$-alkoxy, hydroxycarbonyl, $(C_1-C_4)$-alkoxycarbonyl, amino, phenyl, 4- to 7-membered heterocyclyl and 5- or 6-membered heteroaryl, or $R^{4A}$ and $R^{4B}$ together with the carbon atom to which they are bonded form a $(C_2-C_4)$-alkenyl group, an oxo group, a 3- to 6-membered carbocycle or a 4- to 7-membered heterocycle, in which the 3- to 6-membered carbocycle and the 4- to 7-membered heterocycle may each be substituted by 1 or 2 substituents selected independently from the group of fluorine and $(C_1-C_4)$-alkyl, $R^{5A}$ is hydrogen, fluorine, $(C_1-C_4)$-alkyl or hydroxyl, $R^{5B}$ is hydrogen, fluorine, $(C_1-C_4)$-alkyl or trifluoromethyl, the ring Q is 8- to 9-membered heteroaryl, $R^1$ is halogen, cyano, difluoromethyl, trifluoromethyl, $(C_1-C_4)$-alkyl, hydroxyl, oxo or $(C_1-C_4)$-alkoxy, n is a number 0, 1 or 2, $R^2$ is trifluoromethyl, $(C_1-C_6)$-alkyl, $(C_3-C_8)$-cycloalkyl, phenyl or 5- or 6-membered heteroaryl, where $(C_1-C_6)$-alkyl is substituted by a substituent selected from the group of difluoromethyl and trifluoromethyl, where $(C_1-C_6)$-alkyl may be substituted by 1 to 3 fluorine substituents, where $(C_3-C_8)$-cycloalkyl may be substituted by 1 or 2 substituents selected independently from the group of fluorine, methyl and methoxy, where phenyl is substituted by 1 to 3 fluorine substituents, where phenyl may be substituted by 1 or 2 substituents selected independently from the group of methyl and methoxy, and where 5- and 6-membered heteroaryl may be substituted by 1 or 2 substituents selected independently from the group of fluorine and methyl, and the N-oxides, salts, solvates, salts of N-oxides and solvates of the N-oxides or salts thereof.

Inventive compounds are the compounds of the formula (I) and the N-oxides, salts, solvates and solvates of the N-oxides and salts thereof, the compounds, encompassed by formula (I), of the formulae specified hereinafter and the N-oxides, salts, solvates and solvates of the N-oxides and salts thereof, and the compounds encompassed by formula (I) and specified hereinafter as working examples and the N-oxides, salts, solvates and solvates of the N-oxides and salts thereof, to the extent that the compounds encompassed by formula (I) and specified hereinafter are not already N-oxides, salts, solvates and solvates of the N-oxides and salts.

Preferred salts in the context of the present invention are physiologically compatible salts of the inventive compounds. Also encompassed are salts which are not themselves suitable for pharmaceutical applications but can be used, for example, for isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the inventive compounds which, in solid or liquid state, form a complex by coordination with solvent molecules. Hydrates are a specific form of the solvates in which the coordination is with water. Preferred solvates in the context of the present invention are hydrates.

Depending on their structure, the inventive compounds may exist in different stereoisomeric forms, i.e. in the form of configurational isomers or if appropriate also as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this, in particular HPLC chromatography on an achiral or chiral phase.

If the inventive compounds can occur in tautomeric forms, the present invention encompasses all tautomeric forms.

The present invention also encompasses all suitable isotopic variants of the inventive compounds. An isotopic variant of an inventive compound is understood here to mean a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of an inventive compound, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}H$ or $^{14}C$ isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the inventive compounds may therefore, in some cases, also constitute a preferred embodiment of the present invention. Isotopic variants of the inventive compounds can be prepared by the processes known to those skilled in the art, for example by the methods described below and the procedures described in the working examples, by using corresponding isotopic modifications of the respective reagents and/or starting compounds.

In addition, the present invention also encompasses prodrugs of the inventive compounds. The term "prodrugs" here denotes compounds which may themselves be biologically active or inactive, but are converted (for example metabolically or hydrolytically) to inventive compounds during their residence time in the body.

In the context of the present invention, the substituents, unless specified otherwise, are each defined as follows:

Alkyl in the context of the invention is a linear or branched alkyl radical having the number of carbon atoms specified in each case. Preferred examples include: methyl, ethyl, n-propyl, isopropyl, n-butyl, isobutyl, 1-methylpropyl, tert-butyl, n-pentyl, isopentyl, 1-ethylpropyl, 1-methylbutyl, 2-methylbutyl, 3-methylbutyl, n-hexyl, 1-methylpentyl, 2-methylpentyl, 3-methylpentyl, 4-methylpentyl, 3,3-dimethylbutyl, 1-ethylbutyl and 2-ethylbutyl.

Cycloalkyl or carbocycle in the context of the invention is a monocyclic saturated alkyl radical having the number of carbon atoms specified in each case. Preferred examples include: cyclopropyl, cyclobutyl, cyclopentyl, cyclohexyl and cycloheptyl.

5- to 7-membered saturated or partly unsaturated carbocycle in the context of the invention is a saturated or partly unsaturated cyclic alkyl radical having the number of carbon atoms specified in each case. Preferred examples include: cyclopentyl, cyclohexyl, cycloheptyl, cyclopentenyl, cyclohexenyl and cycloheptenyl.

Alkanediyl in the context of the invention is a linear or branched divalent alkyl radical having 1 to 4 carbon atoms. Preferred examples include: methylene, ethane-1,2-diyl, ethane-1,1-diyl, propane-1,3-diyl, propane-1,1-diyl, propane-1,2-diyl, propane-2,2-diyl, butane-1,4-diyl, butane-1,2-diyl, butane-1,3-diyl and butane-2,3-diyl.

Alkenyl in the context of the invention is a linear or branched alkenyl radical having 2 to 4 carbon atoms and a double bond. Preferred examples include: vinyl, allyl, isopropenyl and n-but-2-en-1-yl.

Alkynyl in the context of the invention is a linear or branched alkynyl radical having 2 to 4 carbon atoms and a triple bond. Preferred examples include: ethynyl, n-prop-1-yn-1-yl, n-prop-2-yn-1-yl, n-but-2-yn-1-yl and n-but-3-yn-1-yl.

Alkoxy in the context of the invention is a linear or branched alkoxy radical having 1 to 6 or 1 to 4 carbon atoms. Examples include: methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Preference is given to a linear or branched alkoxy radical having 1 to 4 carbon atoms. Preferred examples include: methoxy, ethoxy, n-propoxy, isopropoxy, 1-methylpropoxy, n-butoxy, isobutoxy, tert-butoxy.

Alkoxycarbonyl in the context of the invention is a linear or branched alkoxy radical having 1 to 6 or 1 to 4 carbon atoms and a carbonyl group attached to the oxygen. Preferred examples include: methoxycarbonyl, ethoxycarbonyl, n-propoxycarbonyl, isopropoxycarbonyl and tert-butoxycarbonyl.

Monoalkylamino in the context of the invention is an amino group having a linear or branched alkyl substituent having 1 to 6 carbon atoms. Preferred examples include: methylamino, ethylamino, n-propylamino, isopropylamino and tert-butylamino.

Dialkylamino in the context of the invention is an amino group having two identical or different, linear or branched alkyl substituents each having 1 to 6 carbon atoms. Preferred examples include: N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

5- to 7-membered saturated or partly unsaturated heterocycle in the context of the invention is a saturated or partly unsaturated heterocycle which has a total of 5 to 7 ring atoms and contains one ring heteroatom from the group of N, O, S, SO and/or $SO_2$. Examples include: pyrrolidinyl, tetrahydrofuranyl, piperidinyl, tetrahydropyranyl, dihydropyrrolyl, dihydropyridyl.

Heterocyclyl or heterocycle in the context of the invention is a saturated heterocycle which has a total of 4 to 7 ring atoms and contains one or two ring heteroatoms from the group of N, O, S, SO and/or $SO_2$. Examples include: azetidinyl, oxetanyl, pyrrolidinyl, pyrazolidinyl, imidazolinyl, tetrahydrofuranyl, piperidinyl, piperazinyl, tetrahydropyranyl, morpholinyl, thiomorpholinyl and dioxidothiomorpholinyl. Preference is given to azetidinyl, oxetanyl, pyrrolidinyl, tetrahydrofuranyl, piperidinyl, tetrahydropyranyl and morpholinyl.

5- or 6-membered heteroaryl in the context of the invention is a monocyclic aromatic heterocycle (heteroaromatic) which has a total of 5 or 6 ring atoms, contains up to three identical or different ring heteroatoms from the group of N, O and/or S and is attached via a ring carbon atom or optionally via a ring nitrogen atom. Preferred examples include: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl and triazinyl. Preference is given to: pyrazolyl, oxazolyl, thiazolyl, triazolyl, oxadiazolyl, thiadiazolyl, pyridyl and pyrimidinyl.

8- or 9-membered heteroaryl in the context of the invention is a bicyclic aromatic or partly unsaturated heterocycle which has a total of 8 or 9 ring atoms and contains at least two nitrogen atoms and up to two further, identical or different ring heteroatoms from the group of N, O and/or S. Examples include: dihydrothienopyrazolyl, thienopyrazolyl, pyrazolopyrazolyl, imidazothiazolyl, tetrahydrocyclopentapyrazolyl, dihydrocyclopentapyrazolyl, tetrahydroindazolyl, dihydroindazolyl, indazolyl, pyrazolo[4,3-b]pyridyl, tetrahydropyrazolopyridinyl, pyrazolopyrimidinyl, imidazo[1,5-a]pyridyl and imidazopyrimidinyl.

Halogen in the context of the invention is fluorine, chlorine, bromine and iodine. Preference is given to bromine and iodine.

An oxo group in the context of the invention is an oxygen atom bonded via a double bond to a carbon atom.

A thioxo group in the context of the invention is a sulphur atom bonded via a double bond to a carbon atom.

In the formula of the group which may be represented by L or Q, the end point of the line marked by the symbol #, ##, * and ** is not a carbon atom or a $CH_2$ group but is part of the bond to the respective atom to which L or Q is bonded.

When radicals in the inventive compounds are substituted, the radicals, unless specified otherwise, may be mono- or polysubstituted. In the context of the present invention, all radicals which occur more than once are each defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progress of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which A is nitrogen or $CR^3$
    where
    $R^3$ is hydrogen, deuterium, fluorine, chlorine, iodine, difluoromethyl, trifluoromethyl, $(C_1-C_4)$-alkyl, vinyl, allyl, ethynyl, cyclopropyl, cyclobutyl, hydroxyl, pyrazolyl or pyridyl,
        in which $(C_1-C_4)$-alkyl, vinyl, allyl, ethynyl and pyridyl may each be substituted by 1 or 2 substituents selected independently from the group comprising methyl, cyclopropyl and cyclobutyl, L is a #-$CR^{4A}R^{4B}$—$(CR^{5A}R^{5B})_m$-## group
    where
    # is the attachment site to the carbonyl group,
    ## is the attachment site to the pyrimidine or triazine ring,
    m is a number 0, 1 or 2,
    $R^{4A}$ is hydrogen, fluorine, methyl, ethyl, hydroxyl or amino,
    $R^{4B}$ is hydrogen, fluorine, difluoromethyl, trifluoromethyl, $(C_1-C_4)$-alkyl, cyano, cyclopropyl, cyclobutyl, cyclopentyl or a group of the formula -M-$R^6$,
        in which $(C_1-C_4)$-alkyl may be substituted by 1 to 3 substituents selected independently from the group of fluorine, cyano, trifluoromethyl, cyclopropyl, cyclobutyl, cyclopentyl, difluoromethoxy and trifluoromethoxy,
    and in which
    M is a bond, methylene, ethane-1,2-diyl or propane-1,3-diyl,
    $R^6$ is —(C=O)$_r$—$OR^7$, —(C=O)$_r$—$NR^7R^8$, —C(=S)—$NR^7R^8$, —$NR^7$—(C=O)—$OR^{10}$, oxadiazolonyl, oxadiazolothionyl, phenyl, oxazolyl, thiazolyl, pyrazolyl, triazolyl, oxadiazolyl, thiadiazolyl, pyridyl, pyrimidinyl or pyrazinyl,
    in which
    r is the number 0 or 1,
    $R^7$ and $R^8$ are each independently hydrogen, methyl, ethyl, isopropyl, cyclopropyl, cyclobutyl, cyclopentyl, oxetanyl, azetidinyl, tetrahydrofuranyl, pyrrolidinyl, tetrahydropyranyl, piperidinyl, piperazinyl, morpholinyl, phenyl, pyrazolyl or pyridyl, in which methyl, ethyl and isopropyl may additionally be substituted by 1 or 2 substituents selected independently from the group of fluorine, difluoromethyl, trifluoromethyl, cyclopropyl, cyclobutyl, cyclopentyl, hydroxyl, difluoromethoxy, trifluoromethoxy, methoxy, ethoxy, hydroxycarbonyl, methoxycarbonyl, ethoxycarbonyl and amino, $R^{16}$ is methyl, ethyl, isopropyl, cyclopropyl, cyclobutyl, cyclopentyl, and in which oxadiazolonyl, oxadiazolothionyl, phenyl, oxazolyl, thiazolyl, pyrazolyl, triazolyl, oxadiazolyl, thiadiazolyl, pyridyl, pyrimidinyl and pyrazinyl may each in turn be substituted by 1 or 2 substituents selected independently from the group of fluorine, chlorine, cyano, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl, cyclobutylmethyl, hydroxyl, methoxy and ethoxy, or $R^{4A}$ and $R^{4B}$ together with the carbon atom to which they are bonded form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring may each be substituted by 1 or 2 substituents selected independently from the group of fluorine and methyl, $R^{5A}$ is hydrogen, fluorine, methyl, ethyl or hydroxyl, $R^{5B}$ is hydrogen, fluorine, methyl, ethyl or trifluoromethyl, the ring Q is a group of the formula

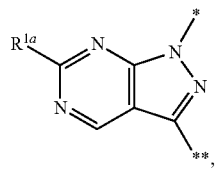
(a-1)

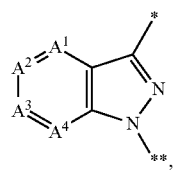
(b-1)

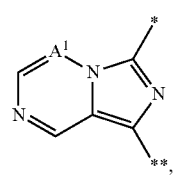
(c-1)

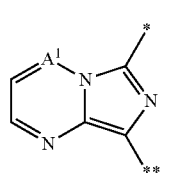
(c-1b)

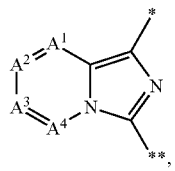
(d-1)

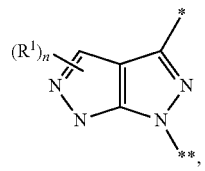
(e-1)

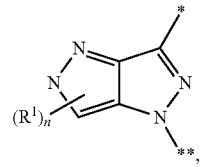
(f-1)

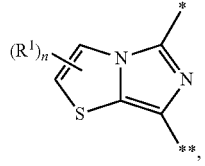
(g-1)

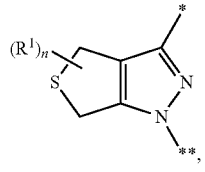
(h-1)

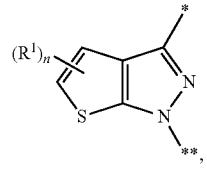
(i-1)

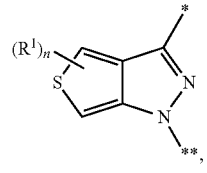
(j-1)

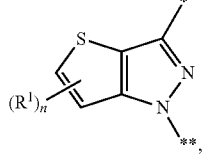
(k-1)

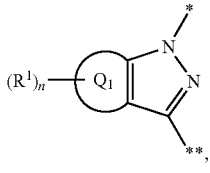
(l-1)

-continued

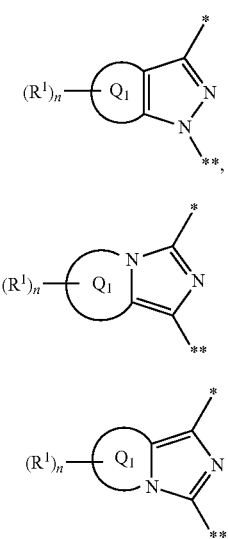

where
* is the attachment site to —CH$_2$—R$^2$,
** is the attachment site to the pyrimidine or triazine ring,
the ring Q$_1$ together with the atoms to which it is bonded forms a 5- to 7-membered saturated or partly unsaturated carbocycle or a 5- to 7-membered saturated or partly unsaturated heterocycle,
R$^{1a}$ is hydrogen or methyl,
R$^1$ is fluorine, chlorine, methyl, hydroxyl or oxo,
n is a number 0, 1 or 2,
A$^1$, A$^2$, A$^3$ and A$^4$ are each independently N, CH or CR$^1$,
with the proviso that not more than two of the A$^1$, A$^2$, A$^3$ and A$^4$ groups are N,
R$^2$ is trifluoromethyl, 2,2,2-trifluoroethyl, 3,3,3-trifluoroprop-1-yl, 2,2,3,3,3-pentafluoroprop-1-yl, cyclopropyl, cyclobutyl, cyclopentyl, cyclohexyl, phenyl, pyridyl, pyrimidinyl, pyrazinyl or pyridazinyl,
where phenyl is substituted by 1 to 3 fluorine substituents, and
where cyclopropyl, cyclobutyl, cyclopentyl, cyclohexyl, pyridyl, pyrimidinyl, pyrazinyl and pyridazinyl may each be substituted by 1 or 2 fluorine substituents,
and the salts, solvates and solvates of the salts thereof.

Preference is also given in the context of the present invention to compounds of the formula (I) in which
A is nitrogen or CR$^3$
where
R$^3$ is hydrogen, fluorine, difluoromethyl, trifluoromethyl, methyl, ethyl, cyclopropyl or cyclobutyl,
L is a #-CR$^{4A}$R$^{4B}$—(CR$^{5A}$R$^{5B}$)$_m$-## group
where
# is the attachment site to the carbonyl group,
## is the attachment site to the pyrimidine or triazine ring,
m is a number 0,
R$^{4A}$ is hydrogen, fluorine, methyl, ethyl, hydroxyl or amino,
R$^{4B}$ is hydrogen, fluorine, difluoromethyl, trifluoromethyl, methyl, ethyl, cyclopropyl, cyclobutyl, cyclopentyl or a group of the formula -M-R$^6$,
in which methyl and ethyl may each be substituted by 1 to 3 substituents selected independently from the group of fluorine, cyano, trifluoromethyl, cyclopropyl, cyclobutyl, difluoromethoxy and trifluoromethoxy,
and in which
M is a bond,
R$^6$ is —(C═O)$_r$—NR$^7$R$^8$, phenyl, thiazolyl, triazolyl, oxadiazolyl, thiadiazolyl or pyrimidinyl,
in which
r is the number 1,
R$^7$ and R$^8$ are each independently hydrogen, or cyclopropyl,
and
in which phenyl, thiazolyl, triazolyl, oxadiazolyl, thiadiazolyl and independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
or
R$_{4A}$ and R$^{4B}$ together with the carbon atom to which they are bonded form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may each be substituted by 1 or 2 substituents selected independently from the group of fluorine and methyl,
the ring Q is a group of the formula

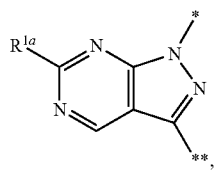
(a-1)

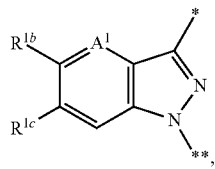
(b-1a)

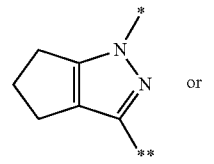
(1-1a)
or

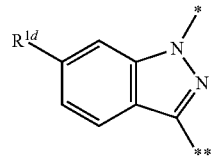
(1-1b)

where
* is the attachment site to —CH$_2$—R$^2$,
** is the attachment site to the pyrimidine or triazine ring,
R$^{1a}$ is hydrogen or methyl,
R$^{1b}$ is hydrogen, fluorine or chlorine,
R$^{1c}$ is hydrogen or fluorine,
R$^{1d}$ is hydrogen or chlorine, $A^1$ is N or CH, $R^2$ is 3,3,3-trifluoroprop-1-yl, 2,2,3,3-tetrafluoroprop-1-yl, 2,2,3,3,3-pentafluoroprop-1-yl, phenyl or pyridyl, where phenyl is substituted by 1 to 3 fluorine substituents, and where pyridyl may be substituted by 1 fluorine substituent, and the salts, solvates and solvates of the salts thereof.

Preference is also given in the context of the present invention to compounds of the formula (I) in which A is nitrogen or $CR^3$ where $R^3$ is hydrogen, fluorine, difluoromethyl, trifluoromethyl, methyl, ethyl, cyclopropyl or cyclobutyl, L is a #-$CR^{4A}R^{4B}$—$(CR^{5A}R^{5B})_m$-## group where # is the attachment site to the carbonyl group, ## is the attachment site to the pyrimidine or triazine ring, m is a number 0, $R^{4A}$ is hydrogen, fluorine, methyl, ethyl, hydroxyl or amino, $R^{4B}$ is hydrogen, fluorine, difluoromethyl, trifluoromethyl, methyl, ethyl, cyclopropyl, cyclobutyl, cyclopentyl or a group of the formula -M-$R^6$, in which methyl and ethyl may each be substituted by 1 to 3 substituents selected independently from the group of fluorine, cyano, trifluoromethyl, cyclopropyl, cyclobutyl, difluoromethoxy and trifluoromethoxy, where $R^{4B}$ is hydrogen, difluoromethyl, trifluoromethyl, methyl, ethyl, cyclopropyl, cyclobutyl, cyclopentyl or a group of the formula -M-$R^6$ when $R^{4A}$ is hydroxyl, and in which M is a bond, $R^6$ is —$(C=O)_r$—$NR^7R^8$, phenyl, thiazolyl, triazolyl, oxadiazolyl, thiadiazolyl or pyrimidinyl, in which r is the number 1, $R^7$ and $R^8$ are each independently hydrogen, or cyclopropyl, and in which phenyl, thiazolyl, triazolyl, oxadiazolyl, thiadiazolyl and pyrimidinyl may each in turn be substituted by 1 or 2 substituents selected independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl, or $R^{4A}$ and $R^{4B}$ together with the carbon atom to which they are bonded form a cyclopropyl, cyclobutyl, cyclopentyl, azetidinyl, tetrahydrofuranyl, pyrrolidinyl or tetrahydropyranyl ring, in which the cyclopropyl, cyclobutyl, cyclopentyl, azetidinyl, tetrahydrofuranyl, pyrrolidinyl and tetrahydropyranyl ring may each be substituted by 1 or 2 substituents selected independently from the group of fluorine and methyl, the ring Q is a group of the formula (a-1)

(b-1a)

(1-1a)

(1-1b)

where

\* is the attachment site to —$CH_2$—$R^2$,

\*\* is the attachment site to the pyrimidine or triazine ring, $A^1$ is N or CH, $R^{1a}$ is hydrogen or methyl, $R^{1b}$ is hydrogen, fluorine or chlorine when $A^1$ is CH, $R^{1b}$ is hydrogen when $A^1$ is N, $R^{1c}$ is hydrogen or fluorine, $R^{1d}$ is hydrogen or chlorine, $R^2$ is 3,3,3-trifluoroprop-1-yl, 2,2,3,3-tetrafluoroprop-1-yl, 2,2,3,3,3-pentafluoroprop-1-yl, phenyl or pyridyl, where phenyl is substituted by 1 to 3 fluorine substituents, and where pyridyl may be substituted by 1 fluorine substituent, and the salts, solvates and solvates of the salts thereof.

Particular preference is given in the context of the present invention to compounds of the formula (I) in which A is nitrogen or $CR^3$ where $R^3$ represents hydrogen, L is a #-$CR^{4A}R^{4B}$—$(CR^{5A}R^{5B})_m$-## group where # is the attachment site to the carbonyl group, ## is the attachment site to the pyrimidine or triazine ring, m is a number 0, $R^{4A}$ is hydrogen, fluorine, methyl or hydroxyl, $R^{4B}$ is hydrogen, fluorine, trifluoromethyl, 2,2,2-trifluoroethyl or methyl, the ring Q is a group of the formula

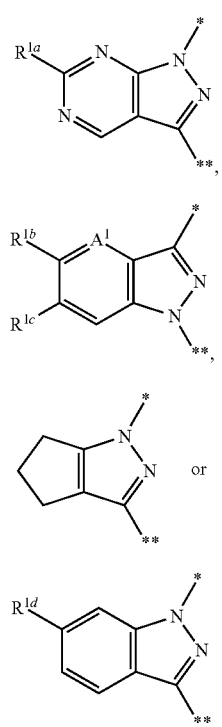

(a-1)

(b-1a)

(1-1a)

or (1-1b)

where
* is the attachment site to —CH$_2$—R$^2$,
** is the attachment site to the pyrimidine or triazine ring,
R$^{1a}$ is hydrogen or methyl,
R$^{1b}$ is hydrogen, fluorine or chlorine,
R$^{1c}$ is hydrogen or fluorine,
R$^{1d}$ is hydrogen or chlorine,
A$^1$ is N or CH,
R$^2$ is 3,3,3-trifluoroprop-1-yl, 2,2,3,3,3-pentafluoroprop-1-yl, phenyl or pyridyl,
  where phenyl is substituted by 1 to 3 fluorine substituents, and
  where pyridyl may be substituted by 1 fluorine substituent,
and the salts, solvates and solvates of the salts thereof.
Particular preference is given in the context of the present invention to compounds of the formula (I) in which
A is nitrogen or CR$^3$
  where
  R$^3$ is hydrogen,
L is a #-CR$^{4A}$R$^{4B}$—(CR$^{5A}$R$^{5B}$)$_m$-## group
  where
  # is the attachment site to the carbonyl group,
  ## is the attachment site to the pyrimidine or triazine ring,
  m is a number 0,
  R$^{4A}$ is hydrogen, fluorine, methyl or hydroxyl,
  R$^{4B}$ is hydrogen, fluorine, trifluoromethyl, 2,2,2-trifluoroethyl or methyl, provided that R$^{4B}$ is not fluorine when R$^{4A}$ is hydroxyl, the ring Q is a group of the formula

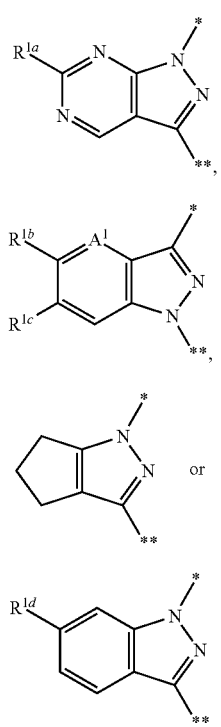

(a-1)

(b-1a)

(1-1a)

or (1-1b)

where
* is the attachment site to —CH$_2$—R$^2$,
** is the attachment site to the pyrimidine or triazine ring,
A$^1$ is N or CH,
R$^{1a}$ is hydrogen or methyl,
R$^{1b}$ is hydrogen, fluorine or chlorine when A$^1$ is CH,
R$^{1b}$ is hydrogen when A$^1$ is N,
R$^{1c}$ is hydrogen or fluorine,
R$^{1d}$ is hydrogen or chlorine,
R$^2$ is 3,3,3-trifluoroprop-1-yl, 2,2,3,3,3-pentafluoroprop-1-yl, phenyl or pyridyl,
  where phenyl is substituted by 1 to 3 fluorine substituents, and
  where pyridyl may be substituted by 1 fluorine substituent,
and the salts, solvates and solvates of the salts thereof.
Particular preference is given in the context of the present invention to compounds of the formula (I) in which
A is nitrogen or CR$^3$
  where
  R$^3$ is hydrogen,
L is a #-CR$^{4A}$R$^{4B}$—(CR$^{5A}$R$^{5B}$)$_m$-## group
  where
  # is the attachment site to the carbonyl group,
  ## is the attachment site to the pyrimidine or triazine ring,
  m is a number 0,
R$^{4A}$ is methyl,
R$^{4B}$ is methyl, the ring Q is a group of the formula (a-1)

[Structure: Rˡᵃ-substituted pyrazolo-pyrimidine ring]

(b-1)

[Structure: Rˡᵇ, Rˡᶜ-substituted A¹-containing pyrazolo-pyridine ring] or (1-1b)

[Structure: Rˡᵈ-substituted indazole]

where
* is the attachment site to —CH₂—R²,
** is the attachment site to the pyrimidine or triazine ring,
A¹ is N or CH,
$R^{1a}$ is hydrogen or methyl,
$R^{1b}$ is hydrogen, fluorine or chlorine when A¹ is CH,
$R^{1b}$ is hydrogen when A¹ is N,
$R^{1c}$ is hydrogen or fluorine,
$R^{1d}$ is hydrogen or chlorine,
R² is 2,2,3,3,3-pentafluoroprop-1-yl, phenyl or pyridyl,
where phenyl is substituted by 1 or 2 fluorine substituents, and
where pyridyl may be substituted by 1 fluorine substituent, and the salts, solvates and solvates of the salts thereof.

Particular preference is given in the context of the present invention to compounds of the formula (I) in which
A is nitrogen,
L is a #-$CR^{4A}R^{4B}$—$(CR^{5A}R^{5B})_m$-## group
where
# is the attachment site to the carbonyl group,
## is the attachment site to the triazine ring,
m is a number 0,
$R^{4A}$ is methyl,
$R^{4B}$ is methyl,
the ring Q is a group of the formula (a-1)

[Structure: Rˡᵃ-substituted pyrazolo-pyrimidine ring]

(b-1)

[Structure: Rˡᵇ, Rˡᶜ-substituted A¹-containing pyrazolo-pyridine ring] or (1-1b)

[Structure: Rˡᵈ-substituted indazole]

where
* is the attachment site to —CH₂—R²,
** is the attachment site to the triazine ring,
A¹ is N or CH,
$R^{1a}$ is hydrogen or methyl,
$R^{1b}$ is hydrogen, fluorine or chlorine when A¹ is CH,
$R^{1b}$ is hydrogen when A¹ is N,
$R^{1c}$ is hydrogen or fluorine,
$R^{1d}$ is hydrogen or chlorine,
R² is phenyl,
where phenyl is substituted by 1 or 2 fluorine substituents,
and the salts, solvates and solvates of the salts thereof.

Particular preference is given in the context of the present invention to the following compounds:

[Structure of compound with fluorophenyl, pyrazolopyridine, triazine, and pyrrolone dimethyl groups]

[Structure of compound with fluorophenyl, methyl-pyrazolopyrimidine, triazine, and pyrrolone dimethyl groups]

-continued

[Chemical structure diagrams]

and the salts, solvates and solvates of the salts thereof.

Preference is also given in the context of the present invention to compounds of the formula (I) in which A is N or CH, and the salts, solvates and solvates of the salts thereof.

Preference is also given in the context of the present invention to compounds of the formula (I) in which A is N, and the salts, solvates and solvates of the salts thereof.

Preference is also given in the context of the present invention to compounds of the formula (I) in which A is CH, and the salts, solvates and solvates of the salts thereof.

Preference is also given in the context of the present invention to compounds of the formula (I) in which
A is nitrogen,
L is a #-$CR^{4A}R^{4B}$—$(CR^{5A}R^{5B})_m$-## group
where
  # is the attachment site to the carbonyl group,
  ## is the attachment site to the triazine ring,
  m is a number 0,
  $R^{4A}$ is methyl,
  $R^{4B}$ is methyl,
and
Q, n, $R^1$ and $R^2$ are each as defined above,
and the salts, solvates and solvates of the salts thereof.

Preference is also given in the context of the present invention to compounds of the formula (I) in which
the ring Q is a group of the formula

[Chemical structure diagrams labeled (a-1), (b-1a), (b-1b), (1-1b)]

where
* is the attachment site to —$CH_2$—$R^2$,
** is the attachment site to the pyrimidine or triazine ring,
$R^{1a}$ is hydrogen or methyl,
$R^{1b}$ is hydrogen, fluorine or chlorine,
$R^{1c}$ is hydrogen or fluorine,
$R^{1d}$ is chlorine,
$A^1$ is N or CH,
and the salts, solvates and solvates of the salts thereof.

Preference is also given in the context of the present invention to compounds of the formula (I) in which
A is nitrogen,
L is a #-$CR^{4A}R^{4B}$—$(CR^{5A}R^{5B})_m$-## group
where
  # is the attachment site to the carbonyl group,
  ## is the attachment site to the triazine ring,
  m is a number 0, $R^{4A}$ is hydrogen, fluorine, methyl, ethyl, hydroxyl or amino, $R^{4B}$ is a group of the formula -M-$R^6$, and in which M is a bond, $R^6$ is —(C=O)$_r$—NR$^7$R$^8$, phenyl, thiazolyl, triazolyl, oxadiazolyl, thiadiazolyl or pyrimidinyl, in which r is the number 1, $R^7$ and $R^8$ are each independently hydrogen, or cyclopropyl, and in which phenyl, thiazolyl, triazolyl, oxadiazolyl, thiadiazolyl and pyrimidinyl may each in turn be substituted by 1 or 2 substituents selected independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl, and the salts, solvates and solvates of the salts thereof.

Preference is also given in the context of the present invention to compounds of the formula (I) in which A is $CR^3$ where $R^3$ is hydrogen, L is a #-$CR^{4A}R^{4B}$—$(CR^{5A}R^{5B})_m$-## group where # is the attachment site to the carbonyl group, ## is the attachment site to the pyrimidine ring, m is a number 1, $R^{4A}$ is hydrogen, fluorine, methyl, ethyl, hydroxyl or amino, $R^{4B}$ is a group of the formula -M-$R^6$, and in which M is a bond, $R^6$ is —(C=O)$_r$—NR$^7$R$^8$, phenyl, thiazolyl, triazolyl, oxadiazolyl, thiadiazolyl or pyrimidinyl, in which r is the number 1, $R^7$ and $R^8$ are each independently hydrogen, or cyclopropyl, and in which phenyl, thiazolyl, triazolyl, oxadiazolyl, thiadiazolyl and pyrimidinyl may each in turn be substituted by 1 or 2 substituents selected independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl, and the salts, solvates and solvates of the salts thereof.

The individual radical definitions specified in the particular combinations or preferred combinations of radicals are, independently of the particular combinations of the radicals specified, also replaced as desired by radical definitions of other combinations.

Particular preference is given to combinations of two or more of the preferred ranges mentioned above.

The invention further provides a process for preparing the inventive compounds of the formula (I), characterized in that

[A] a compound of the formula (II)

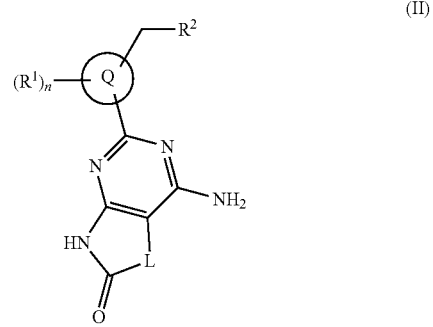

(II)

in which n, L, Q, $R^1$ and $R^2$ are each as defined above is reacted, then this is converted using isopentyl nitrite and a halogen equivalent to a compound of the formula (I-A)

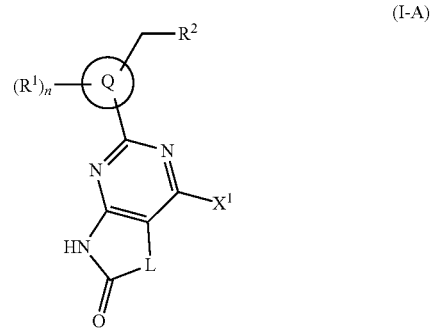

(I-A)

in which n, L, Q, $R^1$ and $R^2$ are each as defined above and $X^1$ is bromine or iodine, or

[B] a compound of the formula (I-A) is reacted in an inert solvent in the presence of a suitable transition metal catalyst to give a compound of the formula (I-B)

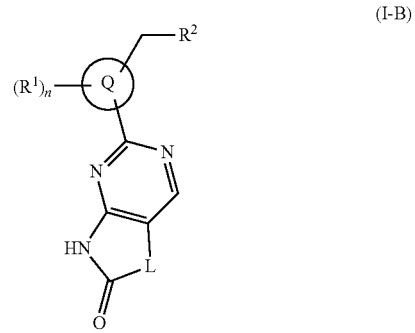

(I-B)

in which n, L, Q, $R^1$ and $R^2$ are each as defined above, or

[C] a compound of the formula (I-A) is reacted in an inert solvent in the presence of a suitable transition metal catalyst with a compound of the formula (III-A), (III-B) or (III-C)

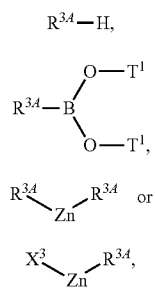
(III-A) $R^{3A}$—H, (III-B)

(III-C) $R^{3A}$—Zn—$R^{3A}$  or (III-D) $X^3$—Zn—$R^{3A}$, in which $R^{3A}$ is halogen, difluoromethyl, trifluoromethyl, $(C_1-C_4)$-alkyl, $(C_2-C_4)$-alkenyl, $(C_2-C_4)$-alkynyl, cyclopropyl, cyclobutyl, phenyl or 5- or 6-membered heteroaryl,
  in which $(C_1-C_4)$-alkyl, $(C_2-C_4)$-alkenyl, $(C_2-C_4)$-alkynyl, phenyl and 5- or 6-membered heteroaryl may each be substituted by 1 to 3 substituents selected independently from the group comprising fluorine, difluoromethyl, trifluoromethyl, $(C_1-C_4)$-alkyl, difluoromethoxy, trifluoromethoxy, $(C_1-C_4)$-alkoxy, $(C_1-C_4)$-alkoxycarbonyl, cyclopropyl and cyclobutyl, $T^1$ is hydrogen or $(C_1-C_4)$-alkyl, or both $R^{11}$ radicals together form a —C(CH$_3$)$_2$—C(CH$_3$)$_2$— bridge, and $X^3$ is bromine or iodine, to give a compound of the formula (I-C)

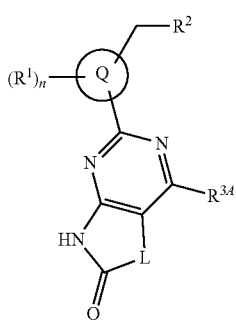
(I-C)

in which n, L, Q, $R^1$, $R^2$ and $R^{3A}$ are each as defined above, or

[D] is reacted in an inert solvent in the presence of a suitable base with hydrazine hydrate to give a compound of the formula (IV)

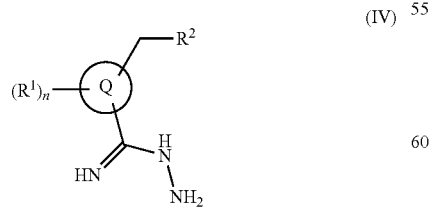
(IV)

in which n, L, Q, R' and $R^2$ are each as defined above, this is then reacted in an inert solvent with a compound of the formula (V)

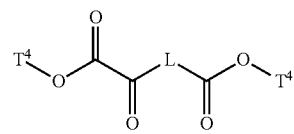
(V)

in which L is as defined above and $T^4$ is $(C_1-C_4)$-alkyl to give a compound of the formula (VI)

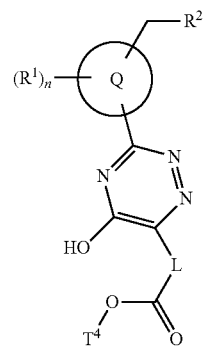
(VI)

in which n, L, Q, $R^1$, $R^2$ and $T^4$ are each as defined above, then this is converted using phosphoryl chloride to a compound of the formula (VII)

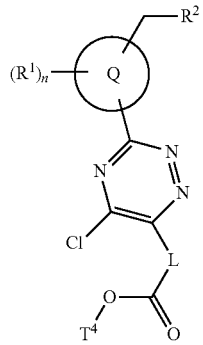
(VII)

in which n, L, Q, $R^1$, $R^2$ and $T^4$ are each as defined above, and this is reacted directly with ammonia to give a compound of the formula (VIII)

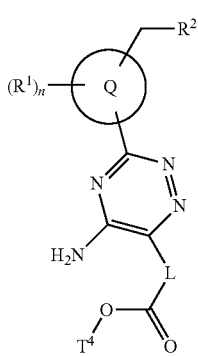
(VIII)

in which n, L, Q, $R^1$, $R^2$ and $T^4$ are each as defined above, and finally cyclized in an inert solvent, optionally in the presence of a suitable base, to give a compound of the formula (I-D)

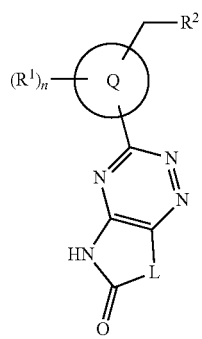
(I-D)

in which n, L, Q, $R^1$ and $R^2$ are each as defined above,
or
[E] a compound of the formula (X)

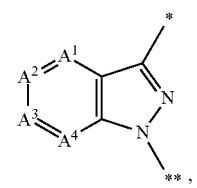
(X)

in which n, $R^1$ and $R^2$ are each as defined above and the ring $Q^2$ is a group of the formula

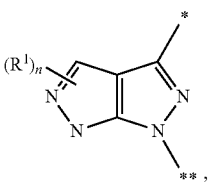
(b-1)

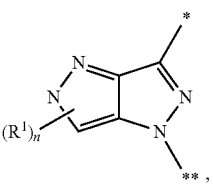
(e-1)

(f-1)

(h-1)

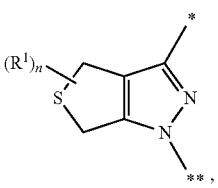

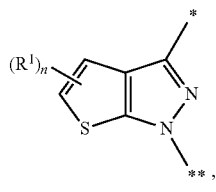
(i-1)

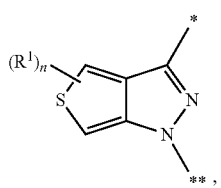
(j-1)

(k-1)

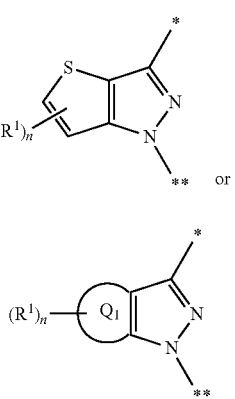

or (m-1)

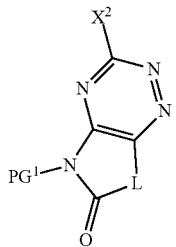

where
* is the attachment site to —$CH_2$—$R^2$,
** is the attachment site to the hydrogen atom,
the ring $Q_1$ together with the atoms to which it is bonded forms a 5- to 7-membered saturated or partly unsaturated carbocycle or a 5- to 7-membered saturated or partly unsaturated heterocycle,
$R^1$ is fluorine, chlorine, methyl, hydroxyl or oxo,
n is a number 0, 1 or 2,
$A^1$, $A^2$, $A^3$ and $A^4$ are each independently N, CH or $CR^1$,
with the proviso that not more than two of the $A^1$, $A^2$, $A^3$ and $A^4$ groups are N,
is converted in an inert solvent, optionally in the presence of a suitable base, with a compound of the formula (XI)

(XI)

PG¹—N in which L is as defined above,
$X^2$ is chlorine or bromine and
$PG^1$ is a suitable amino protecting group, especially p-methoxybenzyl, to give a compound of the formula (XII)

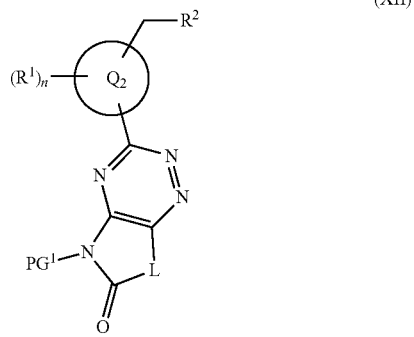

in which n, L, $Q_2$, $R^1$, $R^2$ and $PG^1$ are each as defined above, the protecting group $PG^1$ is subsequently detached therefrom to give a compound of the formula (I-E)

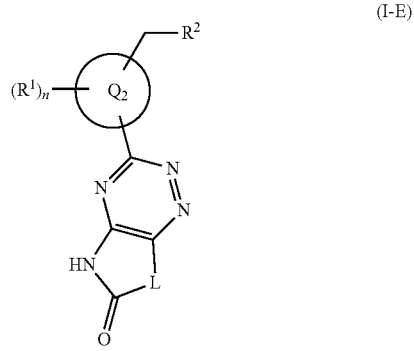

in which n, L, $Q_2$, $R^1$ and $R^2$ are each as defined above, and, if appropriate, the resulting compounds of the formulae (I-A), (I-B), (I-C), (I-D) and (I-E) are optionally converted with the appropriate (i) solvents and/or (ii) acids or bases to the solvates, salts and/or solvates of the salts thereof.

The compounds of the formulae (I-A), (I-B), (I-C), (I-D) and (I-E) together form the group of inventive compounds of the formula (I).

Process step (II)→(I-A) is effected with or without solvent. Suitable solvents are all organic solvents which are inert under the reaction conditions. A preferred solvent is dimethoxyethane.

The reaction (II)→(I-A) is effected generally within a temperature range from +20° C. to +100° C., preferably within the range from +50° C. to +100° C., optionally in a microwave. The conversion can be performed at standard, elevated or reduced pressure (for example in the range from 0.5 to 5 bar). In general, standard pressure is employed.

Suitable halogen sources in the reaction (II)→(I-A) are, for example, diiodomethane, a mixture of caesium iodide, iodine and copper(I) iodide or copper(II) bromide.

Process step (II)→(I-A), in the case of diiodomethane as the halogen source, is effected with a molar ratio of 10 to 30 mol of isopentyl nitrite and 10 to 30 mol of the iodine equivalent based on 1 mol of the compound of the formula (II).

Inert solvents for the process step (I-A)→(I-B) are alcohols such as methanol, ethanol, n-propanol, isopropanol, n-butanol, tert-butanol or 1,2-ethanediol, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. Preference is given to DMF.

The reduction (I-A)→(I-B) is effected with hydrogen in conjunction with transition metal catalysts, for example palladium (10% on activated carbon), Raney nickel or palladium hydroxide.

The reaction (I-A)→(I-B) is effected generally within a temperature range from +20° C. to +50° C.

The conversion can be performed at standard or elevated pressure (for example in the range from 0.5 to 5 bar). In general, standard pressure is employed.

Process step (I-A)+(III-A) or (III-B) or (III-C) or (III-D) →(I-C) is effected in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. Preference is given to acetonitrile.

Optionally, the reaction (I-A)+(III-A) or (III-B) or (III-C) or (III-D)→(I-C) can be effected in the presence of a suitable palladium and/or copper catalyst. A suitable palladium catalyst is, for example, palladium on activated carbon, palladium (II) acetate, tetrakis(triphenylphosphine)palladium(0), bis (triphenylphosphine)palladium(II) chloride, bis(acetonitrile) palladium(II) chloride and [1,1'-bis(diphenylphosphino) ferrocene]dichloropalladium(II) and the corresponding dichloromethane complex, optionally in conjunction with additional phosphine ligands, for example (2-biphenyl)di-tert-butylphosphine, dicyclohexyl[2',4',6'-tris(1-methylethyl)biphenyl-2-yl]phosphine (XPHOS), bis(2-phenylphosphinophenyl)ether (DPEphos) or 4,5-bis (diphenylphosphino)-9,9-dimethylxanthene (Xantphos) [cf., for example, Hassan J. et al., Chem. Rev. 102, 1359-1469 (2002)]. Suitable copper catalysts are, for example, copper bronze, copper(I) oxide, copper(I) iodide or copper(I) bromide.

The conversion (I-A)+(III-A) or (III-B) or (III-C) or (III-D)→(I-C) is effected in the presence of a suitable base. Suitable bases for this conversion are the customary inorganic or organic bases. These preferably include alkali metal hydroxides, for example lithium, sodium or potassium hydroxide, alkali metal or alkaline earth metal carbonates such as lithium, sodium, potassium, calcium or caesium carbonate, alkali metal alkoxides such as sodium or potassium methoxide, sodium or potassium ethoxide or sodium or potassium tert-butoxide, alkali metal hydrides such as sodium or potassium hydride, amides such as sodium amide, lithium, sodium or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using sodium hydride or caesium carbonate.

The reaction (I-A)+(III-A) or (III-B) or (III-C) or (III-D)→ (I-C) is performed generally within a temperature range from 0° C. to +200° C., preferably at +10° C. to +150° C. The conversion can be effected at standard, elevated or reduced pressure (for example from 0.5 to 5 bar). In general, standard pressure is employed.

If the $R^{3,4}$ radical is unsaturated, it can subsequently be fully or partly saturated. The reduction is effected with hydrogen in conjunction with transition metal catalysts, for example palladium (10% on activated carbon), Raney nickel or palladium hydroxide. The reduction is effected generally within a temperature range from +20° C. to +50° C. The conversion can be performed at standard or elevated pressure (for example in the range from 1 to 150 bar). In general, 80 to 100 bar are employed.

The conversion (VI)→(VII) can be effected in a solvent which is inert under the reaction conditions or without solvent. A preferred solvent is sulpholane.

The reaction (VI)→(VII) is effected generally within a temperature range from +70° C. to +150° C., preferably from +80° C. to +130° C., optionally in a microwave. The conversion can be performed at standard or elevated pressure (for example in the range from 0.5 to 5 bar). In general, standard pressure is employed.

Especially preferably, the conversion (VI)→(VII) is effected without solvent within a temperature range from 0° C. to +50° C. at standard pressure.

Process step (VII)→(VIII) is effected in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine, acetonitrile or else water. It is equally possible to use mixtures of the solvents mentioned. Preference is given to acetonitrile.

The reaction (VII)→(VIII) is effected generally within a temperature range from +20° C. to +100° C., preferably from +40° C. to +70° C., optionally in a microwave. The conversion can be performed at standard or elevated pressure (for example in the range from 0.5 to 5 bar). In general, standard pressure is employed.

The cyclization (VIII)→(I-D) is effected in a solvent which is inert under the reaction conditions, for example alcohols such as methanol, ethanol, n-propanol, isopropanol, n-butanol or tert-butanol, ethers such as diethyl ether, dioxane, dimethoxyethane, tetrahydrofuran (THF), glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine, acetonitrile or sulpholane. It is equally possible to use mixtures of the solvents mentioned. Preference is given to THF.

Suitable bases for the process step (VIII)→(I-D) are alkali metal hydroxides, for example lithium hydroxide, sodium hydroxide or potassium hydroxide, alkali metal carbonates such as lithium carbonate, sodium carbonate, potassium carbonate or caesium carbonate, alkali metal hydrogencarbonates such as sodium hydrogencarbonate or potassium hydrogencarbonate, alkali metal alkoxides such as sodium methoxide or potassium methoxide, sodium ethoxide or potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to potassium tert-butoxide.

The reaction (VIII)→(I-D) is effected generally within a temperature range from 0° C. to +50° C., preferably from +10° C. to +30° C., optionally in a microwave. The conversion can be performed at standard or elevated pressure (for example in the range from 0.5 to 5 bar). In general, standard pressure is employed.

The cyclization to give (I-D) is preferably effected directly in the course of the conversion (VII)→(VIII) without addition of further reagents.

In an alternative procedure for process [D], the conversion (IV)+(V)→(VI)→(VII)→(VIII)→(I-D) can be performed without isolation of the intermediates.

The conversions (VI)→(VII)→(VIII)→(I-D) are preferably effected without isolation of the intermediates.

Inert solvents for the process step (IV)+(V)→(VI) are, for example, alcohols such as methanol, ethanol, n-propanol, isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is equally possible to use mixtures of the solvents mentioned. Preference is given to methanol or ethanol.

The reaction (IV)+(V)→(VI) is effected generally within a temperature range from +50° C. to +120° C., preferably from +50° C. to +100° C., optionally in a microwave. The conversion can be performed at standard or elevated pressure (for example in the range from 0.5 to 5 bar). In general, standard pressure is employed.

Process step (X)+(XI)→(XII) is effected in a solvent which is inert under the reaction conditions. Suitable solvents are, for example, ethers such as diethyl ether, dioxane, tetrahydrofuran, glycol dimethyl ether or diethylene glycol dimethyl ether, or other solvents such as dimethylformamide (DMF), dimethyl sulphoxide (DMSO), N,N'-dimethylpropyleneurea (DMPU), N-methylpyrrolidone (NMP), pyridine or acetonitrile. It is equally possible to use mixtures of the solvents mentioned. Preference is given to NMP.

The conversion (X)+(XI)→(XII) is effected in the presence of a suitable base. Suitable bases for this conversion are the customary inorganic or organic bases. These preferably include alkali metal hydroxides, for example lithium, sodium or potassium hydroxide, alkali metal or alkaline earth metal carbonates such as lithium, sodium, potassium, calcium or caesium carbonate, alkali metal alkoxides such as sodium or potassium methoxide, sodium or potassium ethoxide or sodium or potassium tert-butoxide, alkali metal hydrides such as sodium or potassium hydride. Preference is given to using sodium hydride.

The reaction (X)+(XI)→(XII) is generally performed within a temperature range from +20° C. to +150° C., preferably at +40° C. to +100° C. The conversion can be effected at standard, elevated or reduced pressure (for example from 0.5 to 5 bar). In general, standard pressure is employed.

The protecting group $PG^1$ is detached by methods known to those skilled in the art; see, for example, T. W. Greene and P. G. M. Wuts, *Protective Groups in Organic Synthesis*, Wiley, New York, 1999.

In an alternative process variant, process step (X)+(XI) can also be effected without a protecting group PG1; the conversion is effected here, preferably without base, in NMP at 80° C. to 100° C.

The preparation processes described can be illustrated by way of example by the following synthesis schemes (Schemes 1 to 4):

Scheme 1
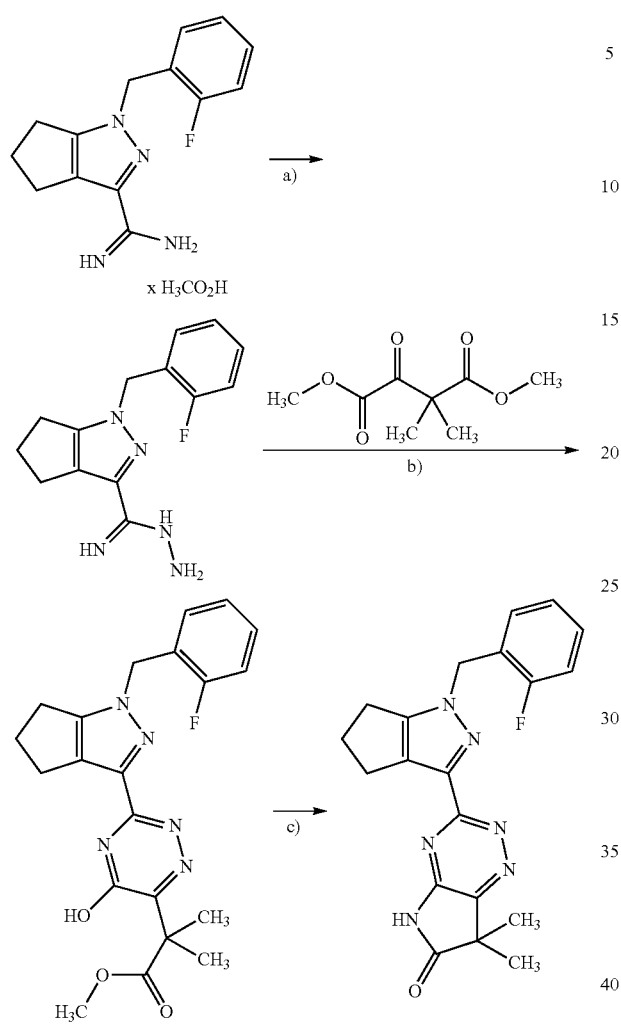
[a): hydrazine hydrate, NEt₃, EtOH b): EtOH c): 1. POCl₃; 2. conc. NH₃, acetonitrile].
Scheme 2
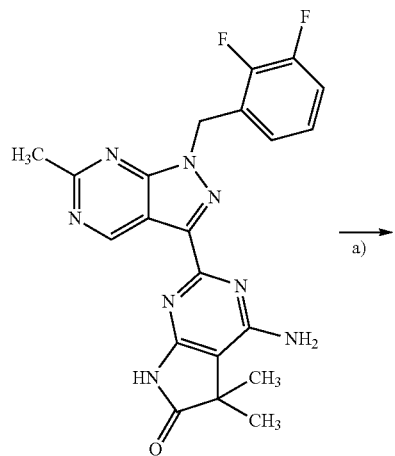
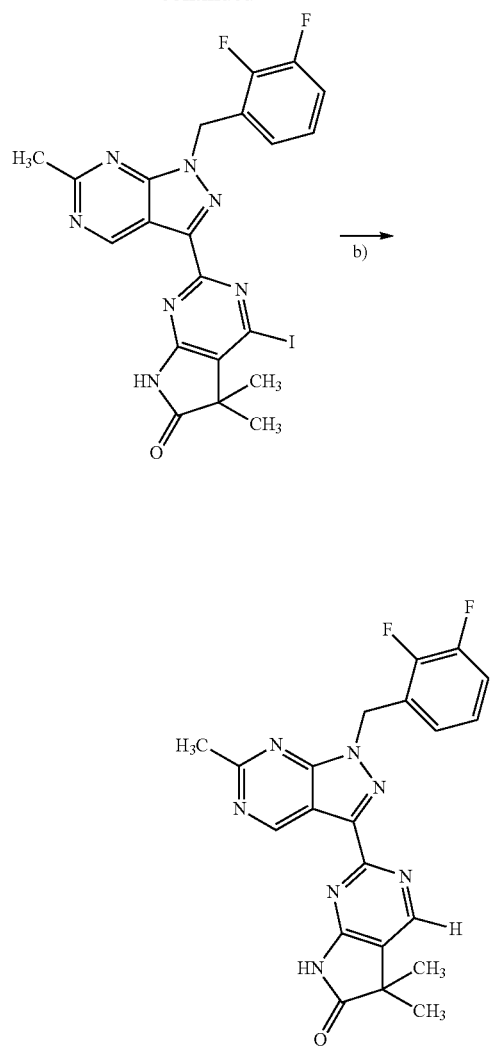
[a): diiodomethane, isopentyl nitrite; b): Pd/C, hydrogen, DMF].
Scheme 3
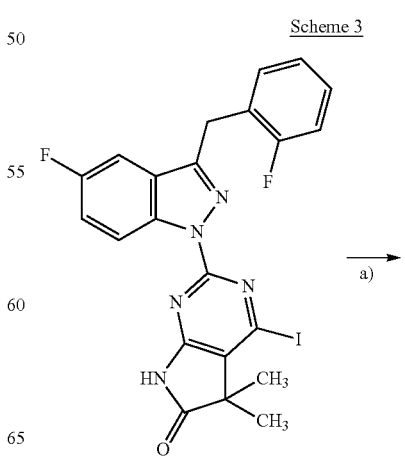

-continued

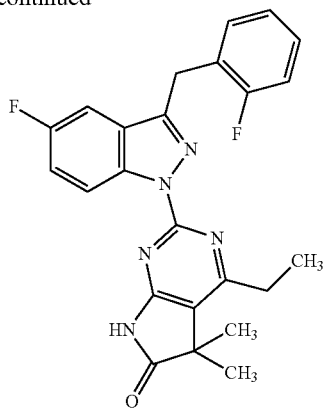

[a]: diethylzinc, PdCl$_2$(dppf), dioxane, 90° C.].

Further inventive compounds can optionally also be prepared by conversions of functional groups of individual substituents, especially those listed for L and R$^3$, proceeding from compounds of the formula (I) obtained by above processes. These conversions are performed by customary methods known to those skilled in the art and include, for example, reactions such as nucleophilic and electrophilic substitutions, oxidations, reductions, hydrogenations, transition metal-catalysed coupling reactions, eliminations, alkylation, amination, esterification, ester cleavage, etherification, ether cleavage, formation of carbonamides, and introduction and removal of temporary protecting groups.

The compounds of the formula (H) are known from the literature (see, for example, WO 2010/065275, WO 2011/115804 and WO 2011/149921) or can be prepared in analogy to processes known from the literature.

The compounds of the formula (IV) can be prepared by reacting a compound of the formula (IX)

Scheme 4

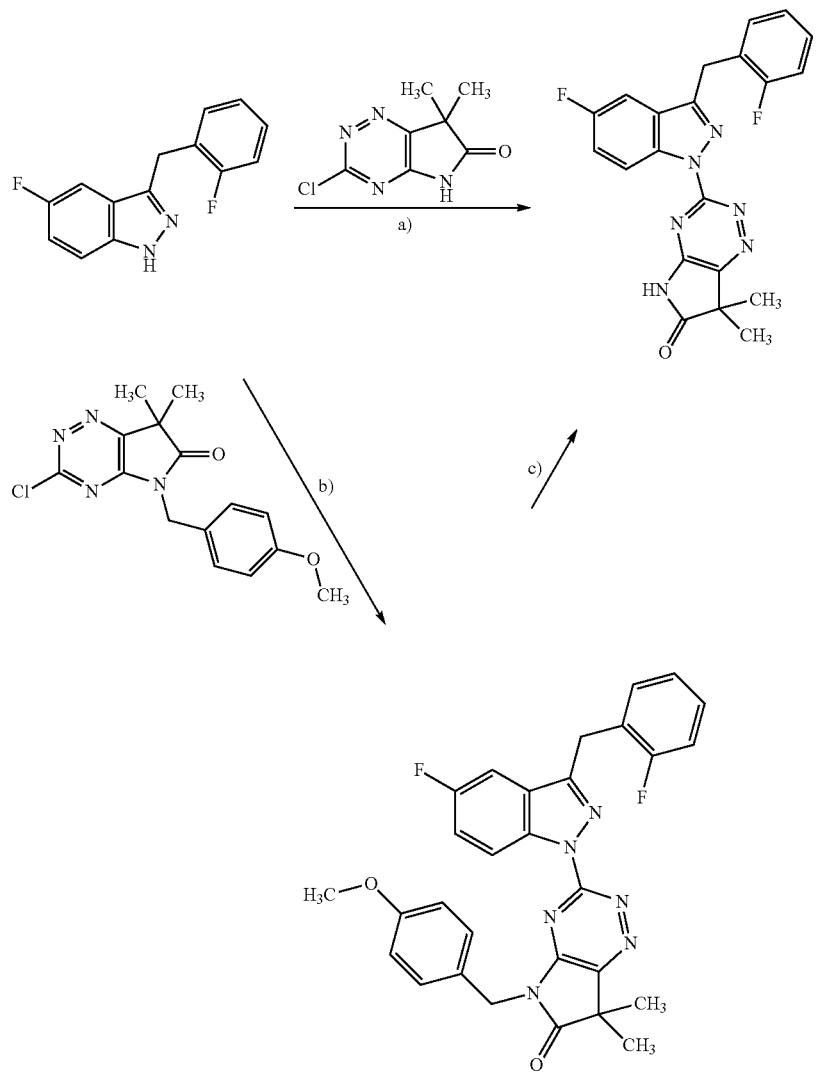

[a): NMP, 80° C.-100° C., b): NaH, NMP, RT-80° C., c): ammonium cerium(IV) nitrate, acetonitrile, water, 0° C.-RT]

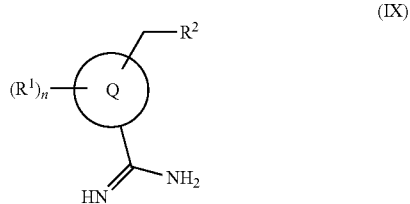

in which n, Q, R¹ and R² are each as defined above
with hydrazine hydrate in an inert solvent in the presence of a suitable base.

Inert solvents for the process step (IX)→(IV) are, for example, alcohols such as methanol, ethanol, n-propanol, potassium ethoxide or potassium tert-butoxide, or organic amines such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to triethylamine.

The reaction (IX)→(IV) is effected generally within a temperature range from 0° C. to +60° C., preferably from +10° C. to +30° C. The conversion can be performed at standard or elevated pressure (for example in the range from 0.5 to 5 bar). In general, standard pressure is employed.

The compounds of the formula (XI) can be prepared as described in the present Experimental for Examples 44A to 48A and in analogy thereto. The following scheme, Scheme 5, illustrates the preparation by way of example:

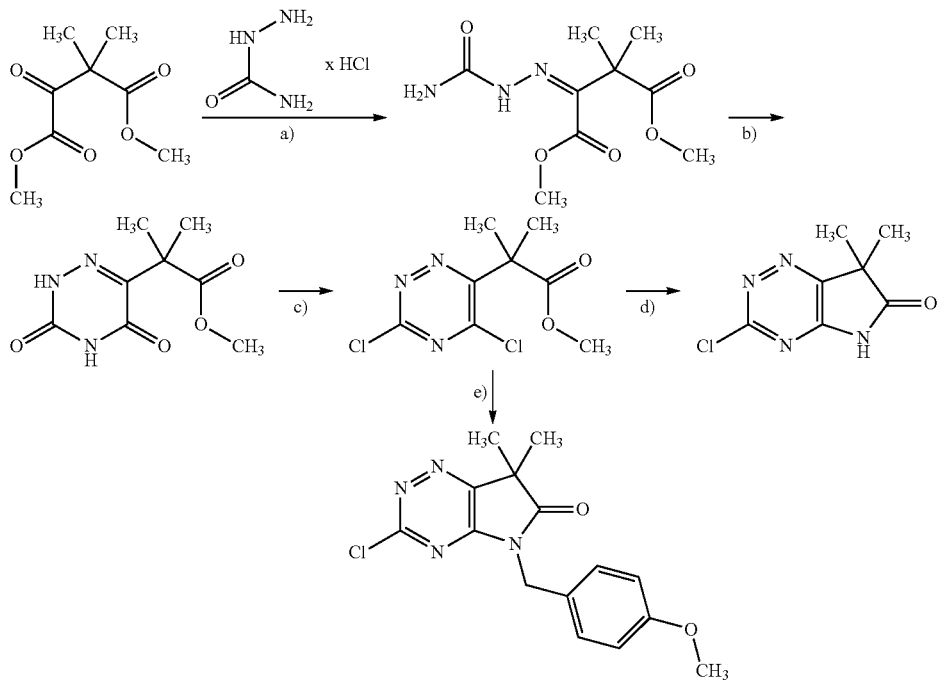

[a]: NaOAc, water, RT: b): NaOMe, MeOH, reflux: c): POCl₃, DMF, reflux; d): aq. ammonia, dioxane, RT; e): 4-methoxybenzylamine, diisopropylethylamine, THF, 0° C.-RT].

isopropanol, n-butanol or tert-butanol, ethers such as diethyl ether, dioxane, dimethoxyethane, tetrahydrofuran, glycol dimethyl ether or diethylene glycol dimethyl ether, hydrocarbons such as benzene, xylene, toluene, hexane, cyclohexane or mineral oil fractions, or other solvents such as dimethylformamide (DMF), dimethyl sulphoxide (DMSO), N,N'-dimethylpropyleneurea (DMPU), N-methylpyrrolidone (NMP), pyridine or acetonitrile. It is equally possible to use mixtures of the solvents mentioned. Preference is given to ethanol.

Suitable bases for the process step (IX)→(IV) are alkali metal hydroxides, for example lithium hydroxide, sodium hydroxide or potassium hydroxide, alkali metal carbonates such as lithium carbonate, sodium carbonate, potassium carbonate or caesium carbonate, alkali metal hydrogencarbonates such as sodium hydrogencarbonate or potassium hydrogencarbonate, alkali metal alkoxides such as sodium methoxide or potassium methoxide, sodium ethoxide or The compounds of the formulae (III-A), (III-B), (III-C), (V) and (IX) are commercially available, are known from the literature (cf., for example, WO 2010/065275, WO 2011/115804 and WO 2011/149921) or can be prepared in analogy to processes known from the literature.

The inventive compounds act as potent stimulators of soluble guanylate cyclase and inhibitors of phosphodiesterase-5, have valuable pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in man and animals.

The inventive compounds cause vasorelaxation and inhibition of platelet aggregation, and lead to a decrease in blood pressure and to a rise in coronary blood flow. These effects are mediated via direct stimulation of soluble guanylate cyclase and intracellular cGMP increase. In addition, the inventive compounds enhance the action of substances which increase the cGMP level, for example EDRF (endothelium-derived relaxing factor), NO donors, protoporphyrin IX, arachidonic acid or phenylhydrazine derivatives.

The inventive compounds are suitable for treatment and/or prophylaxis of cardiovascular, pulmonary, thromboembolic and fibrotic disorders.

The inventive compounds can therefore be used in medicaments for treatment and/or prophylaxis of cardiovascular disorders, for example hypertension, resistant hypertension, acute and chronic heart failure, coronary heart disease, stable and unstable angina pectoris, peripheral and cardiovascular disorders, arrhythmias, atrial and ventricular arrhythmias and impaired conduction, for example atrioventricular grade I-III blocks (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, Sick-Sinus syndrome, syncopes, AV-nodal re-entry tachycardia, Wolff-Parkinson-White syndrome, acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for treatment and/or prophylaxis of thromboembolic disorders and ischaemias such as myocardial ischaemia, myocardial infarction, stroke, cardiac hypertrophy, transient and ischemic attacks, preeclampsia, inflammatory cardiovascular disorders, spasms of the coronary arteries and peripheral arteries, edema formation, for example pulmonary edema, cerebral edema, renal edema or edema caused by heart failure, impaired peripheral perfusion, reperfusion damage, arterial and venous thromboses, microalbuminuria, myocardial insufficiency, endothelial dysfunction, for prevention of restenoses, such as after thrombolysis treatments, percutaneous transluminal angioplasties (PTA), percutaneous transluminal coronary angioplasties (PTCA), heart transplants and bypass operations, and micro- and macrovascular damage (vasculitis), elevated levels of fibrinogen and of low-density LDL, and elevated concentrations of plasminogen activator inhibitor 1 (PAI-1), and for treatment and/or prophylaxis of erectile dysfunction and female sexual dysfunction.

In the context of the present invention, the term "heart failure" also encompasses both acute and chronic forms of heart failure, and also more specific or related types of disease, such as acute decompensated heart failure, right heart failure, left heart failure, global failure, ischemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the inventive compounds can also be used for treatment and/or prophylaxis of arteriosclerosis, disturbed lipid metabolism, hypolipoproteinemias, dyslipideamias, hypertriglyceridemias, hyperlipidemias, hypercholesterolemias, abetalipoproteinemias, sitosterolemia, xanthomatosis, Tangier disease, adiposity, obesity and combined hyperlipidemias, and also of metabolic syndrome.

Moreover, the inventive compounds can be used for treatment and/or prophylaxis of primary and secondary Raynaud's phenomenon, of microcirculation disorders, claudication, peripheral and autonomic neuropathies, diabetic microangiopathies, diabetic retinopathy, diabetic ulcers at the extremities, gangrene, CREST syndrome, erythematosis, onychomycosis, rheumatic disorders, and for promotion of wound healing. The inventive compounds are also suitable for treatment of muscular dystrophy, such as Becker-Kiener muscular dystrophy (BMD) and Duchenne muscular dystrophy (DMD).

Furthermore, the inventive compounds are suitable for treatment of urological disorders, for example benign prostate syndrome (BPS), benign prostate hyperplasia (BPH), benign prostate enlargement (BPE), bladder outlet obstruction (BOO), lower urinary tract syndrome (LUTS, including feline urological syndrome (FUS)), disorders of the urogenital system including neurogenic overactive bladder (OAB) and (IC), incontinence (UI), for example mixed, urge, stress or overflow incontinence (MUI, UUI, SUI, OUI), pelvic pain, benign and malignant disorders of the organs in the male and female urogenital systems.

Furthermore, the inventive compounds are suitable for treatment and/or prophylaxis of renal disorders, especially of acute and chronic renal insufficiency, and of acute and chronic kidney failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilation, hyperphosphataemia and/or need for dialysis. The present invention also encompasses the use of the inventive compounds for treatment and/or prophylaxis of sequelae of renal insufficiency, for example pulmonary edema, heart failure, uremia, anemia, electrolyte disturbances (for example hypercalemia, hyponatremia) and disturbances in bone and carbohydrate metabolism.

Furthermore, the inventive compounds are also suitable for treatment and/or prophylaxis of asthmatic disorders, pulmonary arterial hypertension (PAH) and other forms of pulmonary hypertension (PH) including pulmonary hypertension associated with left heart disease, HIV, sickle cell anemia, thromboembolisms (CTEPH), sarcoidosis, COPD or pulmonary fibrosis, or chronic-obstructive pulmonary disease (COPD), acute respiratory distress syndrome (ARDS), acute lung injury (ALI), alpha-1 antitrypsin deficiency (AATD), pulmonary fibrosis, pulmonary emphysema (for example pulmonary emphysema induced by cigarette smoke) and cystic fibrosis (CF). In addition, the compounds mentioned can be used as bronchodilators.

The compounds described in the present invention are also active ingredients for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the inventive compounds are also suitable for regulation of cerebral blood flow and are thus effective agents for control of migraine. They are also suitable for the prophylaxis and control of sequelae of cerebral infarct (Apoplexia cerebri) such as stroke, cerebral ischaemias and skull-brain trauma. The inventive compounds can likewise be used to control states of pain and tinnitus.

Moreover, the inventive compounds have antiinflammatory action and can therefore be used as antiinflammatories for treatment and/or prophylaxis of sepsis (SIRS), multiple organ failure (MODS, MOF), inflammatory disorders of the kidney, chronic bowel inflammation (IBD, Crohn's Disease, UC), pancreatitis, peritonitis, rheumatoid disorders, inflammatory skin disorders and inflammatory eye disorders.

In addition, the inventive compounds can likewise be used for treatment and/or prophylaxis of autoimmune disorders.

Furthermore, the inventive compounds are suitable for treatment and/or prophylaxis of fibrotic disorders of the internal organs, for example of the lung, of the heart, of the kidneys, of the bone marrow and especially of the liver, and also of dermatological fibroses and fibrotic disorders of the eye. In the context of the present inventions, the term "fibrotic disorders" encompasses especially the following terms: hepatic fibrosis, hepatic cirrhosis, pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, morphea, keloids, hypertrophic scarring (including after surgical interventions), naevi, diabetic retinopathy, proliferative vitreoretinopathy and disorders of the connective tissue (for example sarcoidosis).

Furthermore, the inventive compounds are suitable for control of postoperative scarring, for example resulting from glaucoma operations.

The inventive compounds can likewise be used cosmetically, in the event of ageing and keratinized skin.

Moreover, the inventive compounds are suitable for treatment and/or prophylaxis of hepatitis, neoplasms, osteoporosis, glaucoma and gastroparesis.

The present invention further provides for the use of the inventive compounds for treatment and/or prophylaxis of disorders, especially of the aforementioned disorders.

The present invention further provides for the use of the inventive compounds for treatment and/or prophylaxis of heart failure, angina pectoris, hypertension, pulmonary hypertension, ischaemia, vascular disorders, renal insufficiency, thromboembolic disorders, fibrotic disorders and arteriosclerosis.

The present invention further provides the inventive compounds for use in a method for treatment and/or prophylaxis of heart failure, angina pectoris, hypertension, pulmonary hypertension, ischaemia, vascular disorders, renal insufficiency, thromboembolic disorders, fibrotic disorders and arteriosclerosis.

The present invention further provides for the use of the inventive compounds for production of a medicament for treatment and/or prophylaxis of disorders, especially of the aforementioned disorders.

The present invention further provides for the use of the inventive compounds for production of a medicament for treatment and/or prophylaxis of heart failure, angina pectoris, hypertension, pulmonary hypertension, ischaemia, vascular disorders, renal insufficiency, thromboembolic disorders, fibrotic disorders and arteriosclerosis.

The present invention further provides a method for treatment and/or prophylaxis of disorders, especially of the aforementioned disorders, using an effective amount of at least one of the inventive compounds.

The present invention further provides a method for treatment and/or prophylaxis of heart failure, angina pectoris, hypertension, pulmonary hypertension, ischaemia, vascular disorders, renal insufficiency, thromboembolic disorders, fibrotic disorders and arteriosclerosis using an effective amount of at least one of the inventive compounds.

The inventive compounds can be employed alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable active ingredient combinations include:
- organic nitrates and NO donors, for example sodium nitroprusside, nitroglycerine, isosorbide mononitrate, isosorbide dinitrate, molsidomine or SIN1, and inhaled NO;
- compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;
- antithrombotic agents, by way of example and with preference from the group of the platelet aggregation inhibitors, the anticoagulants or the profibrinolytic substances;
- hypotensive active ingredients, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or
- active ingredients which modify lipid metabolism, by way of example and with preference from the group of the thyroid receptor agonists, cholesterol synthesis inhibitors, by way of example and with preference HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein (a) antagonists.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, preferred examples being aspirin, clopidogrel, ticlopidin or dipyridamol.

In a preferred embodiment of the invention, the inventive compounds are administered in combination with a thrombin inhibitor, by way of example and with preference ximelagatran, dabigatran, melagatran, bivalirudin or clexane.

In a preferred embodiment of the invention, the inventive compounds are administered in combination with a GPIIb/IIIa antagonist, preferred examples being tirofiban or abciximab.

In a preferred embodiment of the invention, the inventive compounds are administered in combination with a factor Xa inhibitor, preferred examples being rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with heparin or a low molecular weight (LMW) heparin derivative.

In a preferred embodiment of the invention, the inventive compounds are administered in combination with a vitamin K antagonist, a preferred example being coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists and the diuretics.

In a preferred embodiment of the invention, the inventive compounds are administered in combination with a calcium antagonist, preferred examples being nifedipine, amlodipine, verapamil or diltiazem.

In a preferred embodiment of the invention, the inventive compounds are administered in combination with an alpha-1 receptor blocker, a preferred example being prazosin.

In a preferred embodiment of the invention, the inventive compounds are administered in combination with a beta receptor blocker, preferred examples being propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embursatan.

In a preferred embodiment of the invention, the inventive compounds are administered in combination with an ACE inhibitor, preferred examples being enalapril, captopril, lisinopril, ramipril, delapril, fosinopril, quinopril, perindopril or trandopril.

In a preferred embodiment of the invention, the inventive compounds are administered in combination with an endothelin antagonist, preferred examples being bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Agents which alter lipid metabolism are preferably understood to mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein (a) antagonists.

In a preferred embodiment of the invention, the inventive compounds are administered in combination with a CETP inhibitor, preferred examples being dalcetrapib, BAY 60-5521, anacetrapib or CETP vaccine (CETi-1).

In a preferred embodiment of the invention, the inventive compounds are administered in combination with a thyroid receptor agonist, preferred examples being D-thyroxin, 3,5,3'-triiodothyronin (T3), CGS 23425 or axitirome (CGS 26214).

In a preferred embodiment of the invention, the inventive compounds are administered in combination with a HMG-CoA reductase inhibitor from the class of the statins, preferred examples being lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, preferred examples being BMS-188494 or TAK-475.

In a preferred embodiment of the invention, the inventive compounds are administered in combination with an ACAT inhibitor, preferred examples being avasimibe, melinamide, pactimibe, eflucimibe or SMP-797.

In a preferred embodiment of the invention, the inventive compounds are administered in combination with an MTP inhibitor, preferred examples being implitapide, BMS-201038, R-103757 or JTT-130.

In a preferred embodiment of the invention, the inventive compounds are administered in combination with a PPAR-gamma agonist, preferred examples being pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, preferred examples being ezetimibe, tiqueside or pamaqueside.

In a preferred embodiment of the invention, the inventive compounds are administered in combination with a lipase inhibitor, a preferred example being orlistat.

In a preferred embodiment of the invention, the inventive compounds are administered in combination with a polymeric bile acid adsorbent, preferred examples being cholestyramine, colestipol, colesolvam, CholestaGel or colestimide.

In a preferred embodiment of the invention, the inventive compounds are administered in combination with a bile acid reabsorption inhibitor, preferred examples being ASBT (=IBAT) inhibitors, for example AZD-7806, S-8921, AK-105, BARI-1741, SC-435 or SC-635

In a preferred embodiment of the invention, the inventive compounds are administered in combination with a lipoprotein(a) antagonist, preferred examples being gemcabene calcium (CI-1027) or nicotinic acid.

The present invention further provides medicaments which comprise at least one inventive compound, typically together with one or more inert nontoxic pharmaceutically suitable excipients, and for the use thereof for the aforementioned purposes.

The inventive compounds can act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

For these administration routes, the inventive compounds can be administered in suitable administration forms.

Suitable administration forms for oral administration are those which work according to the prior art, which release the inventive compounds rapidly and/or in a modified manner and which contain the inventive compounds in crystalline and/or amorphized and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The inventive compounds can be converted to the administration forms listed. This can be accomplished in a manner known per se by mixing with inert nontoxic pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active ingredient, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are percentages by weight unless stated otherwise; parts are parts by weight. Solvent ratios, dilution ratios and concentration figures for liquid/liquid solutions are each based on volume.

A. EXAMPLES

Abbreviations and Acronyms aq. aqueous solution
calc. calculated
br s broad singlet (in NMR)
DCI direct chemical ionization (in MS)
DMF dimethylformamide
DMSO dimethyl sulphoxide
eq. equivalent(s)
ESI electrospray ionization (in MS)
Et ethyl
h hour(s)
HPLC high-pressure high-performance liquid chromatography
HRMS high-resolution mass spectrometry
conc. concentrated
LC-MS liquid chromatography-coupled mass spectrometry
Me methyl
min minute(s)
MS mass spectrometry
NMR nuclear magnetic resonance spectrometry
$PdCl_2(dppf) \times CH_2Cl_2$ [1,1'-bis(diphenylphosphine)ferrocene]dichloropalladium(II)-dichloromethane complex
Ph phenyl
RT room temperature
$R_t$ retention time (in HPLC)
THF tetrahydrofuran
UV ultraviolet spectrometry
v/v volume to volume ratio (of a solution)

LC/MS Methods

Method 1:
Instrument: Waters ACQUITY SQD UPLC System; column: Waters Acquity UPLC HSS T3 1.8μ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2:
Instrument: Waters ACQUITY SQD UPLC System; column: Waters Acquity UPLC HSS T3 1.8μ 30×2 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.60 ml/min; UV detection: 208-400 nm.

Method 3:

Instrument: Micromass Quattro Premier with Waters UPLC Acquity; column: Thermo Hypersil GOLD 1.9μ 50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4:

MS instrument type: Waters (Micromass) Quattro Micro; HPLC instrument type: Agilent 1100 Series; column: Thermo Hypersil GOLD 3μ 20×4 mm; eluent A: 1 l water+0.5 ml 50% formic acid, eluent B: 1 l acetonitrile+0.5 ml 50% formic acid; gradient: 0.0 min 100% A→3.0 min 10% A→4.0 min 10% A; oven: 50° C.; flow rate: 2 ml/min; UV detection: 210 nm Starting Compounds and Intermediates Example 1A 5-Chloro-3-(2,3,6-trifluorobenzyl)-1H-indazole-1-carboximidamide

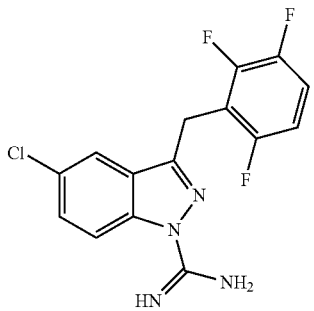 [SMILES: N=C(N)n1nc(Cc2c(F)ccc(F)c2F)c2cc(Cl)ccc21]

4.60 g (10.96 mmol) of 2-[1-(2-bromo-5-chlorophenyl)-2-(2,3,6-trifluorophenyl)ethylidene]hydrazinecarboximidamide (the synthesis of this compound is described in WO 2010/065275, Example 3, Step B, page 36-37) and 2.09 g (10.96 mmol) of copper(I) iodide were initially charged in NMP (150 ml) in a 1 l round-bottom flask, and then stirred in an oil bath preheated to 170° C. for 14 minutes. The reaction mixture was subsequently cooled in an ice bath and admixed with an ice/water mixture (400 ml), and concentrated aqueous ammonia solution (200 ml) was added. After stirring for 15 minutes, the solids were filtered off with suction. The residue was dissolved in ethyl acetate, washed twice with water and dried, and the solvent was removed on a rotary evaporator. 3.00 g (39% of theory, 49% purity) of the title compound were obtained. The crude product was reacted further without purification.

LC-MS (Method 1): $R_t$=0.80 min; MS (ESIpos): m/z=339 (M+H)$^+$

Example 2A

Methyl 3,3-dicyano-2,2-dimethylpropanoate

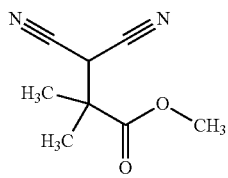

In THF (91 ml), 1.816 g (45.411 mmol) of sodium hydride (60% in mineral oil) were admixed gradually with 3 g (45.411 mmol) of malononitrile. Subsequently, 5.876 ml (45.411 mmol) of methyl 2-bromo-2-methylpropanoate were added and the reaction mixture was stirred at room temperature overnight. Thereafter, another 5.876 ml (45.411 mmol) of methyl 2-bromo-2-methylpropanoate were added and the reaction mixture was heated to 50° C. overnight. Then yet another 1.762 ml (13.623 mmol) of methyl 2-bromo-2-methylpropanoate were added and the reaction mixture was heated to 50° C. for a further 4 h. The mixture was then admixed with saturated aqueous sodium hydrogencarbonate solution and extracted three times with ethyl acetate. The combined organic phases were washed with saturated aqueous sodium chloride solution, dried over sodium sulphate, filtered and concentrated to dryness. This gave 8.9 g of crude product, which was purified by chromatography on silica gel (4:1 cyclohexane-ethyl acetate).

Yield: 6.47 g (85% of theory)

$^1$H NMR (400 MHz, DMSO-d$_6$): δ [ppm]=1.40 (s, 6H), 3.74 (s, 3H), 5.27 (s, 1H).

Example 3A

4-Amino-2-[5-chloro-3-(2,3,6-trifluorobenzyl)-1H-indazol-1-yl]-5,5-dimethyl-5,7-dihydro-6H-pyrrolo[2,3-d]pyrimidin-6-one

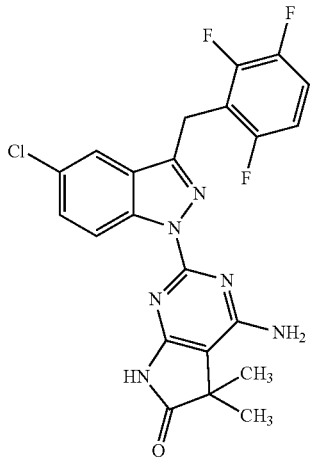 [SMILES: CC1(C)C(=O)Nc2nc(-n3nc(Cc4c(F)ccc(F)c4F)c4cc(Cl)ccc43)nc(N)c21]

350 mg (0.52 mmol, 49% purity) of the crude product from Example 1A and 301 mg (1.81 mmol) of Example 2A were initially charged in tert-butanol (2.3 ml), and 98.6 mg (0.88 mmol) of potassium tert-butoxide were added. The reaction mixture was heated to reflux for 18 h. After cooling, the reaction mixture was diluted with ethyl acetate and washed with approx. 7% aqueous ammonium chloride solution. The organic phase was dried and the solvent was removed on a rotary evaporator. The residue was purified by chromatography on 150 ml of silica gel with 1:1 cyclohexane/ethyl acetate. 120 mg (38% of theory) of the title compound were obtained.

LC-MS (Method 2): $R_t$=1.14 min; MS (ESIpos): m/z=473 (M+H)$^+$ $^1$H NMR (400 MHz, DMSO-d$_6$): δ [ppm]=1.34 (s, 6H), 4.46 (s, 2H), 7.00 (br. s., 2H), 7.16-7.25 (m, 1H), 7.42-7.51 (m, 1H), 7.51-7.58 (m, 1H), 7.90-7.94 (m, 1H), 8.83 (d, 1H), 11.10 (s, 1H).

Example 4A 1-(2-Bromophenyl)-2-(2-fluorophenyl)ethanone

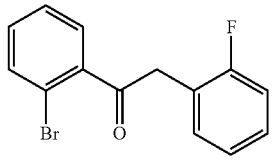 [SMILES: O=C(Cc1ccccc1F)c1ccccc1Br]

15.0 g (69.8 mmol) of methyl 2-bromobenzoate and 11.8 g (76.7 mmol) of 2-fluorophenylacetic acid were initially charged at −70° C. under an argon atmosphere in THF (278 ml), and 174 ml of a 1M solution of sodium hexamethyldisilazane in THF were added dropwise over 20 min. The reaction mixture was warmed to 0° C. and stirred at this temperature for 30 min, and 1N hydrochloric acid (278 ml) was added. After stirring vigorously with evolution of gas ($CO_2$ elimination) for 1 h, the reaction mixture was extracted with ethyl acetate (500 ml). The organic phase was washed twice with saturated sodium hydrogencarbonate solution, once with water and once with saturated aqueous sodium chloride solution. After drying and removal of the solvent on a rotary evaporator, 16.8 g of residue (55% purity) were obtained. The residue was dissolved in THF (140 ml), 1N sodium hydroxide solution (70 ml) was added and the mixture was stirred at RT for 4 h, in order to hydrolyse excess ester. The THF was removed on a rotary evaporator, and the aqueous phase was extracted with diethyl ether and the organic phase was washed with saturated sodium hydrogencarbonate solution and saturated aqueous sodium chloride solution. After drying and removal of the solvent, 12.2 g of residue were obtained (approx. 80% purity). The residue was dissolved in THF (100 ml), 1N sodium hydroxide solution (40 ml) was added and the mixture was stirred at RT overnight. The THF was removed on a rotary evaporator, and the aqueous phase was extracted with diethyl ether and the organic phase was washed with saturated sodium hydrogencarbonate solution and saturated aqueous sodium chloride solution. After drying and removal of the solvent, 7.90 g (37% of theory) of the title compound were isolated.

$^1$H NMR (400 MHz, DMSO-$d_6$): δ [ppm]=4.35 (s, 2H), 7.14-7.22 (m, 2H), 7.30-7.39 (m, 2H), 7.41-7.47 (m, 1H), 7.49-7.55 (m, 1H), 7.70-7.78 (m, 2H).

Example 5A

2-[1-(2-Bromophenyl)-2-(2-fluorophenyl)ethylidene]hydrazinecarboximidamide

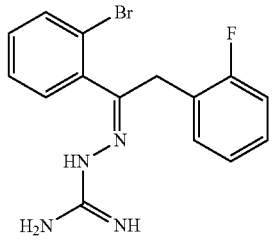 [SMILES: N=C(N)N/N=C(/Cc1ccccc1F)c1ccccc1Br]

7.80 g (26.6 mmol) of Example 4A and 5.88 g (53.2 mmol) of aminoguanidine hydrochloride were initially charged in ethylene glycol (193 ml), and 8.50 g (59.9 mmol) of boron trifluoride-diethyl ether complex were added. The reaction mixture was heated at 120° C. for 2 h using a distillation apparatus. After cooling, another 5.88 g (53.2 mmol) of aminoguanidine hydrochloride and 8.50 g (59.9 mmol) of boron trifluoride-diethyl ether complex were added and the mixture was stirred at 120° C. for 3 h. After cooling, water (750 ml) was added and 1N sodium hydroxide solution was used to set a pH of 11-12. After onset of crystal formation, 300 g of ice were added, the mixture was stirred for 5 min and then the solids were filtered off. The residue was washed first with water, then with pentane, and dried under reduced pressure. 8.30 g (87% of theory) of the title compound were obtained.

LC-MS (Method 1): $R_t$=0.78 min; MS (ESIpos): m/z (Br isotope 1+2)=349+351 (M+H)$^+$

Example 6A 3-(2-Fluorobenzyl)-1H-indazole-1-carboximidamide

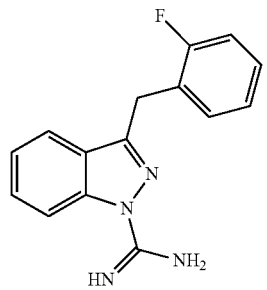 [SMILES: N=C(N)n1nc(Cc2ccccc2F)c2ccccc21]

320 ml of N-methylpyrrolidone were heated to 140° C., 8.20 g (23.5 mmol) of Example 5A and 4.47 g (23.5 mmol) copper(I) iodide were added and the mixture was stirred at bath temperature 170° for 14 min. The reaction mixture was then added gradually to 1 l of ice-water, and concentrated aqueous ammonia solution (350 ml) was added. After stirring for 5 minutes, 1 l of ethyl acetate was added and the mixture was stirred for 10 min. The aqueous phase was extracted once with ethyl acetate and the combined organic phases were washed three times with water. After drying and removal of the solvent on a rotary evaporator, 7.10 g (74% of theory, 66% purity) of the title compound were obtained. The crude product was reacted further without purification.

LC-MS (Method 1): $R_t$=0.68 min; MS (ESIpos): m/z=269 (M+H)$^+$

Example 7A

4-Amino-2-[3-(2-fluorobenzyl)-1H-indazol-1-yl]-5,5-dimethyl-5,7-dihydro-6H-pyrrolo[2,3-d]pyrimidin-6-one

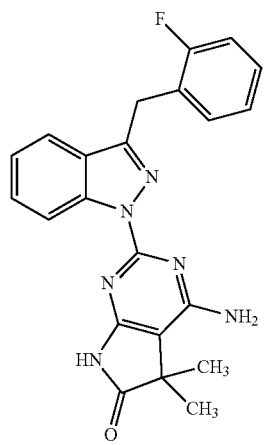 [SMILES: CC1(C)C(=O)Nc2nc(-n3nc(Cc4ccccc4F)c4ccccc43)nc(N)c21]

7.00 g (17.2 mmol, 66% purity) of the crude product from Example 6A and 5.72 g (34.4 mmol) of Example 2A were initially charged in tert-butanol (77.0 ml), and 3.29 g (29.3 mmol) of potassium tert-butoxide were added. The reaction mixture was heated to reflux for 18 h. After cooling, the reaction mixture was diluted with ethyl acetate and washed with approx. 7% aqueous ammonium chloride solution. The organic phase was washed with saturated aqueous sodium chloride solution and dried, and the solvent was removed on a rotary evaporator. The residue was purified by chromatography on 600 ml of silica gel with 2:3 cyclohexane/ethyl acetate. 2.20 g (29% of theory) of the title compound were obtained in solid form.

LC-MS (Method 3): $R_t$=2.19 min; MS (ESIpos): m/z=403 (M+H)$^+$ $^1$H NMR (400 MHz, DMSO-$d_6$): δ [ppm]=1.35 (s, 6H), 4.39 (s, 2H), 6.97 (br. s., 2H), 7.11-7.18 (m, 1H), 7.21 (d, 1H), 7.24-7.33 (m, 2H), 7.36 (t, 1H), 7.50 (t, 1H), 7.70 (d, 1H), 8.82 (d, 1H), 11.10 (s, 1H).

Example 8A 1-(2-Bromo-5-fluorophenyl)-2-(2-fluorophenyl)ethanone

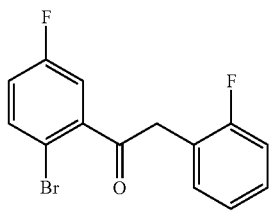 [SMILES: O=C(Cc1ccccc1F)c1cc(F)ccc1Br]

15.0 g (63.1 mmol) of methyl 2-bromo-5-fluorobenzoate and 11.7 g (75.7 mmol) of 2-fluorophenylacetic acid were initially charged at −70° C. under an argon atmosphere in THF (278 ml), and a 1M solution of sodium hexamethyldisilazane in THF (158 ml) was added dropwise over 20 min. The reaction mixture was stirred at this temperature for 30 min, warmed to 0° C. and stirred at 0° C. for a further 30 min, and then 1N hydrochloric acid (251 ml) was added. After stirring vigorously with evolution of gas (CO$_2$ elimination) for 1 h, the reaction mixture was extracted with ethyl acetate (700 ml). The organic phase was washed twice with saturated aqueous sodium hydrogencarbonate solution, once with water and once with saturated aqueous sodium chloride solution. After drying and removal of the solvent on a rotary evaporator, 16.9 g of residue were obtained (50% purity). The residue was dissolved in THF (200 ml), 1N sodium hydroxide solution (100 ml) was added and the mixture was stirred at RT overnight. The THF was removed on a rotary evaporator, and the aqueous phase was extracted with diethyl ether and the organic phase was washed with saturated aqueous sodium hydrogencarbonate solution and saturated aqueous sodium chloride solution. After drying and removal of the solvent on a rotary evaporator, 9.10 g (42% of theory) of the title compound were isolated in solid form.

$^1$H NMR (400 MHz, DMSO-$d_6$): δ [ppm]=4.36 (s, 2H), 7.14-7.24 (m, 2H), 7.30-7.39 (m, 3H), 7.71-7.80 (m, 2H).

Example 9A

2-[1-(2-Bromo-5-fluorophenyl)-2-(2-fluorophenyl)ethylidene]hydrazinecarboximidamide

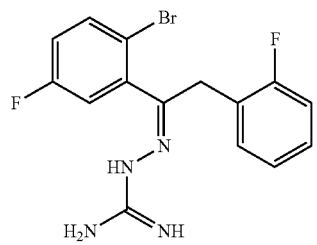 [SMILES: N=C(N)N/N=C(/Cc1ccccc1F)c1cc(F)ccc1Br]

9.00 g (28.9 mmol) of Example 8A and 6.40 g (58.9 mmol) of aminoguanidine hydrochloride were initially charged in ethylene glycol (207 ml), and 9.24 g (65.1 mmol) of boron trifluoride-diethyl ether complex were added. The reaction mixture was heated at 120° C. for 2 h using a distillation apparatus. After cooling, another 6.40 g (58.9 mmol) of aminoguanidine hydrochloride and 9.24 g (65.1 mmol) of boron trifluoride-diethyl ether complex were added and the mixture was stirred at 120° C. for 3 h. After cooling, the reaction mixture was added gradually to water (800 ml), and 1N sodium hydroxide solution was used to set a pH of 11-12. After onset of precipitate formation, 300 g of ice were added and the mixture was stirred for 15 min. Owing to the tackiness of the precipitate, the water was decanted off and the residue was extracted by stirring twice more with 200 ml of water each time. The tacky precipitate was dissolved in diethyl ether and washed with water, the organic phase was dried, the solvent was removed on a rotary evaporator and 6.00 g (54% of theory) of the title compound were isolated as a foam.

LC-MS (Method 1): $R_t$=0.80 min; MS (ESIpos): m/z=367+369 (M+H)$^+$

Example 10A

5-Fluoro-3-(2-fluorobenzyl)-1H-indazole-1-carboximidamide

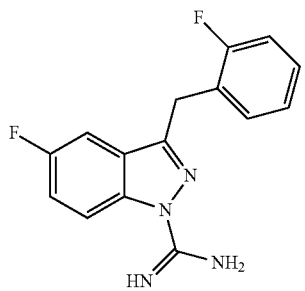 [SMILES: N=C(N)n1nc(Cc2ccccc2F)c2cc(F)ccc21]

222 ml of N-methylpyrrolidone were heated to 140° C., 6.00 g (16.3 mmol) of Example 9A and 3.11 g (16.3 mmol) copper(I) iodide were added and the mixture was stirred at bath temperature 170° C. for 14 min. The reaction mixture was then added gradually to 700 ml of ice-water, and concentrated aqueous ammonia solution (230 ml) was added. After stirring for 5 minutes, 700 ml of ethyl acetate was added and the mixture was stirred for 10 min. The aqueous phase was extracted once more with ethyl acetate and the combined organic phases were washed three times with water. After drying and removal of the solvent on a rotary evaporator, 6.00 g (64% of theory, 50% purity) of the product were obtained. The crude product was reacted further without purification.

LC-MS (Method 3): $R_t$=1.60 min; MS (ESIpos): m/z=287 (M+H)$^+$

Example 11A

4-Amino-2-[5-fluoro-3-(2-fluorobenzyl)-1H-indazol-1-yl]-5,5-dimethyl-5,7-dihydro-6H-pyrrolo[2,3-d]pyrimidin-6-one

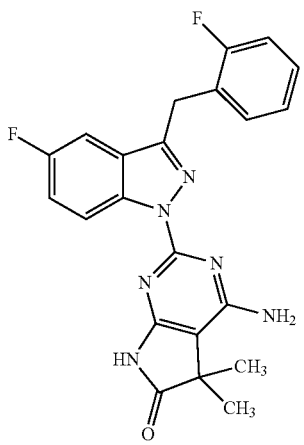 [SMILES: CC1(C)C(=O)Nc2nc(-n3nc(Cc4ccccc4F)c4cc(F)ccc43)nc(N)c21]

6.00 g (approx. 10.5 mmol, 50% purity) of the crude product from Example 10A and 5.22 g (31.4 mmol) of Example 2A were initially charged in tert-butanol (46.0 ml), and 2.00 g (17.8 mmol) of potassium tert-butoxide were added. The reaction mixture was heated to reflux for 18 h. After cooling, the mixture was diluted with ethyl acetate and extracted with approx. 7% aqueous ammonium chloride solution. The organic phase was washed with saturated aqueous sodium chloride solution and dried, and the solvent was removed on a rotary evaporator. The residue was purified by chromatography on 600 ml of silica gel with 2:3 cyclohexane/ethyl acetate. The product-containing fractions were concentrated and stirred with approx. 20 ml of diethyl ether, filtered with suction and washed with diethyl ether. 1.80 g (37% of theory) of the title compound were obtained in solid form.

LC-MS (Method 1): $R_t$=1.00 min; MS (ESIpos): m/z=421 (M+H)$^+$

Example 12A 3,5-Difluoropyridine-2-carbonyl chloride

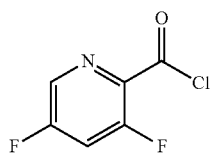 [SMILES: O=C(Cl)c1ncc(F)cc1F]

A suspension of 5.00 g (31.4 mmol) of 3,5-difluoropyridine-2-carboxylic acid in thionyl chloride (21 ml) was heated to reflux for 5 h. The solution was concentrated, and the residue was twice taken up in a little toluene and concentrated again. This gave 3.80 g of a solid, which was converted further directly without further purification.

Example 13A

Methyl 3-(3,5-difluoropyridin-2-yl)-2-(2-fluorophenyl)-3-oxopropanoate

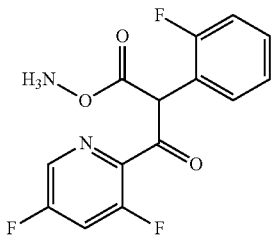 [SMILES: NOC(=O)C(C(=O)c1ncc(F)cc1F)c1ccccc1F]

21.4 ml (21.4 mmol) of lithium hexamethyldisilazide (1.0 M in THF) were initially charged in THF (30 ml) under argon and a solution of 3.00 g (17.8 mmol) of methyl 2-fluorophenylacetate in THF (15 ml) was added dropwise at −78° C. The reaction mixture was stirred at −78° C. for 1 h, and then a solution of 3.80 g (21.4 mmol) of the compound from Example 12A in THF (15 ml) was added dropwise. The solution was stirred at −78° C. for 1 h, then brought to RT, and saturated aqueous ammonium chloride solution was added in portions. The mixture was diluted with water and extracted twice with ethyl acetate. The combined organic phases were dried over sodium sulphate, filtered and concentrated. The residue was stirred with MTBE, the solids were filtered off and the filtrate was concentrated. Silica gel chromatography (eluent: 30:1, 20:1 cyclohexane-ethyl acetate) of the residue gave 3.66 g (87% purity, 57% of theory) of the title compound. The crude product was converted without further purification.

LC-MS (Method 1): $R_t$=1.05 min; MS (ESIpos): m/z=310 (M+H)$^+$ $^1$H NMR (400 MHz, DMSO-d$_6$): δ=3.66 (s, 3H), 6.25 (s, 1H), 7.20-7.28 (m, 4H), 7.31-7.38 (m, 1H), 8.15-8.23 (m, 1H), 8.68-8.71 (m, 1H).

Example 14A 1-(3,5-Difluoropyridin-2-yl)-2-(2-fluorophenyl)ethanone

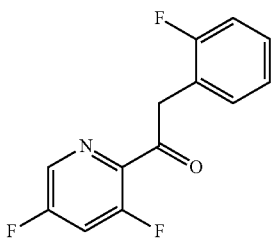 [SMILES: O=C(Cc1ccccc1F)c1ncc(F)cc1F]

11.65 g (37.67 mmol) of the compound from Example 13A were initially charged in DMSO (37 ml). Subsequently, 2.42 g (41.44 mmol) of sodium chloride and water (7 ml) were added, and the mixture was stirred in a microwave at 150° C.

for 30 min. The reaction mixture was diluted with ethyl acetate, and the organic phase was washed three times with water and once with saturated aqueous sodium chloride solution, dried over sodium sulphate, filtered and concentrated. This gave 9.07 g (89%, 85% of theory) of the desired compound in solid form, which was converted without further purification.

LC-MS (Method 1): $R_t$=1.05 min; MS (ESIpos): m/z=252 (M+H)$^+$ $^1$H NMR (400 MHz, DMSO-d$_6$): δ=4.53 (s, 2H), 7.15-7.22 (m, 2H), 7.30-7.37 (m, 2H), 8.11-8.18 (m, 1H), 8.70-8.72 (m, 1H).

Example 15A

6-Fluoro-3-(2-fluorobenzyl)-1H-pyrazolo[4,3-b]pyridine

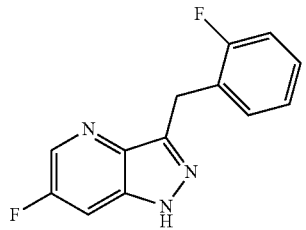 [SMILES: Fc1cnc2c(Cc3ccccc3F)n[nH]c2c1]

9.07 g (32.4 mmol) of the compound from Example 14A were initially charged in pyridine (84 ml). Subsequently, 8.10 g (162 mmol) of hydrazine hydrate and 19.8 mg (0.162 mmol) of 4-dimethylaminopyridine were added, and the mixture was heated to reflux for 30 min. The reaction mixture was diluted with ethyl acetate at RT and washed four times with 10% aqueous citric acid solution. The organic phase was subsequently washed with saturated aqueous sodium chloride solution, dried over sodium sulphate, filtered and concentrated. The residue was admixed with MTBE and the solids were filtered off. The latter were dried under high vacuum and gave 1.79 g (79%, 18% of theory) of the title compound. The filtrate was concentrated and gave a further 4.86 g (61%, 37% of theory) of the title compound. The two fractions were combined and converted without further purification.

LC-MS (Method 4): $R_t$=1.87 min; MS (ESIpos): m/z=246 (M+H)$^+$ $^1$H NMR (400 MHz, DMSO-d$_6$): δ=4.33 (s, 2H), 7.06-7.12 (m, 1H), 7.12-7.19 (m, 1H), 7.22-7.29 (m, 1H), 7.29-7.35 (m, 1H), 7.87 (dd, 1H), 7.84-7.89 (m, 1H), 8.48-8.51 (br. s, 1H).

Example 16A 1,4,5,6-Tetrahydrocyclopenta[c]pyrazole-3-carbonitrile

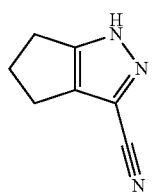

The preparation of the compound is described in: *Org. Process Res. Dev.* 2009, 13, 543.

Example 17A 1-(2-Fluorobenzyl)-1,4,5,6-tetrahydrocyclopenta[c]pyrazole-3-carbonitrile

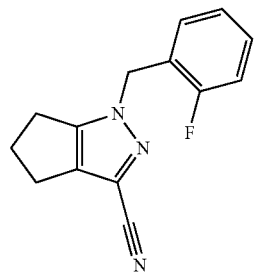 [SMILES: N#Cc1nn(Cc2ccccc2F)c2c1CCC2]

10.320 g (77.50 mmol) of 1,4,5,6-tetrahydrocyclopenta[c]pyrazole-3-carbonitrile were dissolved in 100 ml of DMF, 30.304 g (93.01 mmol) of caesium carbonate and 16.116 g (85.26 mmol) of 2-fluorobenzyl bromide were added, and the mixture was stirred at RT overnight. The mixture was concentrated and taken up in dichloromethane, and water was added. The organic phase was removed and the aqueous phase was extracted twice with dichloromethane. The combined organic phases were washed with saturated aqueous sodium chloride solution, filtered through a silicone filter and concentrated. The residue was purified by flash chromatography on silica gel (eluent: hexane/ethyl acetate, gradient). 11.37 g (60% of theory) of the target compound were obtained.

$^1$H NMR (400 MHz, DMSO-d$_6$): δ [ppm]=2.59-2.64 (m, 4H), 5.33 (s, 2H), 7.15-7.23 (m, 2H), 7.27-7.33 (m, 1H), 7.36-7.43 (m, 1H).

Example 18A 1-(2-Fluorobenzyl)-1,4,5,6-tetrahydrocyclopenta[c]pyrazole-3-carboximidamide

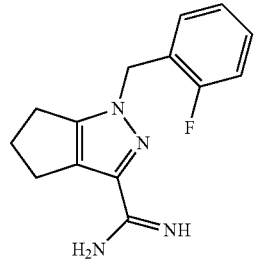 [SMILES: N=C(N)c1nn(Cc2ccccc2F)c2c1CCC2]

Under a nitrogen atmosphere, 3.600 g (14.92 mmol) of 1-(2-fluorobenzyl)-1,4,5,6-tetrahydrocyclopenta[c]pyrazole-3-carbonitrile were dissolved in 37 ml of absolute methanol. 1.306 (24.17 mmol) of sodium methoxide were added and the mixture was stirred at RT for 4 h. 1.452 g (24.17 mmol) of acetic acid and 1.197 g (22.38 mmol) of ammonium chloride were added and the suspension was stirred at 50° C. overnight. The reaction mixture was concentrated and the residue was suspended in 100 ml of water and 25 ml of 1N hydrochloric acid. The mixture was extracted with dichloromethane. The aqueous phase was basified (pH=12) with 2N sodium hydroxide solution and extracted three times with a mixture of dichloromethane/methanol (v/v=8:2). The combined organic phases were dried with sodium sulphate and concentrated, toluene was added and the mixture was again concentrated to dryness. 1.94 g (50% of theory) of the target compound were obtained.

Example 19A

4-Amino-2-[1-(2-fluorobenzyl)-1,4,5,6-tetrahydrocyclopenta[c]pyrazol-3-yl]-5,5-dimethyl-5,7-dihydro-6H-pyrrolo[2,3-d]pyrimidin-6-one

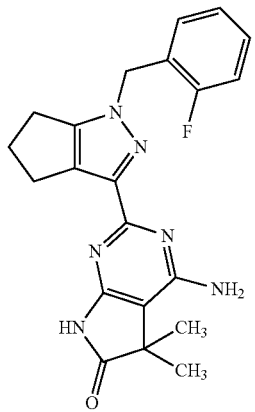 [SMILES: CC1(C)C(=O)Nc2nc(-c3nn(Cc4ccccc4F)c4c3CCC4)nc(N)c21]

300 mg (1.15 mmol) of 1-(2-fluorobenzyl)-1,4,5,6-tetrahydrocyclopenta[c]pyrazole-3-carboximidamide were admixed with 2 ml of tert-butanol, 287 mg (1.38 mmol) of methyl 3,3-dicyano-2,2-dimethylpropanoate dissolved in 2 ml of tert-butanol and 181 mg (1.61 mmol) of potassium tert-butoxide, and the mixture was heated under reflux for 72 h. The mixture was concentrated to dryness and the residue was stirred with water/isopropanol (v/v=3:1). The solid was filtered off and dried under high vacuum. 385 mg (80% of theory) of the target compound were obtained.

LC-MS (Method 1): $R_t$=0.83 min; MS (ESIpos): m/z=393 (M+H)$^+$

Example 20A 1-(2-Fluorobenzyl)-1,4,5,6-tetrahydrocyclopenta[c]pyrazole-3-carboximidohydrazide

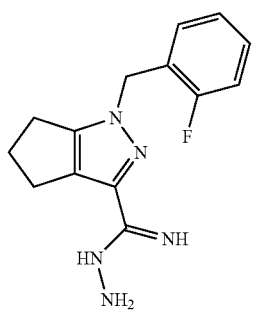 [SMILES: N=C(NN)c1nn(Cc2ccccc2F)c2c1CCC2]

200 mg (0.77 mmol) of 1-(2-fluorobenzyl)-1,4,5,6-tetrahydrocyclopenta[c]pyrazole-3-carboximidamide were initially charged in 4 ml of ethanol and cooled to 0° C. 310 mg (3.07 mmol) of triethylamine and 48 mg (0.77 mmol) of 80% hydrazine hydrate were added, and the mixture was stirred at room temperature for 72 h. The mixture was concentrated on a rotary evaporator, taken up in ethyl acetate and washed three times with saturated aqueous sodium chloride solution. The organic phase was dried over sodium sulphate, concentrated on a rotary evaporator and dried under high vacuum. 209 mg (100% of theory) of the target compound were obtained.

LC-MS (Method 1): $R_t$=0.58 min; MS (ESIpos): m/z=274 (M+H)$^+$

Example 21A

Methyl 2-{3-[1-(2-fluorobenzyl)-1,4,5,6-tetrahydrocyclopenta[c]pyrazol-3-yl]-5-hydroxy-1,2,4-triazin-6-yl}-2-methylpropanoate

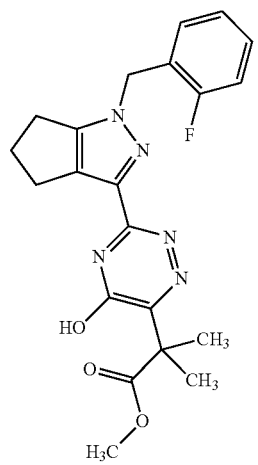 [SMILES: COC(=O)C(C)(C)c1nnc(-c2nn(Cc3ccccc3F)c3c2CCC3)nc1O]

218 mg (1.13 mmol) of dimethyl 2,2-dimethyl-3-oxobutanedioate were initially charged in 5 ml of ethanol and heated to reflux. Subsequently, 205 mg (0.75 mmol) of 1-(2-fluorobenzyl)-1,4,5,6-tetrahydrocyclopenta[c]pyrazole-3-carboximidohydrazide suspended in 5 ml of ethanol were added and the mixture was boiled under reflux overnight. After cooling, the mixture was filtered, the filtercake was washed with a little ethanol and the filtrate was concentrated. The residue was purified by means of preparative HPLC (eluent: acetonitrile/water, gradient 20:80→100:0). 48 mg of the target compound were obtained (purity 54%; 8% of theory).

LC-MS (Method 1): $R_t$=1.03 min; MS (ESIpos): m/z=412 (M+H)$^+$

Example 22A

4-Chloro-6-methyl-1H-pyrazolo[3,4-d]pyrimidine

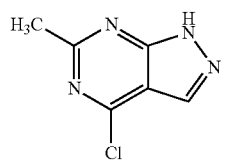

The preparation of the compound is described in: *J. Org. Chem.* 1958, 23, 191.

Example 23A

6-Methyl-1H-pyrazolo[3,4-d]pyrimidine

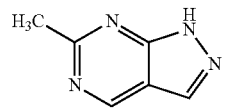

4.464 g (approx. 24.28 mmol, purity 92%) of 4-chloro-6-methyl-1H-pyrazolo[3,4-d]pyrimidine were dissolved in 180 ml of dioxane, 2.948 g (29.14 mmol) of triethylamine and 5.629 g of 20% palladium hydroxide on carbon were added, and hydrogenation was effected with hydrogen at 3 bar and RT for 2 d. 100 ml of ethyl acetate, 2.948 g (29.14 mmol) of triethylamine and 2.000 g of 20% palladium hydroxide on carbon were added. The mixture was hydrogenated with hydrogen at 3 bar and RT for 3 h. The mixture was filtered through Celite and washed with a little dioxane/ethyl acetate, and the filtrate was concentrated on a rotary evaporator. 2.180 g (purity 73%, 49% of theory) of the target compound were obtained.

LC-MS (Method 3): $R_t$=0.40 min; MS (ESIpos): m/z=135 (M+H)$^+$

Example 24A

3-Iodo-6-methyl-1H-pyrazolo[3,4-d]pyrimidine

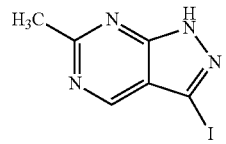

2.180 g (purity 73%, approx. 11.82 mmol) of 6-methyl-1H-pyrazolo[3,4-d]pyrimidine and 3.987 g (17.72 mmol) of N-iodosuccinimide were dissolved in 30 ml of DMF and the mixture was heated at 80° C. for 2 h. After cooling, the mixture was concentrated on a rotary evaporator and the residue was stirred with dichloromethane, filtered off with suction and dried under high vacuum. 7.950 g (38% purity, 100% of theory) of the target compound were obtained.

LC-MS (Method 1): $R_t$=0.52 min; MS (ESIpos): m/z=261 (M+H)$^+$

Example 25A 1-(2-Fluorobenzyl)-3-iodo-6-methyl-1H-pyrazolo[3,4-d]pyrimidine

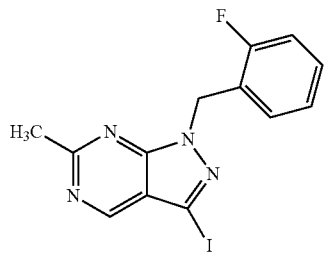 [SMILES: Cc1ncc2c(I)nn(Cc3ccccc3F)c2n1]

7.950 g (13.76 mmol) of 3-iodo-6-methyl-1H-pyrazolo[3,4-d]pyrimidine and 4.930 g (15.13 mmol) of caesium carbonate were initially charged in 20 ml of DMF, and 2.860 g (15.13 mmol) of 2-fluorobenzyl bromide dissolved in 5 ml of DMF were added. The reaction mixture was stirred at RT overnight, diluted with 100 ml of water and extracted with ethyl acetate. The organic phase was dried over sodium sulphate and concentrated on a rotary evaporator. The residue was purified by means of preparative HPLC (eluent: acetonitrile/water, gradient 30:70→95:5). 1.030 g of the target compound were obtained (20% of theory).

LC-MS (Method 3): $R_t$=2.27 min; MS (ESIpos): m/z=369 (M+H)$^+$

Example 26A 1-(2-Fluorobenzyl)-6-methyl-1H-pyrazolo[3,4-d]pyrimidine-3-carbonitrile

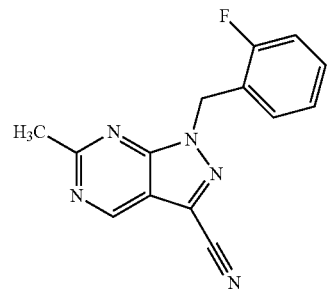 [SMILES: Cc1ncc2c(C#N)nn(Cc3ccccc3F)c2n1]

1.485 g (4.03 mmol) of 1-(2-fluorobenzyl)-3-iodo-6-methyl-1H-pyrazolo[3,4-d]pyrimidine and 397 mg (4.44 mmol) of copper(I) cyanide were initially charged in 11 ml of absolute DMSO and the mixture was heated at 150° C. for 2 h. After cooling, the mixture was filtered through Celite and washed through with ethyl acetate and THF. The organic phase was washed with 25% aqueous ammonia solution, saturated aqueous ammonium chloride solution and saturated aqueous sodium chloride solution, dried over sodium sulphate and concentrated on a rotary evaporator. 994 mg (purity 81%, 75% of theory) of the target compound were obtained.

LC-MS (Method 1): $R_t$=0.96 min; MS (ESIpos): m/z=268 (M+H)$^+$

Example 27A 1-(2-Fluorobenzyl)-6-methyl-1H-pyrazolo[3,4-d]pyrimidine-3-carboximidamide

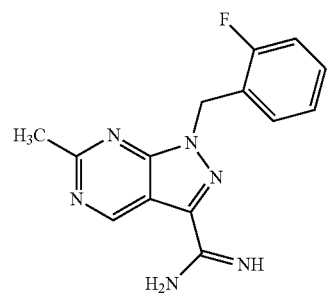 [SMILES: Cc1ncc2c(C(=N)N)nn(Cc3ccccc3F)c2n1]

Under an argon atmosphere, 994 mg (purity 81%, approx. 3.01 mmol) of 1-(2-fluorobenzyl)-6-methyl-1H-pyrazolo[3,4-d]pyrimidine-3-carbonitrile were dissolved in 15 ml of absolute methanol. 209 mg (3.72 mmol) of sodium methoxide were added and the mixture was stirred at RT for 1 h. Subsequently, 31 mg (0.56 mmol) of sodium methoxide were added and the mixture was stirred at RT for 15 min. 871 mg (14.50 mmol) of acetic acid and 489 mg (4.46 mmol) of ammonium chloride were added and the mixture was stirred at 45° C. for 45 min. The reaction mixture was concentrated, the residue was stirred with 1N sodium hydroxide solution, and the precipitate was filtered off with suction and dried under high vacuum. 918 mg (purity 91%, 97% of theory) of the target compound were obtained.

LC-MS (Method 2) $R_t$=0.53 min; MS (ESIpos): m/z=285 (M+H)$^+$

Example 28A

4-Amino-2-[1-(2-fluorobenzyl)-6-methyl-1H-pyrazolo[3,4-d]pyrimidin-3-yl]-5,5-dimethyl-5,7-dihydro-6H-pyrrolo[2,3-d]pyrimidin-6-one

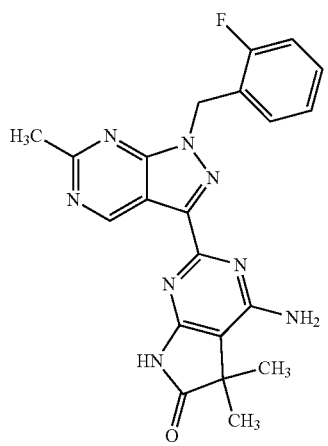 [SMILES: Cc1ncc2c(-c3nc(N)c4c(n3)NC(=O)C4(C)C)nn(Cc3ccccc3F)c2n1]

200 mg (0.70 mmol) of 1-(2-fluorobenzyl)-6-methyl-1H-pyrazolo[3,4-d]pyrimidine-3-carboximidamide were admixed with 3 ml of tert-butanol, 146 mg (0.70 mmol) of methyl 3,3-dicyano-2,2-dimethylpropanoate dissolved in 1.5 ml of tert-butanol and 94 mg (0.84 mmol) of potassium tert-butoxide, and the mixture was heated under reflux for 48 h. Water was added and the precipitate was filtered off. The filtrate was extracted with dichloromethane, and the organic phase was dried over sodium sulphate and concentrated on a rotary evaporator. The residue was stirred with water/ethanol. The solid was filtered off and dried under high vacuum. 102 mg (34% of theory) of the target compound were obtained.

LC-MS (Method 1): $R_t$=0.81 min; MS (ESIpos): m/z=419 (M+H)$^+$

Example 29A 1-(2-Fluorobenzyl)-6-methyl-1H-pyrazolo[3,4-d]pyrimidine-3-carboximidohydrazide

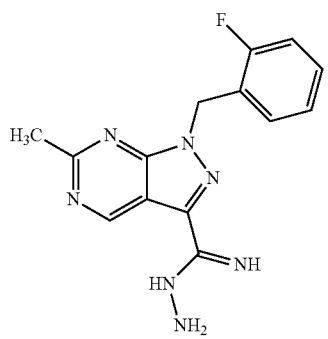 [SMILES: Cc1ncc2c(C(=N)NN)nn(Cc3ccccc3F)c2n1]

688 mg (approx. 2.20 mmol, purity 92%) of 1-(2-fluorobenzyl)-6-methyl-1H-pyrazolo[3,4-d]pyrimidine-3-carboximidamide were initially charged in 10 ml of ethanol and cooled to 0° C. 891 mg (8.80 mmol) of triethylamine and 138 mg (2.20 mmol) of 80% hydrazine hydrate were added, and the mixture was stirred at room temperature for 18 h. The mixture was concentrated on a rotary evaporator, taken up in ethyl acetate and washed three times with saturated aqueous sodium chloride solution. The organic phase was dried over sodium sulphate, concentrated on a rotary evaporator and dried under high vacuum. 654 mg (purity 93%, 92% of theory) of the target compound were obtained.

LC-MS (Method 1): $R_t$=0.54 min; MS (ESIpos): m/z=300 (M+H)$^+$

Example 30A

Methyl 2-{3-[1-(2-fluorobenzyl)-6-methyl-1H-pyrazolo[3,4-d]pyrimidin-3-yl]-5-hydroxy-1,2,4-triazin-6-yl}-2-methylpropanoate

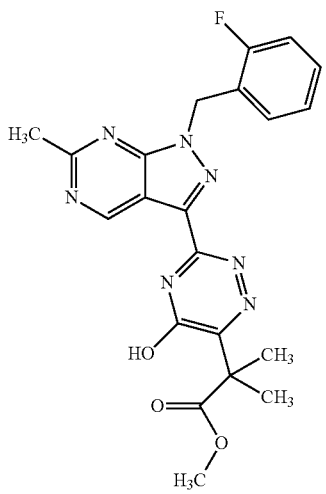 [SMILES: COC(=O)C(C)(C)c1nnc(-c2nn(Cc3ccccc3F)c3nc(C)ncc23)nc1O]

615 mg (3.27 mmol) of dimethyl 2,2-dimethyl-3-oxobutanedioate were initially charged in 13 ml of ethanol and heated to reflux. Subsequently, 652 mg (2.18 mmol) of 1-(2-fluorobenzyl)-6-methyl-1H-pyrazolo[3,4-d]pyrimidine-3-carboximidohydrazide suspended in 13 ml of ethanol were added and the mixture was boiled under reflux overnight. After cooling, the mixture was filtered, the filtercake was washed with a little ethanol and the filtrate was concentrated. The residue was purified by means of preparative HPLC (eluent: acetonitrile/water, gradient 30:70→100:0). 182 mg of the target compound were obtained (19% of theory).

LC-MS (Method 1): $R_t$=0.91 min; MS (ESIpos): m/z=438 (M+H)$^+$

Example 31A 1-(2,3-Difluorobenzyl)-3-iodo-6-methyl-1H-pyrazolo[3,4-d]pyrimidine

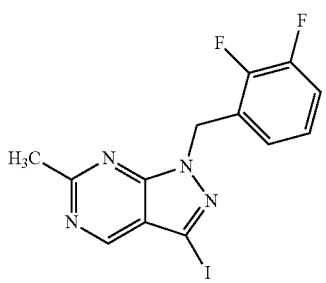 [SMILES: Cc1ncc2c(I)nn(Cc3cccc(F)c3F)c2n1]

7.100 g (approx. 10.92 mmol, purity 40%) of 3-iodo-6-methyl-1H-pyrazolo[3,4-d]pyrimidine and 4.626 g (14.20 mmol) of caesium carbonate were initially charged in 100 ml of DMF, and 2.939 g (14.20 mmol) of 2,3-difluorobenzyl bromide dissolved in 50 ml of DMF were added. The reaction mixture was stirred at RT for 3 h, added to 1.5 l of ice-water and extracted with diethyl ether. The organic phase was dried over sodium sulphate and concentrated on a rotary evaporator. The residue was purified by means of preparative HPLC (eluent: acetonitrile/water, gradient 30:70→95:5). 1.360 g of the target compound were obtained (31% of theory).

LC-MS (Method 1): $R_t$=1.04 min; MS (ESIpos): m/z=387 (M+H)$^+$

Example 32A 1-(2,3-Difluorobenzyl)-6-methyl-1H-pyrazolo[3,4-d]pyrimidine-3-carbonitrile

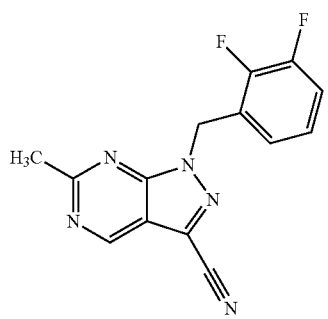 [SMILES: Cc1ncc2c(C#N)nn(Cc3cccc(F)c3F)c2n1]

1.360 g (3.35 mmol) of 1-(2,3-difluorobenzyl)-3-iodo-6-methyl-1H-pyrazolo[3,4-d]pyrimidine and 330 mg (3.68 mmol) of copper(I) cyanide were initially charged in 10 ml of absolute DMSO and the mixture was heated at 150° C. for 2 h. After cooling, the mixture was added to 200 ml of ethyl acetate and washed with a mixture of concentrated aqueous ammonia solution and semisaturated aqueous ammonium chloride solution (v/v=1:3). The organic phase was washed with saturated aqueous sodium chloride solution, dried over sodium sulphate and concentrated on a rotary evaporator. 1.040 g (purity 92%, 100% of theory) of the target compound were obtained.

LC-MS (Method 1): $R_t$=0.98 min; MS (ESIpos): m/z=286 (M+H)$^+$

Example 33A 1-(2,3-Difluorobenzyl)-6-methyl-1H-pyrazolo[3,4-d]pyrimidine-3-carboximidamide

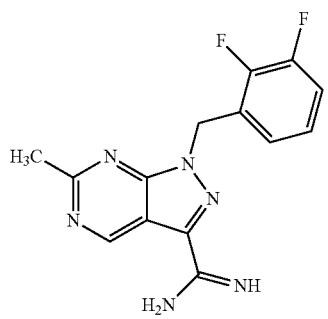 [SMILES: Cc1ncc2c(C(=N)N)nn(Cc3cccc(F)c3F)c2n1]

Under an argon atmosphere, 0.73 ml (3.35 mmol) of a 25% sodium methoxide solution was initially charged in methanol, and 1.040 g (purity 92%, 3.35 mmol) of 1-(2,3-difluorobenzyl)-6-methyl-1H-pyrazolo[3,4-d]pyrimidine-3-carbonitrile dissolved in 4 ml of absolute methanol were added. The mixture was stirred at RT for 1 h. Subsequently, 215 mg (4.03 mmol) of ammonium chloride and 786 mg (13.08 mmol) of acetic acid were added and the mixture was heated to reflux for 2 h. The reaction mixture was concentrated, and the residue was admixed with 10 ml of ethyl acetate and 15 ml of water and basified (pH=10) with 2N sodium hydroxide solution. The mixture was stirred at RT for 1 h, water was added and the mixture was extracted with ethyl acetate. The organic phase was dried over sodium sulphate, concentrated and dried under high vacuum. 840 mg (purity 85%, 70% of theory) of the target compound were obtained.

LC-MS (Method 1): $R_t$=0.64 min; MS (ESIpos): m/z=303 (M+H)$^+$

Example 34A

4-Amino-2-[1-(2,3-difluorobenzyl)-6-methyl-1H-pyrazolo[3,4-d]pyrimidin-3-yl]-5,5-dimethyl-5,7-dihydro-6H-pyrrolo[2,3-d]pyrimidin-6-one

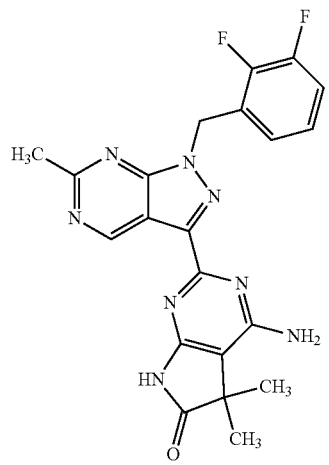 [SMILES: Cc1ncc2c(-c3nc(N)c4c(n3)NC(=O)C4(C)C)nn(Cc3cccc(F)c3F)c2n1]

400 mg (1.11 mmol) of 1-(2,3-difluorobenzyl)-6-methyl-1H-pyrazolo[3,4-d]pyrimidine-3-carboximidamide were admixed with 3 ml of tert-butanol, 277 mg (1.33 mmol) of methyl 3,3-dicyano-2,2-dimethylpropanoate dissolved in 2 ml of tert-butanol and 175 mg (1.56 mmol) of potassium tert-butoxide, and the mixture was heated to reflux for 24 h. A little water was added and the reaction solution was purified by means of preparative HPLC (eluent: acetonitrile/water, gradient 30:70→95:5). The product-containing fractions were concentrated and the residue was stirred with water/isopropanol. The solids were filtered off and purified again by means of preparative HPLC (eluent: acetonitrile/water with 0.1% hydrochloric acid, gradient 20:80→100:0). 170 mg (35% of theory) of the target compound were obtained.

LC-MS (Method 1): $R_t$=0.87 min; MS (ESIpos): m/z=437 (M+H)$^+$

Example 35A 1-(2,3-Difluorobenzyl)-6-methyl-1H-pyrazolo[3,4-d]pyrimidine-3-carboximidohydrazide

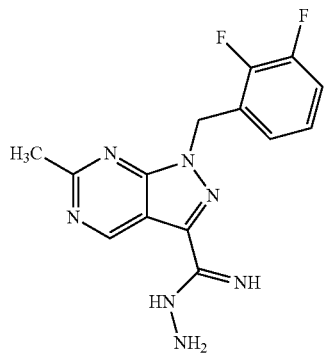 [SMILES: Cc1ncc2c(C(=N)NN)nn(Cc3cccc(F)c3F)c2n1]

Under an argon atmosphere, 440 mg (1.237 mmol, purity 85%) of 1-(2,3-difluorobenzyl)-6-methyl-1H-pyrazolo[3,4-d]pyrimidine-3-carboximidamide were initially charged in 6 ml of ethanol and cooled to 0° C. 500 mg (4.49 mmol) of triethylamine and 85 mg (1.361 mmol) of 80% hydrazine hydrate were added, and the mixture was stirred at room temperature for 72 h. The mixture was concentrated on a rotary evaporator, taken up in ethyl acetate and washed three times with saturated aqueous sodium chloride solution. The organic phase was dried over sodium sulphate, concentrated on a rotary evaporator and dried under high vacuum. 421 mg (purity 84%, 90% of theory) of the target compound were obtained.

LC-MS (Method 1): $R_t$=0.55 min; MS (ESIpos): m/z=318 $(M+H)^+$

Example 36A

Methyl 2-{3-[1-(2,3-difluorobenzyl)-6-methyl-1H-pyrazolo[3,4-d]pyrimidin-3-yl]-5-hydroxy-1,2,4-triazin-6-yl}-2-methylpropanoate

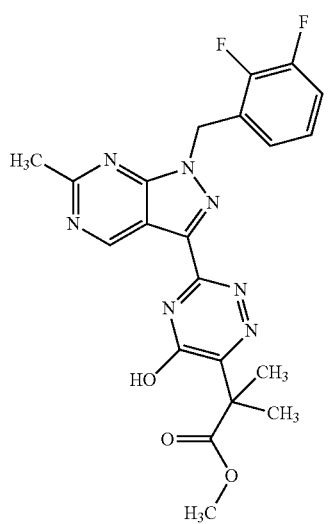 [SMILES: COC(=O)C(C)(C)c1nnc(-c2nn(Cc3cccc(F)c3F)c3nc(C)ncc23)nc1O]

374 mg (1.985 mmol) of dimethyl 2,2-dimethyl-3-oxobutanedioate were initially charged in 8 ml of ethanol and heated to reflux. Subsequently, 420 mg (1.324 mmol) of 1-(2,3-difluorobenzyl)-6-methyl-1H-pyrazolo[3,4-d]pyrimidine-3-carboximidohydrazide suspended in 8 ml of ethanol were added and the mixture was heated to reflux overnight. Another 299 mg (1.588 mmol) of dimethyl 2,2-dimethyl-3-oxobutanedioate dissolved in 3 ml of ethanol were added and the mixture was boiled under reflux overnight. After cooling, the mixture was filtered and purified directly by means of preparative HPLC (eluent: acetonitrile/water, gradient 30:70→100:0). 163 mg of the target compound were obtained (purity 89%; 24% of theory).

LC-MS (Method 1): $R_t$=0.96 min; MS (ESIpos): m/z=456 $(M+H)^+$

Example 37A

1H-Pyrazolo[3,4-d]pyrimidine

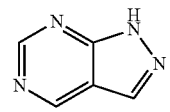

The preparation of the compound is described in: *J. Am. Chem. Soc.* 1956, 78, 784.

Example 38A

3-Iodo-1H-pyrazolo[3,4-d]pyrimidine

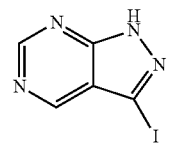

520 mg (4.331 mmol) of 1H-pyrazolo[3,4-d]pyrimidine and 1.461 g (6.496 mmol) of N-iodosuccinimide were dissolved in 10 ml of DMF and the mixture was heated at 80° C. for 3 h. After cooling, the mixture was concentrated on a rotary evaporator and the residue was stirred with dichloromethane, filtered off with suction and dried under high vacuum. 569 mg (53% of theory) of the target compound were obtained.

LC-MS (Method 3): $R_t$=1.23 min; MS (ESIpos): m/z=247 $(M+H)^+$

Example 39A 1-(2-Fluorobenzyl)-3-iodo-1H-pyrazolo[3,4-d]pyrimidine

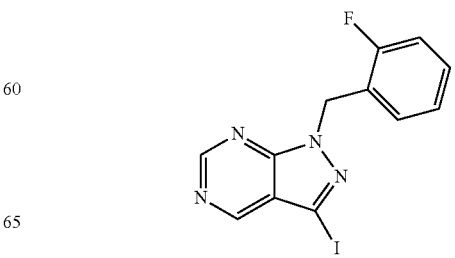

569 mg (2.313 mmol) of 3-iodo-1H-pyrazolo[3,4-d]pyrimidine and 828 mg (2.544 mmol) of caesium carbonate were initially charged in 10 ml of DMF, and 481 mg (2.544 mmol) of 2-fluorobenzyl bromide dissolved in 2 ml of DMF were added. The reaction mixture was stirred at RT overnight, diluted with 50 ml of water and filtered with suction, and the residue was dried under high vacuum. 733 mg of the target compound were obtained (purity 83%; 74% of theory).

LC-MS (Method 1): $R_t$=0.96 min; MS (ESIpos): m/z=355 (M+H)$^+$

Example 40A 1-(2-Fluorobenzyl)-1H-pyrazolo[3,4-d]pyrimidine-3-carbonitrile

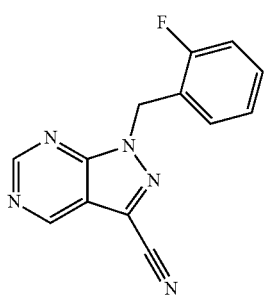 [SMILES: N#Cc1nn(Cc2ccccc2F)c2ncncc12]

950 mg (purity 85%, approx. 2.281 mmol) of 1-(2-fluorobenzyl)-3-iodo-1H-pyrazolo[3,4-d]pyrimidine and 225 mg (2.509 mmol) of copper(I) cyanide were initially charged in 6 ml of absolute DMSO and the mixture was heated at 150° C. for 2 h. After cooling, the mixture was filtered through Celite and washed through with ethyl acetate and THF. The organic phase was washed with 25% aqueous ammonia solution, saturated aqueous ammonium chloride solution and saturated aqueous sodium chloride solution, dried over sodium sulphate and concentrated on a rotary evaporator. 685 mg (purity 84%, 99% of theory) of the target compound were obtained.

LC-MS (Method 2) $R_t$=0.95 min; MS (ESIpos): m/z=254 (M+H)$^+$

Example 41A 1-(2-Fluorobenzyl)-1H-pyrazolo[3,4-d]pyrimidine-3-carboximidamide acetate

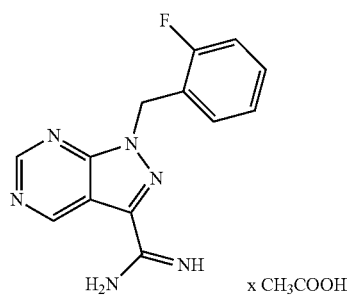 [SMILES: N=C(N)c1nn(Cc2ccccc2F)c2ncncc12]

Under an argon atmosphere, 685 mg (purity 84%, approx. 2.273 mmol) of 1-(2-fluorobenzyl)-1H-pyrazolo[3,4-d]pyrimidine-3-carbonitrile were dissolved in 8 ml of absolute methanol. 127 mg (2.273 mmol) of sodium methoxide were added and the mixture was stirred at RT for 1 h. 532 mg (8.864 mmol) of acetic acid and 299 mg (2.273 mmol) of ammonium chloride were added and the mixture was boiled under reflux for 45 min. The reaction mixture was concentrated, the residue was stirred with 20 ml of 1N sodium hydroxide solution, and the precipitate was filtered off with suction and dried under high vacuum. 610 mg (purity 86%, 86% of theory) of the target compound were obtained.

LC-MS (Method 1): $R_t$=0.53 min; MS (ESIpos): m/z=271 (M+H)$^+$

Example 42A 1-(2-Fluorobenzyl)-1H-pyrazolo[3,4-d]pyrimidine-3-carboximidohydrazide

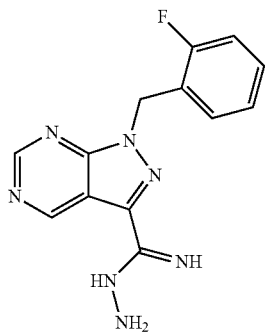 [SMILES: N=C(NN)c1nn(Cc2ccccc2F)c2ncncc12]

610 mg (approx. 1.92 mmol, purity 86%) of 1-(2-fluorobenzyl)-1H-pyrazolo[3,4-d]pyrimidine-3-carboximidamide were initially charged in 10 ml of ethanol and cooled to 0° C. 777 mg (7.68 mmol) of triethylamine and 120 mg (1.920 mmol) of 80% hydrazine hydrate were added, and the mixture was stirred at room temperature for 18 h. The mixture was concentrated on a rotary evaporator, taken up in ethyl acetate and washed three times with saturated aqueous sodium chloride solution. The organic phase was dried over sodium sulphate, concentrated on a rotary evaporator and dried under high vacuum. 590 mg (purity 89%, 95% of theory) of the target compound were obtained.

LC-MS (Method 3): $R_t$=1.37 min; MS (ESIpos): m/z=286 (M+H)$^+$

Example 43A

Methyl 2-{3-[1-(2-fluorobenzyl)-1H-pyrazolo[3,4-d]pyrimidin-3-yl]-5-hydroxy-1,2,4-triazin-6-yl}-2-methylpropanoate

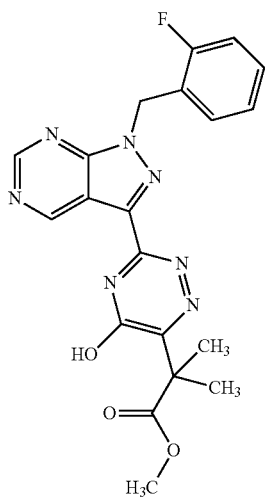 [SMILES: COC(=O)C(C)(C)c1nnc(-c2nn(Cc3ccccc3F)c3ncncc23)nc1O]

584 mg (3.103 mmol) of dimethyl 2,2-dimethyl-3-oxobutanedioate were initially charged in 12 ml of ethanol and heated to reflux. Subsequently, 590 mg (2.069 mmol) of 1-(2-fluorobenzyl)-1H-pyrazolo[3,4-d]pyrimidine-3-carboximidohydrazide suspended in 12 ml of ethanol were added and the mixture was boiled under reflux overnight. After cooling, the mixture was filtered, the filtercake was washed with a little ethanol and the filtrate was concentrated. The residue was stirred with 10 ml of acetonitrile. 188 mg of the target compound were obtained (purity 93%; 20% of theory).

LC-MS (Method 2) $R_t$=0.90 min; MS (ESIpos): m/z=424 (M+H)$^+$

Example 44A

Dimethyl 3-(2-carbamoylhydrazinylidene)-2,2-dimethylbutanedioate

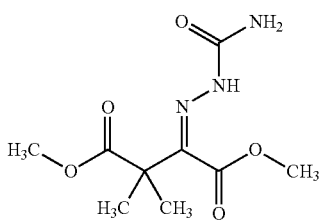

10 g (90 mmol) of semicarbazide hydrochloride, 15.5 g (82 mmol) of dimethyl 2,2-dimethyl-3-oxobutanedioate and 8.1 g (82 mmol) of sodium acetate were stirred in 135 ml of water at RT overnight and left to stand for two days. The mixture was cooled with ice-water, and the colourless precipitate was filtered off, washed with a little water and dried.

Yield: 15.4 g (77% of theory)

LC-MS (Method 3): $R_t$=1.51 min; MS (ESIpos): m/z=246 (M+H)$^+$ $^1$H NMR (400 MHz, DMSO-$d_6$) δ [ppm]=1.37 (s, 6H), 3.59 (s, 3H), 3.76 (s, 3H), 6.77 (br. s., 2H), 10.82 (s, 1H)

Example 45A

Methyl 2-(3,5-dioxo-2,3,4,5-tetrahydro-1,2,4-triazin-6-yl)-2-methylpropanoate

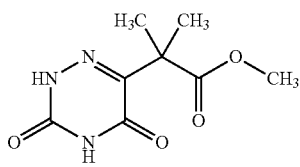

15.35 g (62.5 mmol) of Example 44A were dissolved in 235 ml of methanol, and 6.8 g (125 mmol) of sodium methoxide were added, causing a colourless solid to precipitate out rapidly. The mixture was diluted with 235 ml of methanol and the reaction mixture was subsequently heated to reflux for 1.5 h. Cooling was followed by concentration, and the residue was added gradually to a solution of 14.4 ml (251 mmol) of glacial acetic acid in 150 ml of water. The mixture was partly concentrated and cooled with ice-water, and the precipitated solid was filtered off with suction, washed with a little water and dried at 45° C. under reduced pressure overnight.

Yield: 11.0 g (82% of theory).

LC-MS (Method 3): $R_t$=1.28 min; MS (ESIpos): m/z=212 (M−H)$^-$ $^1$H NMR (400 MHz, DMSO-$d_6$) δ [ppm]=1.35 (s, 6H), 3.55 (s, 3H), 12.16 (br. s., 2H)

Example 46A

Methyl 2-(3,5-dichloro-1,2,4-triazin-6-yl)-2-methylpropanoate

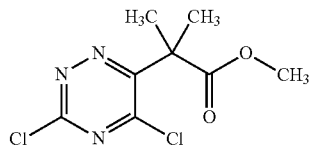

5.15 g (24 mmol) of Example 45A were heated to reflux in 100 ml of phosphorus oxychloride and 1 ml of DMF overnight. The reaction mixture was concentrated and then triturated cautiously with ice with external cooling in an ice bath. After adding dichloromethane, solid sodium hydrogencarbonate was used to set pH 6 while stirring, the phases were separated and the water phase was extracted with dichloromethane. The combined organic phases were dried and concentrated. The residue (4.88 g) was filtered through a silica gel layer with dichloromethane/ethyl acetate (10:1).

Yield: 3.1 g (51% of theory)

LC-MS (Method 3): $R_t$=2.08 min; MS (ESIpos): m/z=250 (M+H)$^+$

Example 47A

3-Chloro-7,7-dimethyl-5,7-dihydro-6H-pyrrolo[2,3-e][1,2,4]triazin-6-one

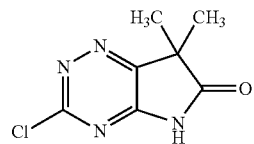

2 g (8 mmol) of Example 46A were dissolved in 30 ml of dioxane, 10 ml of aq. conc. ammonia were added and the mixture was stirred at RT overnight. The reaction solution was concentrated. The residue was stirred with 50 ml of water and then filtered off with suction.

Yield: 1.12 g (71% of theory)

LC-MS (Method 3): $R_t$=1.15 min; MS (ESIpos): m/z=199 (M+H)$^+$ $^1$H NMR (400 MHz, DMSO-$d_6$) δ [ppm]=1.40 (s, 6H), 12.40 (br. s, 1H)

Example 48A

3-Chloro-5-(4-methoxybenzyl)-7,7-dimethyl-5,7-dihydro-6H-pyrrolo[2,3-e][1,2,4]triazin-6-one

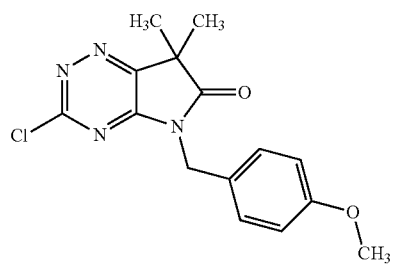 [SMILES: COc1ccc(CN2C(=O)C(C)(C)c3nnc(Cl)nc32)cc1]

To a solution of 390 mg (2.84 mmol) of 4-methoxybenzylamine and 2.3 ml (13.2 mmol) of diisopropylethylamine in 10 ml of THF was added dropwise, at 0° C., a solution of 645 mg (2.58 mmol) of Example 46A in 5 ml of THF, and the suspension was stirred at RT overnight. The reaction mixture was concentrated under reduced pressure. Yield: 1.4 g of crude product. 1.1 g of the crude product were purified twice with dichloromethane/methanol (100:1) by column chromatography on silica gel.

Yield: 395 mg (60% of theory)

LC-MS (Method 1): $R_t$=1.01 min; MS (ESIpos): m/z=319 (M+H)$^+$

Example 49A

3-[6-Fluoro-3-(2-fluorobenzyl)-1H-pyrazolo[4,3-b]pyridin-1-yl]-5-(4-methoxybenzyl)-7,7-dimethyl-5,7-dihydro-6H-pyrrolo[2,3-e][1,2,4]triazin-6-one

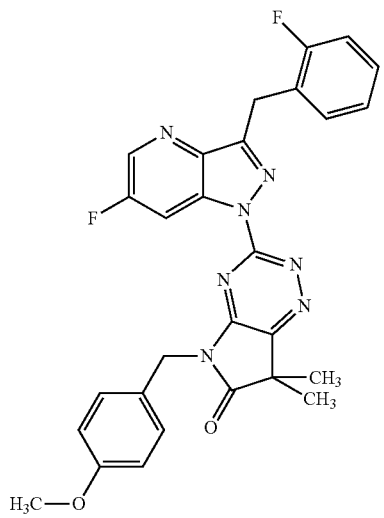 [SMILES: COc1ccc(CN2C(=O)C(C)(C)c3nnc(-n4nc(Cc5ccccc5F)c5ncc(F)cc54)nc32)cc1]

200 mg (0.82 mmol) of Example 15A were dissolved in 3 ml of NMP, 40 mg (1 mmol) of sodium hydride (60%) were added and the mixture was stirred at RT for 30 min. Subsequently, 235 mg of crude product from Example 48A were added and the mixture was stirred at 80° C. for 2 h. The reaction mixture was admixed with water and concentrated. Purification by means of prep. HPLC (Reprosil C18, gradient of acetonitrile/0.01% aq. formic acid) gave 131 mg (30% of theory) of the title compound.

LC-MS (Method 1) $R_t$=1.29 min; MS (ESIpos): m/z=528 (M+H)$^+$ $^1$H NMR (400 MHz, DMSO-$d_6$) δ [ppm]=1.50 (s, 6H), 3.72 (s, 3H), 3.72 (s, 3H), 4.49 (s, 2H), 4.92 (s, 2H), 6.88 (d, 2H), 7.10-7.24 (m, 2H), 7.26-7.38 (m, 3H), 7.42 (t, 1H), 8.51 (dd, 1H), 8.75 (m, 1H)

Example 50A

5-Fluoro-3-(2-fluorobenzyl)-1H-indazole

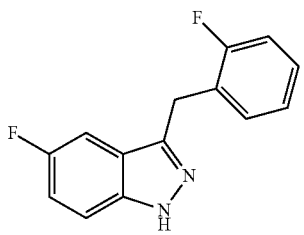 [SMILES: Fc1ccc2[nH]nc(Cc3ccccc3F)c2c1]

The title compound was prepared proceeding from 2,5-difluorobenzoyl chloride and methyl 2-fluorophenylacetate, analogously to the method for Example 12A, 13A, 14A and 15A.

LC-MS (Method 1): $R_t$=0.97 min; MS (ESIpos): m/z=245 (M+H)$^+$ $^1$H NMR (400 MHz, DMSO-$d_6$) δ [ppm]=4.27 (s, 2H), 7.01-7.42 (m, 6H), 7.51 (dd, 1H), 12.90 (br. s., 1H)

Example 51A

5-Fluoro-3-(3,3,4,4,4-pentafluorobutyl)-1H-indazole

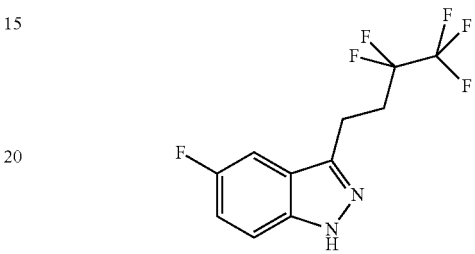

Step a) Preparation of iodo(3,3,4,4,4-pentafluorobutyl)zinc (analogous to *J. Org. Chem.* 2002, 76, 6863-6870)

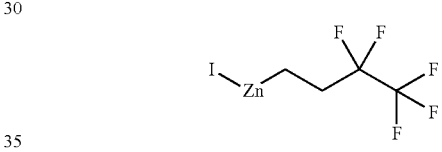

Under argon, 7.16 g (110 mmol) of zinc powder were initially charged in 22 ml of THF. While stirring, 1.45 g (7.7 mmol) of 1,2-dibromoethane were added and the mixture was heated briefly to boiling four times with a hot air gun and cooled again to RT. Then 230 mg (2.12 mmol) of trimethylsilyl chloride were added, the mixture was stirred at RT for 10 min and finally, with external cooling with ice-water, a solution of 10 g (36.5 mmol) of 1,1,1,2,2-pentafluoro-4-iodobutane in 22 ml THF were added dropwise at RT and stirring was continued for 15 min. The reagent was taken from the dark grey suspension via a microfilter using a syringe. For the solution, a content of 0.83 M was assumed.

Step b) 5-Fluoro-3-(3,3,4,4,4-pentafluorobutyl)-1H-indazole

A solution of 2.0 g (5.52 mmol) of tert-butyl 5-fluoro-3-iodo-1H-indazole-1-carboxylate (Herdemann M. et al. *Bioorg. Med. Chem. Lett.*, 2010, 20, 6998-7003) in 30 ml of anhydrous THF was evacuated and filled with argon three times. Then 506 mg (0.55 mol) of tris(dibenzylideneacetone)dipalladium and 256.5 mg (1.11 mmol) of tri(2-furyl)phosphine were added, and the mixture was evacuated once again and filled with argon. Then 9.32 ml (approx. 7.73 mmol) of the solution from step a) were added at 4-6° C. within 20 min, and stirring was continued at 4° C. for 10 min and without external cooling overnight. Water was added and the mixture was extracted three times with ethyl acetate. The combined organic phases were washed with saturated aqueous sodium chloride solution, dried and concentrated. A portion of the residue (470 mg) was purified by means of preparative HPLC (Reprosil C18, gradient of acetonitrile/0.01% aq. formic acid). Yield: 190 mg (13% of theory).

The second portion of the residue (1.9 g) was purified by chromatography on 120 g of silica gel with isohexane/ethyl acetate (gradient 10:1 to 2:1). 915 mg (purity 86%, corresponds to 51% of theory) of the title compound were obtained. Overall yield: 64% of theory LC-MS (Method 1): $R_t$=1.05 min; MS (ESIpos): m/z=283 (M+H)+

1H NMR (400 MHz, DMSO-$d_6$): δ [ppm]=2.60-2.84 (m, 2H), 3.10-3.25 (m, 2H), 7.23 (td, 1H), 7.44-7.57 (m, 1H), 7.63 (dd, 1H), 12.93 (s, 1H).

Example 52A

3-[6-Fluoro-3-(3,3,4,4,4-pentafluorobutyl)-1H-pyrazolo[4,3-b]pyridin-1-yl]-5-(4-methoxybenzyl)-7,7-dimethyl-5,7-dihydro-6H-pyrrolo[2,3-e][1,2,4]triazin-6-one

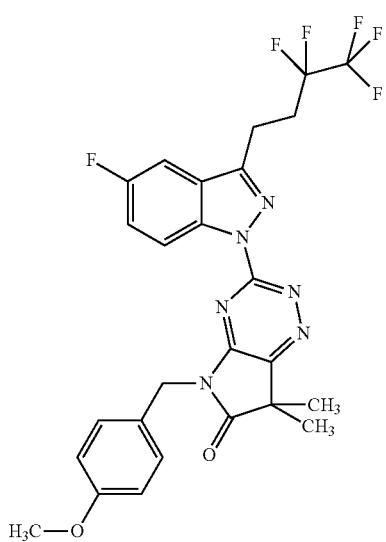 [SMILES: COc1ccc(CN2C(=O)C(C)(C)c3nnc(-n4nc(CCC(F)(F)C(F)(F)F)c5cc(F)ccc54)nc32)cc1]

150 mg (0.53 mmol) of Example 51A were dissolved in 2 ml of NMP, 21.3 mg (0.53 mmol) of sodium hydride (60%) were added and the mixture was stirred at RT for 30 min. Subsequently, 141 mg (0.44 mmol) of Example 48A were added, and the mixture was stirred at RT for 7 h and left to stand for 2 days. A further 12.4 mg (0.31 mmol) of sodium hydride and 85 mg (0.27 mmol) of Example 48A were added and the mixture was stirred at 60° C. for 3 h. After cooling, 5 M formic acid was used to set a pH of 4-5 and purification was effected by means of prep. HPLC (Reprosil C18, gradient of acetonitrile/0.01% aq. formic acid). Yield: 74 mg (25% of theory)

LC-MS (Method 4): $R_t$=1.38 min; MS (ESIpos): m/z=565 (M+H)+

1H NMR (400 MHz, DMSO-$d_6$) δ [ppm]=1.50 (s, 6H), 2.77-2.96 (m, 2H), 3.35 (t, 2H), 3.71 (s, 3H), 4.92 (s, 2H), 6.90 (d, 2H), 7.39 (d, 2H), 7.51 (td, 1H), 7.89 (d, 1H), 8.51 (dd, 1H)

Example 53A

6-Chloro-1-(2-fluorobenzyl)-1H-indazole-3-carbonitrile

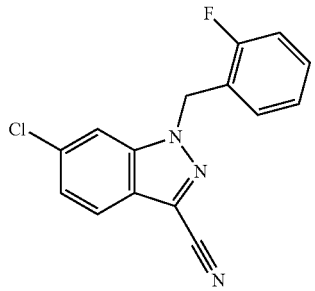 [SMILES: N#Cc1nn(Cc2ccccc2F)c2cc(Cl)ccc12]

Under argon, 2.45 ml (14.2 mmol) of 2-fluorobenzyl bromide, dissolved in 10 ml DMF, were added to a mixture of 2.3 g (12.9 mmol) of 6-chloro-1H-indazole-3-carbonitrile (WO 2011/149921, Expl. 58C) and 2.15 g (15.5 mmol) of potassium carbonate in 40 ml of DMF, and the mixture was stirred at RT overnight. Then the mixture was poured onto 90 ml of water and the mixture was stirred at room temperature for 30 min. The precipitated solids were filtered off, washed with water and dried under high vacuum overnight. 3.77 g of the title compound were obtained as a crude product.

LC-MS (Method 1): $R_t$=1.22 min; MS (ESIpos): m/z=286 (M+H)+

1H NMR (400 MHz, DMSO-$d_6$): δ [ppm]=5.87 (s, 2H), 7.16-7.36 (m, 3H), 7.37-7.50 (m, 2H), 7.95 (d, 1H), 8.26 (s, 1H).

Example 54A

6-Chloro-1-(2-fluorobenzyl)-1H-indazole-3-carboximidamide acetate (1:1)

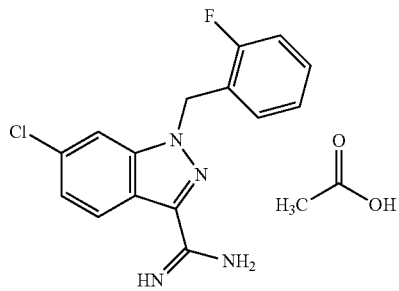

Under argon, 3.77 g (13.20 mmol, theor. 12.95 mmol) of Example 53A were added to 0.71 g (13.20 mmol) of sodium methoxide in 60 ml of methanol and the mixture was stirred at RT overnight. Then 0.85 g (15.83 mmol) of ammonium chloride and 2.95 ml (51.46 mmol) of acetic acid were added and the mixture was stirred at 80° C. overnight. The mixture was cooled and concentrated under reduced pressure, ethyl acetate and 1M aqueous sodium hydroxide solution were added, and the mixture was stirred at room temperature for 30 min. The solids were filtered off, washed with ethyl acetate and dried under high vacuum overnight. 2.56 g of the title compound were obtained (55% of theory).

LC-MS (Method 1): $R_t$=0.70 min; MS (ESIpos): m/z=303 (M+H)+

1H NMR (400 MHz, DMSO-$d_6$): δ [ppm]=1.82 (s, 3H), 5.80 (s, 2H), 7.06-7.20 (m, 2H), 7.20-7.28 (m, 1H), 7.28-7.43 (m, 2H), 8.03 (s, 1H), 8.22 (d, 1H).

Example 55A

6-Chloro-1-(2-fluorobenzyl)-1H-indazole-3-carboximidohydrazide

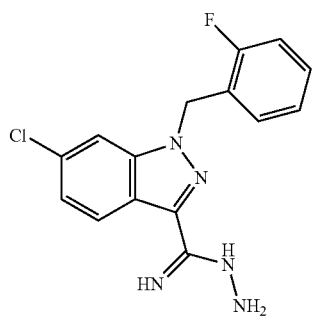

At 0° C., 500 mg (1.38 mmol) of Example 54A in 15 ml ethanol were admixed with 0.77 ml (5.51 mmol) of triethylamine and 0.08 ml (1.38 mmol) of 80% hydrazine hydrate, and the mixture was stirred first at 0° C. for 10 min and then at room temperature overnight. Subsequently, 10% aq. sodium chloride solution was added and the mixture was extracted twice with ethyl acetate. The combined organic phases were washed with 10% aqueous sodium chloride solution, dried over sodium sulphate, concentrated under reduced pressure at room temperature and dried under high vacuum overnight. 408 mg (93% of theory) of the title compound were obtained.

LC-MS (Method 1): $R_t$=0.75 min; MS (ESIpos): m/z=318 (M+H)$^+$ $^1$H NMR (400 MHz, DMSO-d$_6$): δ [ppm]=5.31 (br. s., 2H), 5.44 (br. s, 2H), 5.70 (s, 2H), 6.99-7.06 (m, 1H), 7.10-7.27 (m, 3H), 7.31-7.40 (m, 1H), 7.88 (d, 1H), 8.19 (d, 1H).

Example 56A

Methyl 2-{3-[6-chloro-1-(2-fluorobenzyl)-1H-indazol-3-yl]-5-hydroxy-1,2,4-triazin-6-yl}-2-methylpropanoate

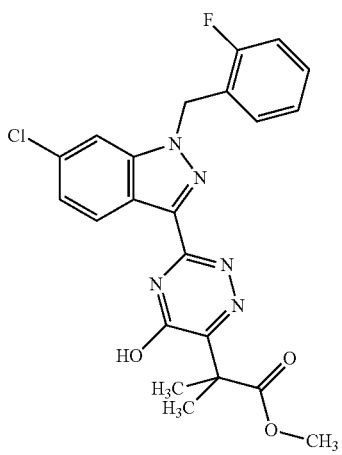 [SMILES: COC(=O)C(C)(C)c1nnc(-c2nn(Cc3ccccc3F)c3cc(Cl)ccc23)nc1O]

479.7 mg (2.55 mmol) of dimethyl 2,2-dimethyl-3-oxobutanedioate (Helv. Chim Acta, 1959, 42, 2584) in 10 ml of ethanol were heated to reflux, a suspension of 405 mg (1.28 mmol) of Example 55A in 10 ml of ethanol was added and the mixture was stirred at reflux overnight. After cooling, the precipitated solids were filtered off, washed with ethanol and ether and dried. Yield: 198.4 mg (34% of theory). After concentrating the filtrate, a further 527 mg of crude product of the title compound were obtained.

LC-MS (Method 1): $R_t$=1.17 min; MS (ESIpos): m/z=456 (M+H)$^+$

Example 57A

6-Chloro-1-[(3-fluoropyridin-2-yl)methyl]-1H-indazole-3-carbonitrile

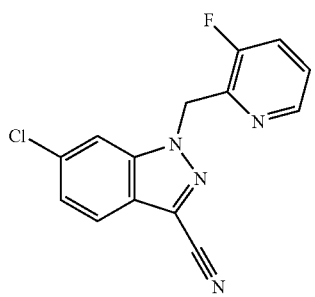 [SMILES: N#Cc1nn(Cc2ncccc2F)c2cc(Cl)ccc12]

2.3 g (12.95 mmol) of 6-chloro-1H-indazole-3-carbonitrile (WO 2011/149921, Expl. 58C) were reacted in analogy to Example 53A with 2.07 g (14.25 mmol) of 2-(chloromethyl)-3-fluoropyridine. 3.44 g of the title compound were obtained (93% of theory).

LC-MS (Method 1): $R_t$=1.09 min; MS (ESIpos): m/z=287 (M+H)$^+$ $^1$H NMR (400 MHz, DMSO-d$_6$): δ [ppm]=6.05 (s, 2H), 7.41-7.51 (m, 2H), 7.76-7.85 (m, 1H), 7.96 (d, 1H), 8.22 (s, 1H), 8.29 (d, 1H).

Example 58A

6-Chloro-1-[(3-fluoropyridin-2-yl)methyl]-1H-indazole-3-carboximidamide acetate

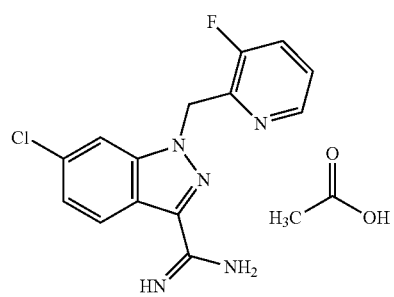

3.44 g (12.0 mmol) of Example 57A were converted in analogy to Example 54A. 3.02 g (69% of theory) of the title compound were obtained.

LC-MS (Method 1): $R_t$=0.73 min; MS (ESIpos): m/z=303 (M+H)$^+$

¹H NMR (400 MHz, DMSO-d₆): δ [ppm]=1.78 (s, 3H), 5.94 (s, 2H), 7.30 (dd, 1H), 7.45 (dt, 1H), 7.78 (t, 1H), 7.99 (s, 1H), 8.24 (d, 1H), 8.30 (d, 1H).

Example 59A

6-Chloro-1-[(3-fluoropyridin-2-yl)methyl]-1H-indazole-3-carboximidohydrazide

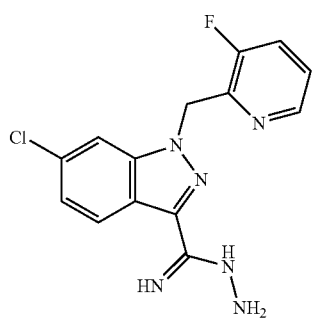 [SMILES: N=C(NN)c1nn(Cc2ncccc2F)c2cc(Cl)ccc12]

500 mg (1.37 mmol) of Example 58A were converted in analogy to Example 55A. 393.3 mg of the title compound were obtained (90% of theory).

LC-MS (Method 1): $R_t$=0.65 min; MS (ESIpos): m/z=319 (M+H)⁺

¹H NMR (400 MHz, DMSO-d₆): δ [ppm]=5.26-5.57 (m, 3H), 5.85 (s, 2H), 7.18 (dd, 1H), 7.40-7.48 (m, 1H), 7.76 (t, 1H), 7.87 (s, 1H), 8.18 (d, 1H), 8.30 (d, 1H).

Example 60A

Methyl 2-(3-[6-chloro-1-[(3-fluoropyridin-2-yl)methyl]-1H-indazol-3-yl]-5-hydroxy-1,2,4-triazin-6-yl)-2-methylpropanoate

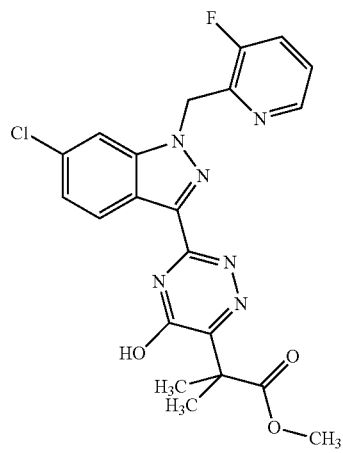 [SMILES: COC(=O)C(C)(C)c1nnc(-c2nn(Cc3ncccc3F)c3cc(Cl)ccc23)nc1O]

391 mg (1.23 mmol) of Example 59A were converted in analogy to Example 56A. The title compound was obtained as a crude product (685.2 mg) after concentrating the reaction solution.

LC-MS (Method 1): $R_t$=1.05 min; MS (ESIpos): m/z=457 (M+H)⁺

Example 61A

6-Chloro-1-(3,3,4,4,4-pentafluorobutyl)-1H-indazole-3-carboximidohydrazide

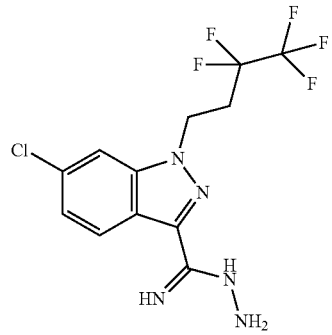 [SMILES: N=C(NN)c1nn(CCC(F)(F)C(F)(F)F)c2cc(Cl)ccc12]

1 g (2.08 mmol, purity 71%) of 6-chloro-1-(3,3,4,4,4-pentafluorobutyl)-1H-indazole-3-carboximidamide (WO 2011/149921 Expl. 58E) was converted analogously to Example 55A. 1.04 g of the title compound were obtained as a crude product.

LC-MS (Method 1): $R_t$=0.77 min; MS (ESIpos): m/z=356 (M+H)⁺

Example 62A

Methyl 2-{3-[6-chloro-1-(3,3,4,4,4-pentafluorobutyl)-1H-indazol-3-yl]-5-hydroxy-1,2,4-triazin-6-yl}-2-methylpropanoate

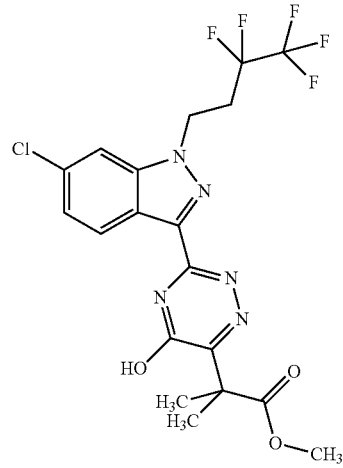 [SMILES: COC(=O)C(C)(C)c1nnc(-c2nn(CCC(F)(F)C(F)(F)F)c3cc(Cl)ccc23)nc1O]

629.6 mg (1.77 mmol) of Example 61A (crude product) were converted analogously to Example 56A. 488.4 mg (56% of theory) of the title compound were obtained as a crude product.

LC-MS (Method 1): $R_t$=1.17 min; MS (ESIpos): m/z=494 (M+H)⁺

WORKING EXAMPLES

Example 1

2-[5-Chloro-3-(2,3,6-trifluorobenzyl)-1H-indazol-1-yl]-4-iodo-5,5-dimethyl-5,7-dihydro-6H-pyrrolo[2,3-d]pyrimidin-6-one

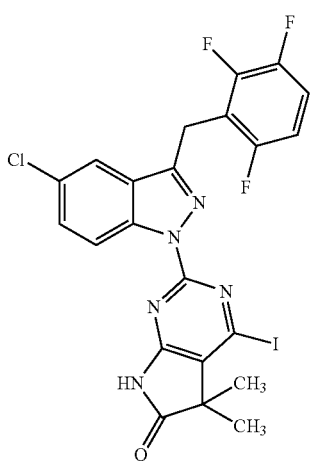 [SMILES: CC1(C)C(=O)Nc2nc(-n3nc(Cc4c(F)ccc(F)c4F)c4cc(Cl)ccc43)nc(I)c21]

100 mg (0.211 mmol) of Example 3A were initially charged in isopentyl nitrite (0.612 ml) and diiodomethane (1.60 ml), and the mixture was heated to 85° C. overnight. After cooling, purification was effected by means of preparative HPLC (acetonitrile:water (+0.05% formic acid) gradient). 53 mg of the title compound were obtained (42% of theory).

LC-MS (Method 2): $R_t$=1.44 min; MS (ESIpos): m/z=584 (M+H)$^+$ $^1$H NMR (400 MHz, DMSO-d$_6$): δ [ppm]=1.40 (s, 6H), 4.50 (s, 2H), 7.19-7.24 (m, 1H), 7.47-7.53 (m, 1H), 7.72 (dd, 1H), 8.00 (d, 1H), 8.56 (d, 1H), 11.89 (s, 1H).

Example 2

2-[5-Chloro-3-(2,3,6-trifluorobenzyl)-1H-indazol-1-yl]-5,5-dimethyl-5,7-dihydro-6H-pyrrolo[2,3-d]pyrimidin-6-one

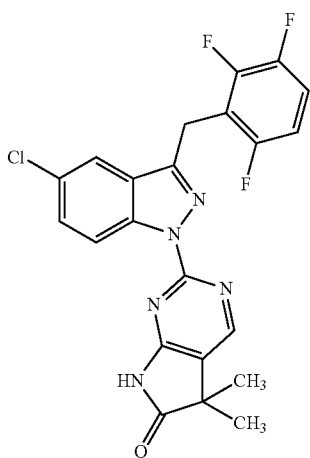 [SMILES: CC1(C)C(=O)Nc2nc(-n3nc(Cc4c(F)ccc(F)c4F)c4cc(Cl)ccc43)ncc21]

A solution of 52 mg (0.089 mmol) of Example 1 in DMF (9 ml) was added to 21.4 mg of palladium on charcoal (10%) in DMF (1 ml), and hydrogenation was effected at standard hydrogen pressure for 5 h. Subsequently, the mixture was filtered through Celite, washed with DMF and concentrated to dryness. The residue was purified by means of preparative HPLC (acetonitrile:water (+0.05% formic acid) gradient). 29 mg of the title compound were obtained (66% of theory).

LC-MS (Method 2): $R_t$=1.28 min; MS (ESIpos): m/z=458 (M+H)$^+$ $^1$H NMR (400 MHz, DMSO-d$_6$): δ [ppm]=1.36 (s, 6H), 4.49 (s, 2H), 7.19-7.23 (m, 1H), 7.46-7.53 (m, 1H), 7.65 (dd, 1H), 8.00 (d, 1H), 8.52 (s, 1H), 8.65 (d, 1H), 11.72 (s, 1H).

Example 3

2-[3-(2-Fluorobenzyl)-1H-indazol-1-yl]-4-iodo-5,5-dimethyl-5,7-dihydro-6H-pyrrolo[2,3-d]pyrimidin-6-one

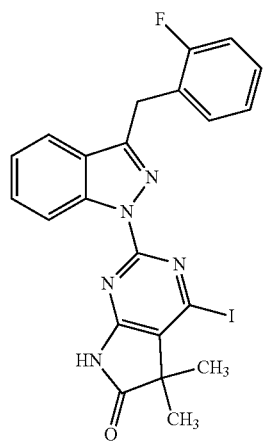 [SMILES: CC1(C)C(=O)Nc2nc(-n3nc(Cc4ccccc4F)c4ccccc43)nc(I)c21]

500 mg (1.242 mmol) of Example 7A were initially charged in isopentyl nitrite (3.552 ml) and diiodomethane (9,430 ml), and the mixture was heated to 85° C. overnight. After cooling, the reaction mixture was filtered through silica gel (dichloromethane:methanol gradient) and concentrated. The residue was admixed with dichloromethane and methanol, and stirred at room temperature for 10 min. The solids formed were filtered off and washed with dichloromethane and methanol. The filtrate was concentrated. This residue was then admixed with methanol and acetonitrile. A precipitate was again formed, which was filtered off with suction and washed with acetonitrile. After drying under high vacuum, 127 mg of the title compound were obtained (18% of theory). The filtrate was concentrated; thus, a further 334 mg of the title compound were obtained in 57% purity (30% of theory).

LC-MS (Method 1): $R_t$=1.31 min; MS (ESIpos): m/z=514 (M+H)$^+$ $^1$H NMR (400 MHz, DMSO-d$_6$): δ [ppm]=1.42 (s, 6H), 4.43 (s, 2H), 7.13-7.23 (m, 2H), 7.29-7.41 (m, 3H), 7.62 (t, 1H), 7.74 (d, 1H), 8.58 (d, 1H), 11.89 (s, 1H).

As well as the title compound, 57 mg (9% of theory, 86% purity) of 2-[3-(2-fluorobenzyl)-1H-indazol-1-yl]-4-hydroxy-5,5-dimethyl-5,7-dihydro-6H-pyrrolo[2,3-d]pyrimidin-6-one (Example 4) were obtained.

Example 5

2-[3-(2-Fluorobenzyl)-1H-indazol-1-yl]-5,5-dimethyl-5,7-dihydro-6H-pyrrolo[2,3-d]pyrimidin-6-one

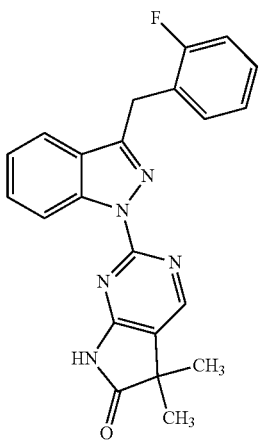 [SMILES: CC1(C)C(=O)Nc2nc(-n3nc(Cc4ccccc4F)c4ccccc43)ncc21]

60 mg (0.117 mmol) of Example 3 were hydrogenated in analogy to the method in Example 2. 14 mg of the title compound were obtained (45% of theory).

LC-MS (Method 2): $R_t$=1.13 min; MS (ESIpos): m/z=388 (M+H)$^+$ $^1$H NMR (400 MHz, DMSO-d$_6$): δ [ppm]=1.38 (s, 6H), 4.42 (s, 2H), 7.14-7.22 (m, 2H), 7.28-7.33 (m, 2H), 7.40 (t, 1H), 7.57 (t, 1H), 7.76 (d, 1H), 8.54 (s, 1H), 8.67 (d, 1H), 11.71 (s, 1H).

Example 6

2-[5-Fluoro-3-(2-fluorobenzyl)-1H-indazol-1-yl]-4-iodo-5,5-dimethyl-5,7-dihydro-6H-pyrrolo[2,3-d]pyrimidin-6-one

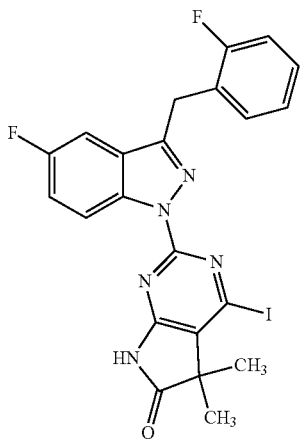 [SMILES: CC1(C)C(=O)Nc2nc(-n3nc(Cc4ccccc4F)c4cc(F)ccc43)nc(I)c21]

500 mg (1.189 mmol) of Example 11A were initially charged in isopentyl nitrite (340 ml) and diiodomethane (9,027 ml), and the mixture was heated to 85° C. overnight. After cooling, the mixture was filtered through silica gel (dichloromethane:methanol gradient) and concentrated. The residue was purified by means of preparative HPLC (acetonitrile:water (+0.05% formic acid) gradient). 274 mg of the title compound were obtained (43% of theory).

LC-MS (Method 1): $R_t$=1.33 min; MS (ESIpos): m/z=532 (M+H)$^+$ $^1$H NMR (400 MHz, DMSO-d$_6$): δ [ppm]=1.41 (s, 6H), 4.41 (s, 2H), 7.14-7.23 (m, 2H), 7.29-7.35 (m, 1H), 7.39-7.43 (ddd, 1H), 7.52-7.61 (m, 2H), 8.58 (d, 1H), 11.91 (s, 1H).

As well as the title compound, 72 mg (14% of theory, 83% purity) of 2-[5-fluoro-3-(2-fluorobenzyl)-1H-indazol-1-yl]-4-hydroxy-5,5-dimethyl-5,7-dihydro-6H-pyrrolo[2,3-d]pyrimidin-6-one (Example 7) were obtained.

Example 8

2-[5-Fluoro-3-(2-fluorobenzyl)-1H-indazol-1-yl]-5,5-dimethyl-5,7-dihydro-6H-pyrrolo[2,3-d]pyrimidin-6-one

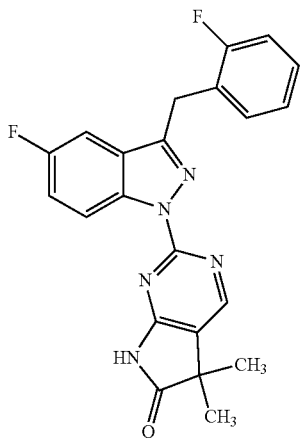 [SMILES: CC1(C)C(=O)Nc2nc(-n3nc(Cc4ccccc4F)c4cc(F)ccc43)ncc21]

60 mg (0.113 mmol) of Example 6 were hydrogenated in analogy to the method in Example 2. 34 mg of the title compound were obtained (76% of theory).

LC-MS (Method 1): $R_t$=1.16 min; MS (ESIpos): m/z=406 (M+H)$^+$ $^1$H NMR (400 MHz, DMSO-d$_6$): δ [ppm]=1.38 (s, 6H), 4.41 (s, 2H), 7.15-7.23 (m, 2H), 7.29-7.34 (m, 1H), 7.40-7.46 (m, 1H), 7.47-7.51 (m, 1H), 7.58 (dd, 1H), 8.53 (s, 1H), 8.67 (dd, 1H), 11.73 (s br, 1H).

Example 9

3-[6-Fluoro-3-(2-fluorobenzyl)-1H-pyrazolo[4,3-b]pyridin-1-yl]-7,7-dimethyl-5,7-dihydro-6H-pyrrolo[2,3-e][1,2,4]triazin-6-one

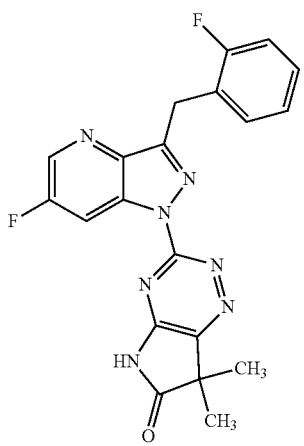 [SMILES: CC1(C)C(=O)Nc2nc(-n3nc(Cc4ccccc4F)c4ncc(F)cc43)nnc21]

66 mg (0.125 mmol) of Example 49A were dissolved in 4 ml of acetonitrile and 1 ml of water, and 68 mg (0.125 mmol) of ammonium cerium(IV) nitrate were added and the mixture was stirred at RT for 1.5 h. After adding a further 68 mg of ammonium cerium(IV) nitrate, the mixture was stirred at RT overnight. Another 68 mg of ammonium cerium(IV) nitrate were added and the mixture was stirred at RT for 1.5 h, and this procedure was repeated once more. Finally, 55.5 mg (0.750 mmol) of sodium hydrogensulphide hydrate were added, and the mixture was stirred at RT for a further 30 min and left to stand for 2 d. The reaction mixture was diluted with acetonitrile and filtered through kieselguhr. The filtrate was concentrated and the residue was purified by preparative HPLC (Reprosil C18, gradient of acetonitrile/0.01% aq. formic acid).

Yield: 18 mg (35% of theory)

LC-MS (Method 1): $R_t$=1.03 min; MS (ESIpos): m/z=408 (M+H)$^+$ $^1$H NMR (500 MHz, DMSO-$d_6$) δ [ppm]=1.45 (s, 6H), 4.48 (s, 2H), 7.10-7.23 (m, 2H), 7.30 (q, 1H), 7.42 (t, 1H), 8.70 (d, 1H), 8.70 (d, 1H), 8.77 (br. s., 1H), 12.38 (br. s., 1H)

Example 10

2-[1-(2-Fluorobenzyl)-1,4,5,6-tetrahydrocyclopenta [c]pyrazol-3-yl]-4-iodo-5,5-dimethyl-5,7-dihydro-6H-pyrrolo[2,3-d]pyrimidin-6-one

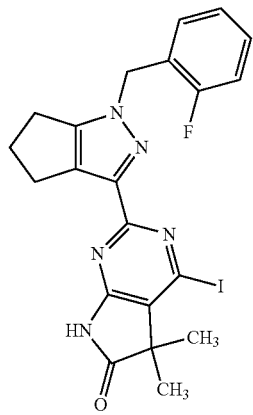 [SMILES: CC1(C)C(=O)Nc2nc(-c3nn(Cc4ccccc4F)c4c3CCC4)nc(I)c21]

285 mg (0.68 mmol) of 4-amino-2-[1-(2-fluorobenzyl)-1, 4,5,6-tetrahydrocyclopenta[c]pyrazol-3-yl]-5,5-dimethyl-5, 7-dihydro-6H-pyrrolo[2,3-d]pyrimidin-6-one were initially charged in absolute dimethoxyethane, and 800 mg (6.83 mmol) of isopentyl nitrite, 87 mg (0.34 mmol) of iodine, 39 mg (0.21 mmol) of copper(I) iodide and 177 mg (0.68 mmol) of caesium iodide were added. The mixture was stirred at 100° C. for 40 min. The mixture was concentrated on a rotary evaporator, and the residue was taken up in dichloromethane and washed with 5% aqueous sodium thiosulphate solution and saturated aqueous sodium chloride solution. The organic phase was dried over sodium sulphate, concentrated and purified by means of preparative HPLC (eluent: acetonitrile/water with 0.1% acetic acid, gradient 20:80→100:0). 148 mg (40% of theory) of the target compound were obtained.

LC-MS (Method 1): $R_t$=1.23 min; MS (ESIpos): m/z=504 (M+H)$^+$

Example 11

2-[1-(2-Fluorobenzyl)-1,4,5,6-tetrahydrocyclopenta [c]pyrazol-3-yl]-5,5-dimethyl-5,7-dihydro-6H-pyrrolo[2,3-d]pyrimidin-6-one

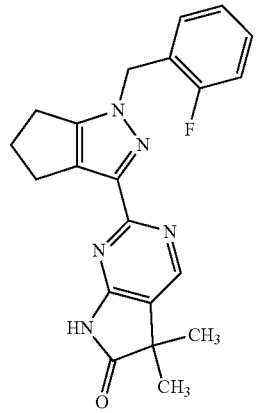 [SMILES: CC1(C)C(=O)Nc2nc(-c3nn(Cc4ccccc4F)c4c3CCC4)ncc21]

45 mg (0.08 mmol) of 2-[1-(2-fluorobenzyl)-1,4,5,6-tetrahydrocyclopenta[c]pyrazol-3-yl]-4-iodo-5,5-dimethyl-5, 7-dihydro-6H-pyrrolo[2,3-d]pyrimidin-6-one were dissolved in 5 ml of absolute DMF, 18 mg (0.02 mmol) of 10% palladium on charcoal were added and hydrogenation was effected under standard hydrogen pressure overnight. The reaction mixture was filtered through Celite and concentrated, and the residue was purified by means of preparative HPLC (eluent: acetonitrile/water, gradient 20:80→100:0). 25 mg of the target compound were obtained (80% of theory).

LC-MS (Method 1): $R_t$=0.99 min; MS (ESIpos): m/z=378 (M+H)$^+$ $^1$H NMR (400 MHz, DMSO-$d_6$): δ [ppm]=1.36 (s, 6H), 2.64-2.68 (m, 2H), 2.79-2.82 (m, 2H), 5.41 (s, 2H), 7.21-7.32 (m, 3H), 7.39-7.45 (m, 1H), 8.56 (s, 1H), 12.00 (s br, 1H).

Example 12

3-[1-(2-Fluorobenzyl)-1,4,5,6-tetrahydrocyclopenta [c]pyrazol-3-yl]-7,7-dimethyl-5,7-dihydro-6H-pyrrolo[2,3-e][1,2,4]triazin-6-one

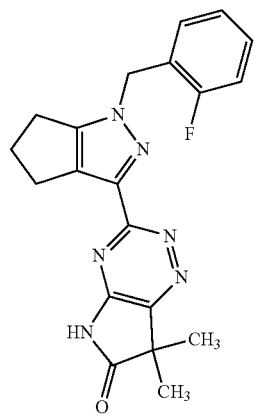 [SMILES: CC1(C)C(=O)Nc2nc(-c3nn(Cc4ccccc4F)c4c3CCC4)nnc21]

48 mg (0.06 mmol, purity 54%) of methyl 2-{3-[1-(2-fluorobenzyl)-1,4,5,6-tetrahydrocyclopenta[c]pyrazol-3-yl]-5-hydroxy-1,2,4-triazin-6-yl}-2-methylpropanoate were admixed with 0.5 ml (5.36 mmol) of phosphoryl chloride and the mixture was stirred at RT for 2.5 h. The reaction solution was diluted with 10 ml of dry acetonitrile and gradually added dropwise while cooling with ice to 5 ml of a 25% aqueous ammonia solution, and the mixture was stirred at RT for 8 h. The reaction mixture was concentrated on a rotary evaporator and the residue was partitioned between dichloromethane/water. The organic phase was dried over sodium sulphate and concentrated on a rotary evaporator. The residue was purified by means of preparative HPLC (eluent: acetonitrile/water with 0.1% hydrochloric acid, gradient 20:80→100:0). 4.5 mg of the target compound were obtained (18% of theory).

LC-MS (Method 1): $R_t$=0.96 min; MS (ESIpos): m/z=379 (M+H)$^+$ $^1$H NMR (400 MHz, DMSO-d$_6$): δ [ppm]=1.40 (s, 6H), 2.66-2.70 (m, 2H), 2.79-2.83 (m, 2H), 5.36 (s, 2H), 7.19-7.31 (m, 3H), 7.37-7.43 (m, 1H), 12.00 (s br, 1H).

Example 13

2-[1-(2-Fluorobenzyl)-6-methyl-1H-pyrazolo[3,4-d]pyrimidin-3-yl]-4-iodo-5,5-dimethyl-5,7-dihydro-6H-pyrrolo[2,3-d]pyrimidin-6-one

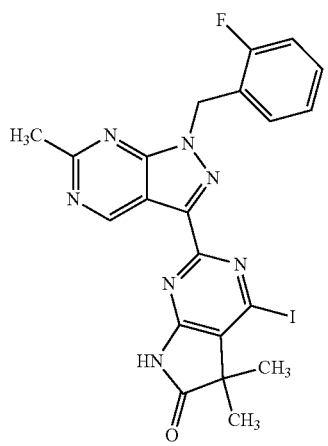 [SMILES: Cc1ncc2c(-c3nc(I)c4c(n3)NC(=O)C4(C)C)nn(Cc3ccccc3F)c2n1]

70 mg (0.17 mmol) of 4-amino-2-[1-(2-fluorobenzyl)-6-methyl-1H-pyrazolo[3,4-d]pyrimidin-3-yl]-5,5-dimethyl-5,7-dihydro-6H-pyrrolo[2,3-d]pyrimidin-6-one were admixed with 3.770 g (14.08 mmol) of diiodomethane and 411 mg (3.51 mmol) of isopentyl nitrite. The mixture was stirred at 85° C. for 8 h. After cooling, the mixture was diluted with acetonitrile and purified by means of preparative HPLC (eluent: acetonitrile/water with, gradient 30:70→95:5). 35 mg (24% of theory) of the target compound were obtained.

LC-MS (Method 3): $R_t$=2.37 min; MS (ESIpos): m/z=530 (M+H)$^+$

In addition, 10 mg (14% of theory) of 2-[1-(2-fluorobenzyl)-6-methyl-1H-pyrazolo[3,4-d]pyrimidin-3-yl]-4-hydroxy-5,5-dimethyl-5,7-dihydro-6H-pyrrolo[2,3-d]pyrimidin-6-one (see Example 20) were obtained.

Example 14

2-[1-(2,3-Difluorobenzyl)-6-methyl-1H-pyrazolo[3,4-d]pyrimidin-3-yl]-4-iodo-5,5-dimethyl-5,7-dihydro-6H-pyrrolo[2,3-d]pyrimidin-6-one

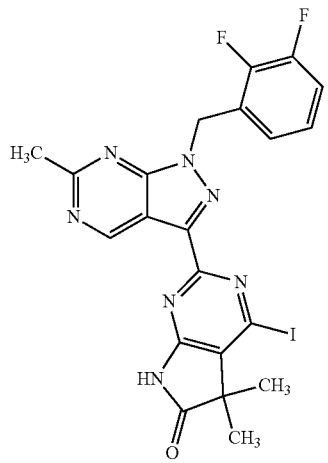 [SMILES: Cc1ncc2c(-c3nc(I)c4c(n3)NC(=O)C4(C)C)nn(Cc3cccc(F)c3F)c2n1]

150 mg (0.34 mmol) of 4-amino-2-[1-(2,3-difluorobenzyl)-6-methyl-1H-pyrazolo[3,4-d]pyrimidin-3-yl]-5,5-dimethyl-5,7-dihydro-6H-pyrrolo[2,3-d]pyrimidin-6-one were admixed with 6.650 g (19.86 mmol) of diiodomethane and 402 mg (3.44 mmol) of isopentyl nitrite. The mixture was stirred at 85° C. for 8 h. 70 mg (0.69 mmol) of triethylamine were added and the mixture was again boiled under reflux at 85° C. After cooling, the mixture was diluted with acetonitrile and purified by means of preparative HPLC (eluent: acetonitrile/water with, gradient 30:70→95:5). 44 mg (purity 67%, 16% of theory) of the target compound were obtained.

LC-MS (Method 1): $R_t$=1.14 min; MS (ESIpos): m/z=548 (M+H)$^+$

Example 15

2-[1-(2-Fluorobenzyl)-6-methyl-1H-pyrazolo[3,4-d]pyrimidin-3-yl]-5,5-dimethyl-5,7-dihydro-6H-pyrrolo[2,3-d]pyrimidin-6-one

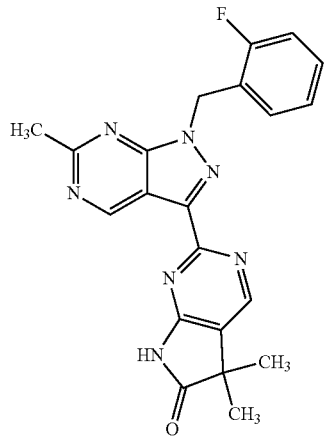 [SMILES: Cc1ncc2c(-c3ncc4c(n3)NC(=O)C4(C)C)nn(Cc3ccccc3F)c2n1]

35 mg (0.07 mmol) of 2-[1-(2-fluorobenzyl)-6-methyl-1H-pyrazolo[3,4-d]pyrimidin-3-yl]-4-iodo-5,5-dimethyl-5,7-dihydro-6H-pyrrolo[2,3-d]pyrimidin-6-one were dissolved in 8 ml of absolute DMF, 50 mg of 10% palladium on charcoal were added and hydrogenation was effected under standard hydrogen pressure overnight. The reaction mixture was filtered through Celite and concentrated. The residue was stirred with 1 ml of acetonitrile and filtered with suction, and the solids were dried under high vacuum. 5 mg of the target compound were obtained (purity 92%; 17% of theory).

Example 16

3-[1-(2-Fluorobenzyl)-6-methyl-1H-pyrazolo[3,4-d]pyrimidin-3-yl]-7,7-dimethyl-5,7-dihydro-6H-pyrrolo[2,3-e][1,2,4]triazin-6-one

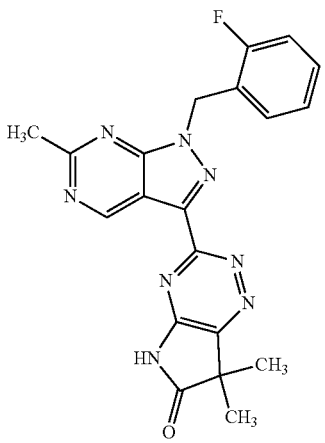 [SMILES: Cc1ncc2c(-c3nnc4c(n3)NC(=O)C4(C)C)nn(Cc3ccccc3F)c2n1]

182 mg (0.42 mmol) of methyl 2-{3-[1-(2-fluorobenzyl)-6-methyl-1H-pyrazolo[3,4-d]pyrimidin-3-yl]-5-hydroxy-1,2,4-triazin-6-yl}-2-methylpropanoate were admixed with 3.8 ml (40.87 mmol) of phosphoryl chloride and the mixture was stirred at RT for 2.5 h. The reaction solution was diluted with 20 ml of dry acetonitrile and gradually added dropwise while cooling with ice to 40 ml of a 25% aqueous ammonia solution, and the mixture was stirred at RT for 2 h. The reaction mixture was concentrated on a rotary evaporator and the precipitate was filtered off. The residue was stirred with DMF/methanol and filtered with suction, and the solids were dried under high vacuum. 98 mg of the target compound were obtained (purity 92%; 53% of theory).

LC-MS (Method 2) $R_t$=0.89 min; MS (ESIpos): m/z=405 (M+H)$^+$ $^1$H NMR (400 MHz, DMSO-$d_6$): δ [ppm]=1.45 (s, 6H), 2.81 (s, 3H), 5.81 (s, 2H), 7.16-7.31 (m, 3H), 7.36-7.42 (m, 1H), 9.71 (s, 1H), 12.21 (s, 1H).

Example 17

2-[1-(2,3-Difluorobenzyl)-6-methyl-1H-pyrazolo[3,4-d]pyrimidin-3-yl]-5,5-dimethyl-5,7-dihydro-6H-pyrrolo[2,3-d]pyrimidin-6-one

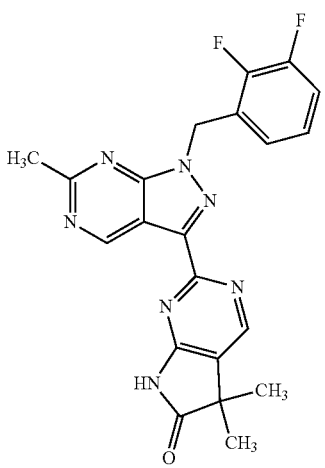 [SMILES: Cc1ncc2c(-c3ncc4c(n3)NC(=O)C4(C)C)nn(Cc3cccc(F)c3F)c2n1]

44 mg (0.05 mmol) of 2-[1-(2,3-difluorobenzyl)-6-methyl-1H-pyrazolo[3,4-d]pyrimidin-3-yl]-4-iodo-5,5-dimethyl-5,7-dihydro-6H-pyrrolo[2,3-d]pyrimidin-6-one were dissolved in 8 ml of absolute DMF, 11 mg (0.01 mmol) of 10% palladium on charcoal were added and hydrogenation was effected under standard hydrogen pressure for 4 h. The reaction mixture was filtered and purified by means of preparative HPLC (eluent: acetonitrile/water, gradient 20:80→100:0). 6 mg of the target compound were obtained (purity 81%; 21% of theory).

LC-MS (Method 1): $R_t$=0.95 min; MS (ESIpos): m/z=422 (M+H)$^+$ $^1$H NMR (400 MHz, DMSO-$d_6$): δ [ppm]=1.38 (s, 6H), 2.80 (s, 3H), 5.83 (s, 2H), 7.09-7.11 (m, 1H), 7.17-7.22 (m, 1H), 7.39-7.46 (m, 1H), 8.67 (s, 1H), 9.73 (s, 1H), 11.64 (s, 1H).

Example 18

3-[1-(2,3-Difluorobenzyl)-6-methyl-1H-pyrazolo[3,4-d]pyrimidin-3-yl]-7,7-dimethyl-5,7-dihydro-6H-pyrrolo[2,3-e][1,2,4]triazin-6-one

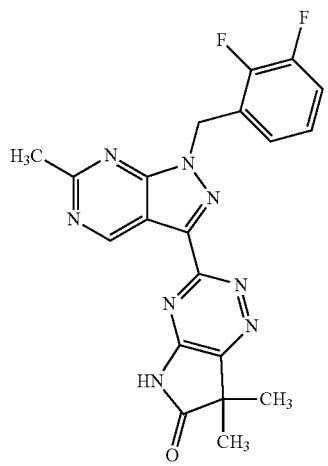 [SMILES: Cc1ncc2c(-c3nnc4c(n3)NC(=O)C4(C)C)nn(Cc3cccc(F)c3F)c2n1]

160 mg (purity 89%, 0.313 mmol) of methyl 2-{3-[1-(2,3-difluorobenzyl)-6-methyl-1H-pyrazolo[3,4-d]pyrimidin-3-yl]-5-hydroxy-1,2,4-triazin-6-yl}-2-methylpropanoate were admixed with 4 ml (42.913 mmol) of phosphoryl chloride and the mixture was stirred at RT for 2.5 h. The reaction solution was diluted with 20 ml of dry acetonitrile and gradually added dropwise while cooling with ice to 40 ml of a 25% aqueous ammonia solution, and the mixture was stirred at RT for 1 h. The reaction mixture was concentrated on a rotary evaporator and the precipitate was filtered off. The residue was stirred with hot ethanol/water and filtered with suction, and the solids were dried under high vacuum. 70 mg of the target compound were obtained (52% of theory).

LC-MS (Method 1): $R_t$=0.92 min; MS (ESIpos): m/z=423 (M+H)$^+$ $^1$H NMR (400 MHz, DMSO-$d_6$): δ [ppm]=1.46 (s, 6H), 2.81 (s, 3H), 5.86 (s, 2H), 7.09-7.19 (m, 1H), 7.17-7.23 (m, 1H), 7.39-7.46 (m, 1H), 9.71 (s, 1H), 12.24 (s br, 1H).

Example 19

3-[1-(2-Fluorobenzyl)-1H-pyrazolo[3,4-d]pyrimidin-3-yl]-7,7-dimethyl-5,7-dihydro-6H-pyrrolo[2,3-e][1,2,4]triazin-6-one

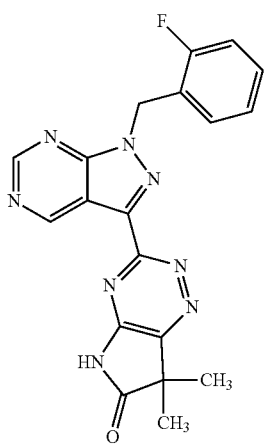 [SMILES: CC1(C)C(=O)Nc2nc(-c3nn(Cc4ccccc4F)c4ncncc34)nnc21]

186 mg (0.438 mmol) of methyl 2-{3-[1-(2-fluorobenzyl)-1H-pyrazolo[3,4-d]pyrimidin-3-yl]-5-hydroxy-1,2,4-triazin-6-yl}-2-methylpropanoate were admixed with 4 ml (42.913 mmol) of phosphoryl chloride and the mixture was stirred at RT for 2.5 h. The reaction solution was diluted with 20 ml of dry acetonitrile and gradually added dropwise while cooling with ice to 30 ml of a 25% aqueous ammonia solution, and the mixture was stirred at RT overnight. The reaction mixture was concentrated on a rotary evaporator and the precipitate was filtered off. 127 mg of the target compound were obtained (74% of theory).

LC-MS (Method 2) Rt=0.85 min; MS (ESIpos): m/z=391 (M+H)+

$^1$H NMR (400 MHz, DMSO-d6): δ [ppm]=1.45 (s, 6H), 5.87 (s, 2H), 7.17-7.26 (m, 2H), 7.32-7.42 (m, 2H), 9.21 (s, 1H), 9.83 (s, 1H).

Example 21

3-[5-Fluoro-3-(2-fluorobenzyl)-1H-indazol-1-yl]-7,7-dimethyl-5,7-dihydro-6H-pyrrolo[2,3-e][1,2,4]triazin-6-one

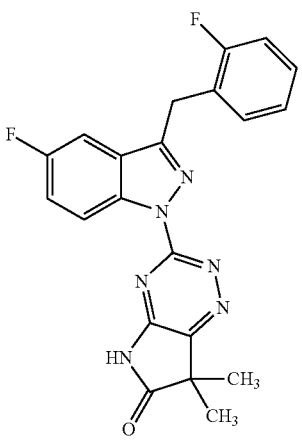 [SMILES: CC1(C)C(=O)Nc2nc(-n3nc(Cc4ccccc4F)c4cc(F)ccc43)nnc21]

100 mg (0.41 mmol) of Example 50A were dissolved in 0.5 ml of NMP, 122 mg (0.614 mmol) of Example 47A were added and the mixture was stirred at 80° C. overnight. Thereafter, 50 mg (0.2 mmol) of Example 47A were added and the mixture was stirred at 100° C. for 3 h, then 0.5 ml of NMP and 50 mg (0.2 mmol) of Example 47A were added and the mixture was stirred at 100° C. for 1 h, and finally 26 mg (0.1 mmol) of Example 47A were added and the mixture was stirred at 100° C. for 3 h. After cooling, the mixture was combined with a test batch of 10 mg (0.041 mmol) of Example 47A, a little aq. 5 M aqueous formic acid was added and the precipitated solids were removed. The filtrate was purified by means of preparative HPLC (Reprosil C18, gradient of acetonitrile/0.01% aq. formic acid) and the product-containing fractions were concentrated. The residue was digested with acetonitrile on an ultrasound bath and then filtered off.

Yield: 63.5 mg, solid, (35% of theory)

LC-MS (Method 1): $R_t$=1.11 min; MS (ESIpos): m/z=407 (M+H)$^+$ $^1$H NMR (400 MHz, DMSO-d$_6$) δ 8 ppm]=1.45 (s, 6H), 4.43 (s, 2H), 7.11-7.25 (m, 2H), 7.27-7.36 (m, 1H), 7.44 (t, 1H), 7.54 (t, 1H), 7.64 (d, 1H), 8.60-8.73 (m, 1H), 12.33 (br. s, 1H).

Example 22

3-[5-Fluoro-3-(3,3,4,4,4-pentafluorobutyl)-1H-indazol-1-yl]-7,7-dimethyl-5,7-dihydro-6H-pyrrolo[2,3-e][1,2,4]triazin-6-one

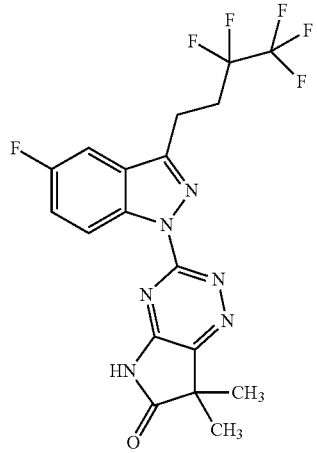 [SMILES: CC1(C)C(=O)Nc2nc(-n3nc(CCC(F)(F)C(F)(F)F)c4cc(F)ccc43)nnc21]

A solution of 33.5 mg (0.06 mmol) of Example 52A in 1 ml of acetonitrile was admixed at 0-4° C. with a precooled solution of 97.6 mg (0.18 mmol) of ammonium cerium(IV) nitrate in 0.25 ml of water, and stirred within this temperature range for 1 h and at RT overnight. Then a further 97.6 mg (0.18 mmol) of ammonium cerium(IV) nitrate were added in solid form and the mixture was stirred at RT for 3 h. Ethyl acetate was added, the mixture was washed twice with saturated aqueous sodium chloride solution, and the combined aqueous phases were extracted once again with ethyl acetate. The combined organic phases were dried and concentrated. The residue was purified by preparative HPLC (Reprosil C18, gradient of acetonitrile/0.01% aq. formic acid).

Yield: 9.7 mg (37% of theory)

LC-MS (Method 1): $R_t$=1.14 min; MS (ESIpos): m/z=445 (M+H)$^+$ $^1$H NMR (400 MHz, DMSO-d$_6$) δ [ppm]=1.46 (s, 6H), 2.72-2.94 (m, 2H), 7.51-7.62 (m, 1H), 7.85-7.94 (m, 1H), 8.59-8.74 (m, 1H), 12.34 (br.s., 1H), one CH$_2$ group partially covered by the water signal.

Example 23

4-Ethyl-2-[5-fluoro-3-(2-fluorobenzyl)-1H-indazol-1-yl]-5,5-dimethyl-5,7-dihydro-6H-pyrrolo[2,3-d]pyrimidin-6-one

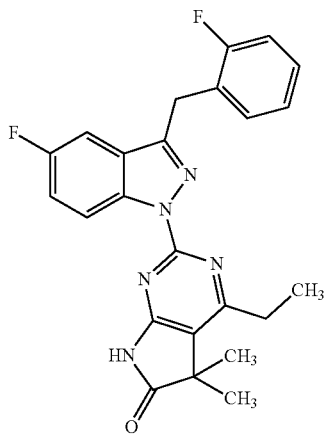 [SMILES: CCc1nc(-n2nc(Cc3ccccc3F)c3cc(F)ccc32)nc2c1C(C)(C)C(=O)N2]

A solution of 50 mg (0.09 mmol) of Example 6 in 2 ml of dioxane at RT was evacuated and filled with argon three times, 2 mg (2.2 μm) of [1,1'-bis(diphenylphosphine)ferrocene]dichloropalladium(II) complex with dichloromethane were added, and the mixture was evacuated and filled again with argon. Then 340 μl of diethylzinc (15% in toluene) were added dropwise within approx. 2 min, and the mixture was stirred at RT for 10 min and at 90° C. for 16 h. Another 500 μl of diethylzinc (15% in toluene) were added to the suspension at RT within 2 min, and the mixture was stirred at 90° C. overnight. This procedure is repeated twice more with 300 μl of diethylzinc (15% in toluene) each time, with addition of a further 3 mg (3.7 μm) of [1,1'-bis(diphenylphosphine)ferrocene]dichloropalladium(II) complex with dichloromethane in the last metered addition. The reaction mixture was admixed with 2 ml of water and stirred at RT for 1 h. The dioxane was removed under reduced pressure and, after adding ethyl acetate and water, the inorganic solids were filtered off. The phases were separated, the water phase was extracted twice more with ethyl acetate, and the combined organic phases were dried and concentrated. The residue was purified by preparative HPLC (Reprosil C18, gradient of acetonitrile/0.1% aq. formic acid).

Yield: 10.5 mg (26% of theory).

LC-MS (Method 1): $R_t$=1.14 min; MS (ESIpos): m/z=434 (M+H)$^+$ $^1$H NMR (400 MHz, DMSO-d$_6$) δ [ppm]=1.30-1.52 (m, 9H), 2.81 (q, 2H), 4.41 (s, 2H), 7.10-7.25 (m, 2H), 7.27-7.44 (m, 2H), 7.46-7.64 (m, 2H), 8.73 (dd, 1H), 11.72 (br. s., 1H).

Example 24

3-[6-Chloro-1-(2-fluorobenzyl)-1H-indazol-3-yl]-7,7-dimethyl-5,7-dihydro-6H-pyrrolo[2,3-e][1,2,4]triazin-6-one

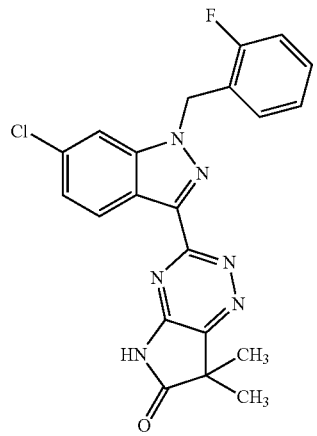 [SMILES: CC1(C)C(=O)Nc2nc(-c3nn(Cc4ccccc4F)c4cc(Cl)ccc34)nnc21]

198 mg of solids and 527 mg of crude substance (theoretically 1.28 mmol) from Example 56A were stirred in 10 ml (107.3 mmol) of phosphoryl chloride at room temperature overnight. The intermediate, methyl 2-{5-chloro-3-[6-chloro-1-(2-fluorobenzyl)-1H-indazol-3-yl]-1,2,4-triazin-6-yl}-2-methylpropanoate, was detected by means of LC-MS:

LC-MS (Method 1): $R_t$=1.39 min; MS (ESIpos): m/z=473 (M+H)$^+$.

The reaction mixture was diluted with 50 ml of acetonitrile and slowly added dropwise at 0° C. to 70 ml of 33% aq. ammonia solution (temperature rise up to 12° C.). After stirring at room temperature for one night, the phases were separated, and the aqueous phase was extracted twice with ethyl acetate. The combined organic phases were washed once with saturated sodium chloride solution, dried over sodium sulphate, concentrated under reduced pressure and purified by means of preparative HPLC (gradient 0.05% formic acid in water/20-95% acetonitrile). 203.4 mg (38% of theory) of the title compound were obtained.

LC-MS (Method 1): $R_t$=1.13 min; MS (ESIpos): m/z=423 (M+H)$^+$ $^1$H NMR (400 MHz, DMSO-d$_6$): δ [ppm]=1.45 (s, 6H), 5.87 (s, 2H), 7.10-7.30 (m, 3H), 7.33-7.45 (m, 2H), 8.11 (s, 1H), 8.51 (d, 1H), 12.15 (s, 1H).

Example 25

3-[6-Chloro-1-[(3-fluoropyridin-2-yl)methyl]-1H-indazol-3-yl]-7,7-dimethyl-5,7-dihydro-6H-pyrrolo[2,3-e][1,2,4]triazin-6-one

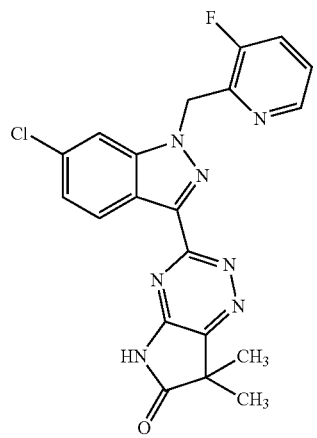 [SMILES: CC1(C)C(=O)Nc2nc(-c3nn(Cc4ncccc4F)c4cc(Cl)ccc34)nnc21]

685 mg of crude substance from Example 60A were converted in analogy to Example 24. 202 mg of the title compound were obtained (39% of theory).

LC-MS (Method 1): $R_t$=1.01 min; MS (ESIpos): m/z=424 (M+H)$^+$ $^1$H NMR (400 MHz, DMSO-d$_6$): δ [ppm]=1.45 (s, 6H), 6.01 (s, 2H), 7.39 (dd, 1H), 7.43-7.49 (m, 1H), 7.73-7.85 (m, 1H), 8.04-8.14 (m, 1H), 8.31 (d, 1H), 8.50 (d, 1H), 12.13 (s, 1H).

Example 26

3-[6-Chloro-1-(3,3,4,4,4-pentafluorobutyl)-1H-indazol-3-yl]-7,7-dimethyl-5,7-dihydro-6H-pyrrolo[2,3-e][1,2,4]triazin-6-one

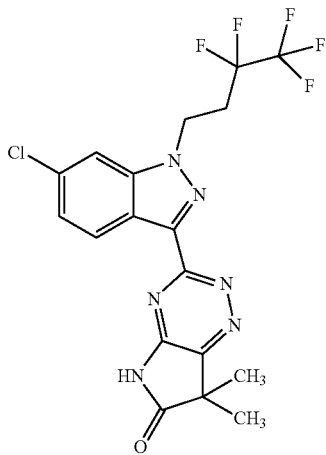 [SMILES: CC1(C)C(=O)Nc2nc(-c3nn(CCC(F)(F)C(F)(F)F)c4cc(Cl)ccc34)nnc21]

488 mg (0.99 mmol) of Example 62A (crude product) were converted analogously to Example 24. The intermediate, methyl 2-[5-chloro-3-[6-chloro-1-(3,3,4,4,4-pentafluorobutyl)-1H-indazol-3-yl]-1,2,4-triazin-6-yl]-2-methylpropanoate, was detected by means of LC-MS: LC-MS (Method 1): $R_t$=1.39 min; MS (ESIpos): m/z=512 (M+H)$^+$. 180 mg (38% of theory) of the title compound were obtained.

LC-MS (Method 1): $R_t$=1.15 min; MS (ESIpos): m/z=461 (M+H)$^+$ $^1$H NMR (400 MHz, DMSO-d$_6$): [ppm]=1.46 (s, 6H), 2.85-3.07 (m, 2H), 4.90 (t, 2H), 7.34-7.44 (m, 1H), 8.13 (d, 1H), 8.51 (d, 1H), 12.17 (s, 1H).

Example 27

2-[5-Fluoro-3-(2-fluorobenzyl)-1H-indazol-1-yl]-4,5,5-trimethyl-5,7-dihydro-6H-pyrrolo[2,3-d]pyrimidin-6-one

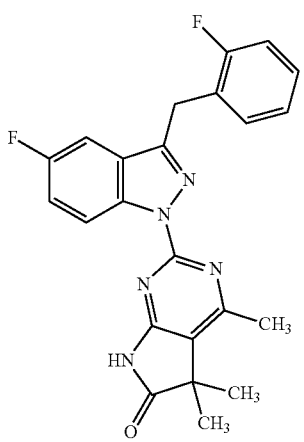 [SMILES: Cc1nc(-n2nc(Cc3ccccc3F)c3cc(F)ccc32)nc2c1C(C)(C)C(=O)N2]

Under argon, 60 mg (0.11 mmol) of Example 6 were initially charged in 2 ml of dioxane, 2.3 mg (2.8 mmol) of PdCl$_2$(dppf)xCH$_2$Cl$_2$ were added and 0.23 ml of a 2 M solution of dimethylzinc in toluene was added dropwise, and the mixture was heated in a microwave to 120° C. for 3 h 25 min. Another 3 mg (3.7 mmol) of PdCl$_2$(dppf)$_x$CH$_2$Cl$_2$ and 0.23 ml of the 2 M dimethylzinc solution in toluene were added and the mixture was stirred in the microwave at 120° C. for 3 h. 3 ml of water were added cautiously and the mixture was concentrated under reduced pressure. The residue was taken up in acetonitrile and 5 M aq. formic acid and filtered, and the filtrate was purified by means of preparative HPLC (gradient 0.1% formic acid in water/10-95% acetonitrile).

Yield: 20 mg (42% of theory)

LC-MS (Method 1): $R_t$=1.21 min; MS (ESIpos): m/z=420 (M+H)$^+$ $^1$H NMR (400 MHz, DMSO-d$_6$): δ [ppm]=1.39 (s, 6H), 4.40 (s, 2H), 7.12-7.24 (m, 2H), 7.26-7.34 (m, 1H), 7.35-7.42 (m, 1H), 7.43-7.51 (m, 1H), 7.52-7.59 (m, 1H), 8.69-8.78 (m, 1H), 11.66 (br. s, 1H).

Example 28

2-[3-(2-Fluorobenzyl)-1H-indazol-1-yl]-5,5-dimethyl-4-propyl-5,7-dihydro-6H-pyrrolo[2,3-d]-pyrimidin-6-one

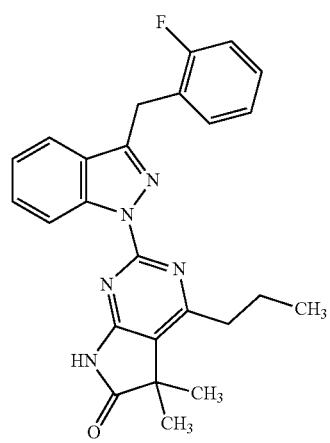 [SMILES: CCCc1nc(-n2nc(Cc3ccccc3F)c3ccccc32)nc2c1C(C)(C)C(=O)N2]

Analogously to the method of Example 27, 200 mg (0.39 mmol) of the compound from Example 3 were reacted with 3.12 ml (1.56 mmol) of a 0.5 M solution of propylzinc bromide in THF. Purification by means of preparative HPLC (gradient 0.1% formic acid in water/35-95% acetonitrile).

Yield: 51 mg (31% of theory)

LC-MS (Method 1): $R_t$=1.36 min; MS (ESIpos): m/z=430 (M+H)$^+$ $^1$H NMR (400 MHz, DMSO-d$_6$): δ [ppm]=1.02 (t, 3H), 1.32-1.46 (m, 6H), 1.87 (sxt, 2H), 2.77 (t, 2H), 4.42 (s, 2H), 7.10-7.24 (m, 2H), 7.26-7.33 (m, 2H), 7.38 (t, 1H), 7.58 (t, 1H), 7.74 (d, 1H), 8.70 (d, 1H), 11.70 (br. s, 1H).

B. ASSESSMENT OF PHARMACOLOGICAL EFFICACY

The pharmacological action of the inventive compounds can be shown in the following assays:

B-1. Vasorelaxant Effect In Vitro

Rabbits are stunned by a blow to the neck and exsanguinated. The aorta is removed, freed from adhering tissue and divided into rings of width 1.5 mm, which are placed individually under prestress into 5 ml organ baths with carbogen-sparged Krebs-Henseleit solution at 37° C. having the following composition (each mM): sodium chloride: 119; potassium chloride: 4.8; calcium chloride dihydrate: 1; magnesium sulphate heptahydrate: 1.4; potassium dihydrogenphosphate: 1.2; sodium hydrogencarbonate: 25; glucose: 10. The contractile force is determined with Statham UC2 cells, amplified and digitalized using A/D transducers (DAS-1802 HC, Keithley Instruments Munich), and recorded in parallel on linear recorders.

To obtain a contraction, phenylephrine is added to the bath cumulatively in increasing concentration. After several control cycles, the substance to be studied is added in increasing dosage each time in every further run, and the magnitude of the contraction is compared with the magnitude of the contraction attained in the last preceding run. This is used to calculate the concentration needed to reduce the magnitude of the control value by 50% ($IC_{50}$ value). The standard administration volume is 5 μl; the DMSO content in the bath solution corresponds to 0.1%.

Representative $IC_{50}$ values for the inventive compounds are shown in the table below (table 1):

TABLE 1

| Example No. | $IC_{50}$ [nM] |
|---|---|
| 2 | 5160 |
| 5 | 22 |
| 8 | 95 |
| 9 | 641 |
| 11 | 601 |
| 15 | 78 |
| 16 | 340 |
| 17 | 292 |
| 18 | 1140 |
| 19 | 124 |
| 21 | 1130 |
| 22 | 7730 |
| 23 | 8060 |
| 26 | 794 |
| 27 | 1670 |
| 28 | 10 000 |

B-2. Effect on a Recombinant Guanylate Cyclase Reporter Cell Line

The cellular action of the inventive compounds is determined on a recombinant guanylate cyclase reporter cell line as described in F. Wunder et al., Anal. Biochem. 339, 104-112 (2005).

Representative values (MEC=minimal effective concentration) for the inventive compounds are shown in the table below (table 2):

TABLE 2

| Example No. | MEC [nM] |
|---|---|
| 2 | 65 |
| 3 | 300 |
| 5 | 30 |
| 6 | 766 |
| 8 | 300 |
| 9 | 100 |
| 10 | 1000 |
| 11 | 300 |
| 12 | 1000 |
| 15 | 100 |
| 16 | 300 |
| 17 | 300 |
| 18 | 300 |
| 19 | 100 |
| 21 | 100 |
| 22 | 1000 |
| 23 | 1000 |
| 24 | 100 |
| 25 | 300 |
| 26 | 300 |
| 27 | 300 |
| 28 | 1000 |

B-3. Radiotelemetric Measurement of Blood Pressure in Conscious, Spontaneously Hypertensive Rats A commercially available telemetry system from DATA SCIENCES INTERNATIONAL DSI, USA, is used for the blood pressure measurement on conscious rats described below.

The system consists of 3 main components:
- implantable transmitters (Physiotel® telemetry transmitter)
- receivers (Physiotel® receivers) which are connected via a multiplexer (DSI Data Exchange Matrix) to a
- data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963, were a cross of male Wistar Kyoto rats with greatly elevated blood pressure and female rats having slightly elevated blood pressure, and were handed over at F13 to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The TA11 PA-C40 telemetry transmitters used are surgically implanted under aseptic conditions in the experimental animals at least 14 days before the first experimental use. The animals instrumented in this way can be used repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and the wound is closed layer by layer.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is used as a control.

Test Procedure

The telemetry measuring unit present is configured for 24 animals. Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute values are corrected in the diagram with the currently measured barometric pressure (Ambient Pressure Reference Monitor; APR-1) and stored as individual data. Further technical details are given in the extensive documentation from the manufacturer company (DSI).

Unless stated otherwise, the test substances are administered at 9.00 am on the day of the experiment. Following the administration, the parameters described above are measured over 24 hours.

Evaluation

After the end of the experiment, the acquired individual data are sorted using the analysis software (Dataquest™ A.R.T.™ ANALYSIS). The blank value is assumed to be the time 2 hours before administration, and so the selected data set encompasses the period from 7.00 am on the day of the experiment to 9.00 am the following day.

The data are smoothed over an adjustable period by determination of the average (15-minute average) and transferred as a text file to a storage medium. The measured values presorted and compressed in this way are transferred to Excel templates and tabulated. For each day of the experiment, the data obtained are stored in a dedicated file bearing the experiment number. Results and test protocols are filed in order in paper form sorted by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-4. Determination of Pharmacokinetic Parameters Following Intravenous and Oral Administration:

The pharmacokinetic parameters of the inventive compounds are determined in male CD-1 mice, male Wistar rats and female beagles. Intravenous administration in the case of mice and rats is effected by means of a species-specific plasma/DMSO formulation, and in the case of dogs by means of a water/PEG400/ethanol formulation. In all species, oral administration of the dissolved substance is performed via gavage, based on a water/PEG400/ethanol formulation. The taking of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. When the blood is taken, it is passed into heparinized tubes. Then the blood plasma is obtained by centrifugation and is optionally stored at −20° C. until further processing.

An internal standard (which may also be a chemically unrelated substance) is added to the samples of the inventive compounds, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by means of LC-MS/MS using C18 reversed-phase columns and variable eluent mixtures. The substances are quantified via the peak heights or areas from extracted ion chromatograms of specific selected ion monitoring experiments.

The plasma concentration/time plots determined are used to calculate the pharmacokinetic parameters such as AUC, $C_{max}$, $t_{1/2}$ (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. After centrifugation at 1000 g, the plasma concentration is measured (by means of LC-MS/MS; see above) and determined by calculating the ratio of the $c_{blood}/c_{plasma}$ value.

B-5. Metabolic Study

To determine the metabolic profile of the inventive compounds, they are incubated with recombinant human cytochrome P450 (CYP) enzymes, liver microsomes or primary fresh hepatocytes from various animal species (e.g. rats, dogs), and also of human origin, in order to obtain and to compare information about substantially the complete phase I and phase II metabolism, and about the enzymes involved in the metabolism.

The inventive compounds were incubated with a concentration of about 0.1-10 μM. For this purpose, stock solutions of the inventive compounds having a concentration of 0.01-1 mM in acetonitrile were prepared, and then pipetted with 1:100 dilution into the incubation mixture. The liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration approx. 30%) and the protein was centrifuged off at approx. 15 000×g. The samples thus stopped were either analysed directly or stored at −20° C. until analysis.

The analysis is effected by means of high-performance liquid chromatography with ultraviolet and mass spectrometry detection (HPLC-UV-MS/MS). For this purpose, the supernatants of the incubation samples are chromatographed with suitable C18 reversed-phase columns and variable eluent mixtures of acetonitrile and 10 mM aqueous ammonium formate solution or 0.05% formic acid. The UV chromatograms in conjunction with mass spectrometry data serve for identification, structural elucidation and quantitative estimation of the metabolite, and for quantitative metabolic assessment of the inventive compound in the incubation mixtures.

B-6. Inhibition of Human Phosphodiesterase 5 (PDE 5)

PDE 5 preparations are obtained from human platelets by disruption (Microfluidizer®, 800 bar, 3 passes), followed by centrifugation (75 000 g, 60 min, 4° C.) and ion exchange chromatography of the supernatant on a Mono Q 10/10 column (linear sodium chloride gradient, elution with a 0.2-0.3M solution of sodium chloride in buffer (20 mM Hepes pH 7.2, 2 mM magnesium chloride). Fractions having PDE 5 activity are combined (PDE 5 preparation) and stored at −80° C.

To determine their in vitro action on human PDE 5, the test substances are dissolved in 100% DMSO and serially diluted. Typically, dilution series (1:3) from 200 µM to 0.091 µM are prepared (resulting final concentrations in the test: 4 µM to 0.0018 µM). In each case 2 µl of the diluted substance solutions are placed into the wells of microtitre plates (Isoplate-96/200 W; Perkin Elmer). Subsequently, 50 µl of a dilution of the above-described PDE 5 preparation are added. The dilution of the PDE 5 preparation is selected such that, during the later incubation, less than 70% of the substrate is converted (typical dilution: 1:100; dilution buffer: 50 mM tris/hydrochloric acid pH 7.5, 8.3 mM magnesium chloride, 1.7 mM EDTA, 0.2% BSA). The substrate, [8-$^3$H]cyclic guanosine-3',5'-monophosphate (1 µCi/µl; Perkin Elmer) is diluted 1:2000 with assay buffer (50 mM tris/hydrochloric acid pH 7.5, 8.3 mM magnesium chloride, 1.7 mM EDTA) to a concentration of 0.0005 µCi/µl. By addition of 50 µl (0.025 µCi) of the diluted substrate, the enzyme reaction is finally started. The test mixtures are incubated at room temperature for 60 min and the reaction is stopped by adding 25 µl of a suspension of 18 mg/ml yttrium scintillation proximity beads in water (phosphodiesterase beads for SPA assays, RPNQ 0150, Perkin Elmer). The microtitre plates are sealed with a film and left to stand at room temperature for 60 min Subsequently, the plates are analysed for 30 s per well in a Microbeta scintillation counter (Perkin Elmer). IC$_{50}$ values are determined using the graphic plot of the substance concentration against percentage PDE 5 inhibition.

Representative IC$_{50}$ values for the inventive compounds are reproduced in the table below (table 3):

TABLE 3

| Example No. | IC$_{50}$ [nM] |
| --- | --- |
| 2 | 3700 |
| 3 | 690 |
| 5 | 440 |
| 6 | 690 |
| 8 | 400 |
| 9 | 85 |
| 10 | 480 |
| 11 | 4000 |

TABLE 3-continued

| Example No. | IC$_{50}$ [nM] |
| --- | --- |
| 12 | 3500 |
| 15 | 310 |
| 16 | 64 |
| 17 | 230 |
| 18 | 16 |
| 19 | 370 |
| 21 | 75 |
| 22 | 530 |
| 23 | 440 |
| 24 | 25 |
| 25 | 160 |
| 26 | 95 |
| 27 | 340 |
| 28 | 450 |

B-7. Determination of Organ-Protective Effects in a Long-Term Experiment on Rats The organ-protective effects of the sGC stimulators were shown in a therapeutically relevant "low nitric oxide (NO)/high renin" hypertension model in rats. The study procedure was based on the recently published publication (Sharkovska Y, Kalk P, Lawrenz B, Godes M, Hoffmann L S, Wellkisch K, Geschka S, Relle K, Hocher B, Stasch J P. NO-independent stimulation of soluble guanylate cyclase reduces target organ damage in low- and high-renin models of hypertension. J. Hypertension. 2010; 28: 1666-1675). This involved treating renin-transgenic rats (TGR(mRen2)27) to which the NO synthase inhibitor L-NAME had been administered via drinking water simultaneously with an sGC stimulator or vehicle over several weeks. Haemodynamic and renal parameters were determined during the treatment period. At the end of the long-term study, organ protection (kidney, lung, heart, aorta) was shown by histopathological studies, biomarkers, expression analyses and cardiovascular plasma parameters.

C. WORKING EXAMPLES FOR PHARMACEUTICAL COMPOSITIONS

The inventive compounds can be converted to pharmaceutical formulations as follows:

Tablet:
Composition:

100 mg of the inventive compound, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm

Production:

The mixture of inventive compound, lactose and starch is granulated with a 5% solution (w/w) of the PVP in water. The granules are dried and mixed with the magnesium stearate for 5 minutes. This mixture is pressed with a conventional tableting press (for tablet format see above). The guide value used for the pressing is a pressing force of 15 kN.

Suspension for Oral Administration:
Composition:

1000 mg of the inventive compound, 1000 mg of ethanol (96%), 400 mg of Rhodigel® (xanthan gum from FMC, Pennsylvania, USA) and 99 g of water.

A single dose of 100 mg of the inventive compound corresponds to 10 ml of oral suspension.

Production:

The Rhodigel is suspended in ethanol; the inventive compound is added to the suspension. The water is added while stirring. The mixture is stirred for approx. 6 h until swelling of the Rhodigel has ended.

Solution for Oral Administration:
Composition:
500 mg of the inventive compound, 2.5 g of polysorbate and 97 g of polyethylene glycol 400. A single dose of 100 mg of the inventive compound corresponds to 20 g of oral solution.
Production:
The inventive compound is suspended in the mixture of polyethylene glycol and polysorbate while stirring. The stirring operation is continued until dissolution of the inventive compound is complete.
I.v. Solution:
The inventive compound is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound of formula (I)

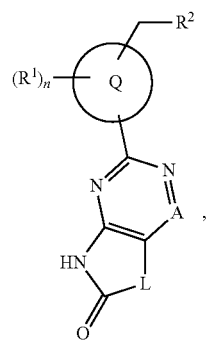

wherein
A is nitrogen or $CR^3$
where
$R^3$ is hydrogen, fluorine, difluoromethyl, trifluoromethyl, methyl, ethyl, cyclopropyl or cyclobutyl,
L is a #-$CR^{4A}R^{4B}$—$(CR^{5A}R^{5B})_m$-## group
where
\# is the attachment site to the carbonyl group,
\#\# is the attachment site to the pyrimidine or triazine ring,
m is a number 0,
$R^{4A}$ is hydrogen, fluorine, methyl, ethyl, hydroxyl or amino,
$R^{4B}$ is hydrogen, fluorine, difluoromethyl, trifluoromethyl, methyl, ethyl, cyclopropyl, cyclobutyl, cyclopentyl or a group of the formula -M-$R^6$,
in which methyl and ethyl may each be substituted by 1 to 3 substituents selected independently from the group of fluorine, cyano, trifluoromethyl, cyclopropyl, cyclobutyl, difluoromethoxy and trifluoromethoxy,
where $R^{4B}$ is hydrogen, difluoromethyl, trifluoromethyl, methyl, ethyl, cyclopropyl, cyclobutyl, cyclopentyl or a group of the formula -M-$R^6$ when $R^{4A}$ is hydroxyl,
and in which
M is a bond,
$R^6$ is —(C═O)$_r$—$NR^7R^8$, phenyl, thiazolyl, triazolyl, oxadiazolyl, thiadiazolyl or pyrimidinyl,
in which
r is the number 1,
$R^7$ and $R^8$ are each independently hydrogen, or cyclopropyl, and
in which phenyl, thiazolyl, triazolyl, oxadiazolyl, thiadiazolyl and pyrimidinyl may each in turn be substituted by 1 or 2 substituents selected independently from the group of fluorine, difluoromethyl, trifluoromethyl, methyl, ethyl, isopropyl, 2,2,2-trifluoroethyl, 1,1,2,2,2-pentafluoroethyl, cyclopropyl, cyclobutyl, cyclopropylmethyl and cyclobutylmethyl,
or
$R^{4A}$ and $R^{4B}$ together with the carbon atom to which they are bonded form a cyclopropyl, cyclobutyl, cyclopentyl, azetidinyl, tetrahydrofuranyl, pyrrolidinyl or tetrahydropyranyl ring,
in which the cyclopropyl, cyclobutyl, cyclopentyl, azetidinyl, tetrahydrofuranyl, pyrrolidinyl and tetrahydropyranyl ring may each be substituted by 1 or 2 substituents selected independently from the group of fluorine and methyl,
the ring Q is a group of the formula

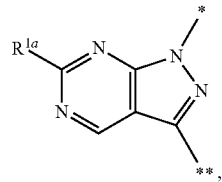
(a-1)

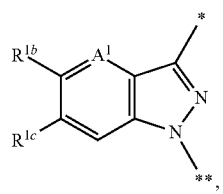
(b-1a)

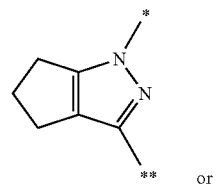
(1-1a)

or

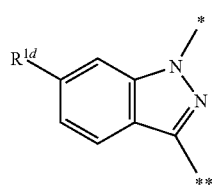
(1-1b)

where
\* is the attachment site to —$CH_2$—$R^2$,
\*\* is the attachment site to the pyrimidine or triazine ring,
$A^1$ is N or CH,
$R^{1a}$ is hydrogen or methyl,
$R^{1b}$ is hydrogen, fluorine or chlorine when $A^1$ is CH,
$R^{1b}$ is hydrogen when $A^1$ is N,
$R^{1c}$ is hydrogen or fluorine,
$R^{1d}$ is hydrogen or chlorine,
$R^2$ is 3,3,3-trifluoroprop-1-yl, 2,2,3,3-tetrafluoroprop-1-yl, pentafluoroprop-1-yl, phenyl or pyridyl, where phenyl is substituted by 1 to 3 fluorine substituents,
and
where pyridyl may be substituted by 1 fluorine substituent,
or a salt thereof.

2. The compound of claim 1, in which
A is nitrogen or $CR^3$
where
$R^3$ is hydrogen,
L is a #-$CR^{4A}R^{4B}$—$(CR^{5A}R^{5B})_m$-## group
where
# is the attachment site to the carbonyl group,
## is the attachment site to the pyrimidine or triazine ring,
m is a number 0,
$R^{4A}$ is hydrogen, fluorine, methyl or hydroxyl,
$R^{4B}$ is hydrogen, fluorine, trifluoromethyl, 2,2,2-trifluoroethyl or methyl, provided that $R^{4B}$ is not fluorine when $R^{4A}$ is hydroxyl,
the ring Q is a group of the formula

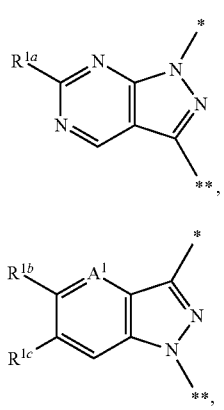

(a-1)

(b-1a)

(1-1a)

(1-1b)

where
* is the attachment site to —$CH_2$—$R^2$,
** is the attachment site to the pyrimidine or triazine ring,
$A^1$ is N or CH,
$R^{1a}$ is hydrogen or methyl,
$R^{1b}$ is hydrogen, fluorine or chlorine when $A^1$ is CH,
$R^{1b}$ is hydrogen when $A^1$ is N,
$R^{1c}$ is hydrogen or fluorine,
$R^{1d}$ is hydrogen or chlorine,
$R^2$ is 3,3,3-trifluoroprop-1-yl, 2,2,3,3,3-pentafluoroprop-1-yl, phenyl or pyridyl, where phenyl is substituted by 1 to 3 fluorine substituents,
and
where pyridyl may be substituted by 1 fluorine substituent,
or a salt thereof.

3. The compound of claim 1, in which
A is nitrogen or $CR^3$
where
$R^3$ is hydrogen,
L is a #-$CR^{4A}R^{4B}$—$(CR^{5A}R^{5B})_m$-## group
where
# is the attachment site to the carbonyl group,
## is the attachment site to the pyrimidine or triazine ring,
m is a number 0,
$R^{4A}$ is methyl,
$R^{4B}$ is methyl,
the ring Q is a group of the formula

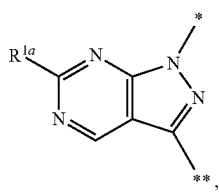

(a-1)

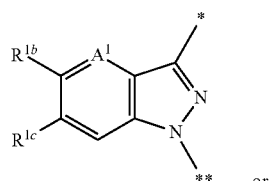

(b-1)

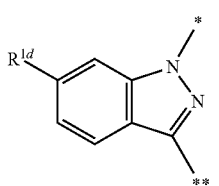

or (1-1b)

where
* is the attachment site to —$CH_2$—$R^2$,
** is the attachment site to the pyrimidine or triazine ring,
$A^1$ is N or CH,
$R^{1a}$ is hydrogen or methyl,
$R^{1b}$ is hydrogen, fluorine or chlorine when $A^1$ is CH,
$R^{1b}$ is hydrogen when $A^1$ is N,
$R^{1c}$ is hydrogen or fluorine,
$R^{1d}$ is chlorine,
$R^2$ is 2,2,3,3,3-pentafluoroprop-1-yl, phenyl or pyridyl,
where phenyl is substituted by 1 or 2 fluorine substituents,
and
where pyridyl may be substituted by 1 fluorine substituent,
or a salt thereof.

4. The compound of claim 1, in which
A is nitrogen,
L is a #-$CR^{4A}R^{4B}$—$(CR^{5A}R^{5B})_m$-## group
where
# is the attachment site to the carbonyl group,
## is the attachment site to the triazine ring, m is a number 0,
$R^{4A}$ is methyl,
$R^{4B}$ is methyl,
the ring Q is a group of the formula

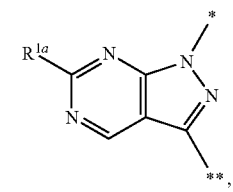
(a-1)

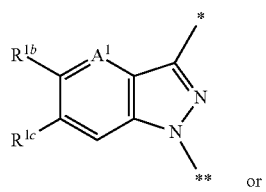
(b-1)

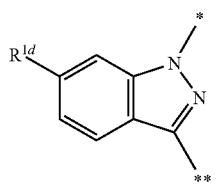
(1-1b)

where
* is the attachment site to —CH$_2$—R$^2$,
** is the attachment site to the triazine ring,
A$^1$ is N or CH,
R$^{1a}$ is hydrogen or methyl,
R$^{1b}$ is hydrogen, fluorine or chlorine when A$^1$ is CH,
R$^{1b}$ is hydrogen when A$^1$ is N,
R$^{1c}$ is hydrogen or fluorine,
R$^{1d}$ is hydrogen or chlorine,
R$^2$ is phenyl,
  where phenyl is substituted by 1 or 2 fluorine substituents,
or a salt thereof.

5. The compound of claim 1, selected from the group consisting of:

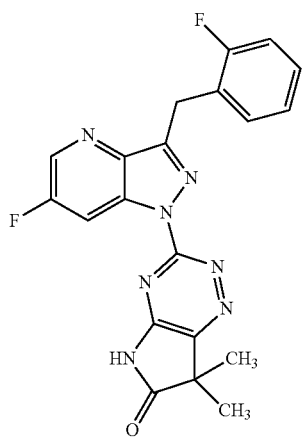
,

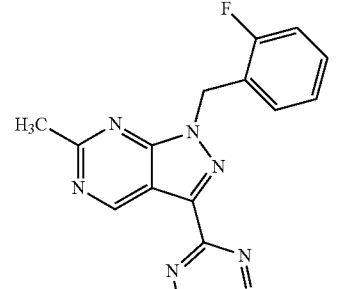
,

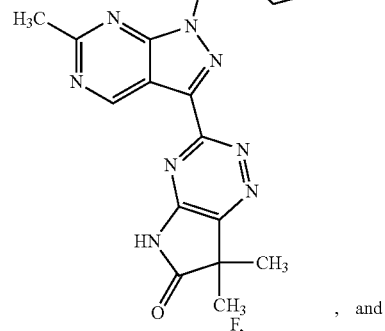
,

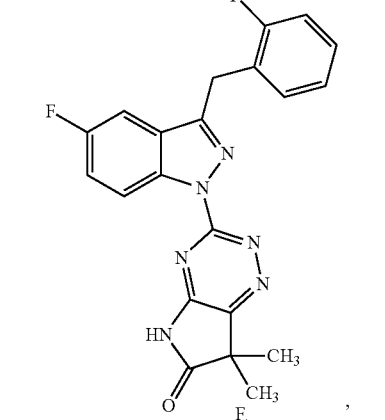
, and

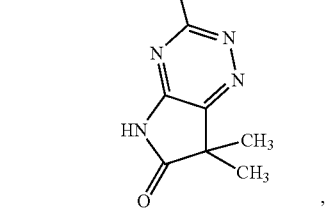
, or a salt thereof.

6. A process for preparing the compound of claim 1, comprising

[A] reacting a compound of formula (II)

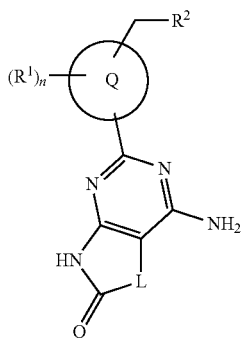

(II)

in which n, L, Q, 1e and $R^2$ are each as defined in claim 1 isopentyl nitrite, thereby producing a compound of formula (I-A)

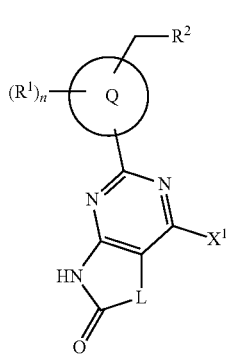

(I-A)

in which n, L, Q, 1e and $R^2$ are each as defined in claim 1, and $X^1$ is bromine or iodine, or

[B] reacting a compound of the formula (I-A) in an inert solvent in the presence of a suitable transition metal catalyst to give a compound of formula (I-B)

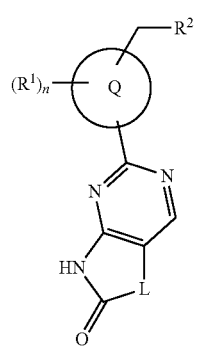

(I-B)

in which n, L, Q, 1e and $R^2$ are each as defined in claim 1, or

[C] reacting a compound of formula (I-A) in an inert solvent in the presence of a suitable transition metal catalyst with a compound of the formula (III-A), (III-B) or (III-C)

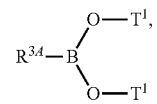

(III-A)

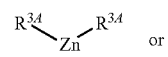

(III-B)

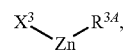

(III-C)

$$X^3\underset{Zn}{\diagup}R^{3A},$$

(III-D)

in which $R^{3A}$ is halogen, difluoromethyl, trifluoromethyl, ($C_1$-$C_4$)-alkyl, ($C_2$-$C_4$)-alkenyl, ($C_2$-$C_4$)-alkynyl, cyclopropyl, cyclobutyl, phenyl or 5- or 6-membered heteroaryl, in which ($C_1$-$C_4$)-alkyl, ($C_2$-$C_4$)-alkenyl, ($C_2$-$C_4$)-alkynyl, phenyl and 5- or 6-membered heteroaryl may each be substituted by 1 to 3 substituents selected independently from the group comprising fluorine, difluoromethyl, trifluoromethyl, ($C_1$-$C_4$)-alkyl, difluoromethoxy, trifluoromethoxy, ($C_1$-$C_4$)-alkoxy, ($C_1$-$C_4$)-alkoxycarbonyl, cyclopropyl and cyclobutyl, $T^1$ is hydrogen or ($C_1$-$C_4$)-alkyl, or both $R^{11}$ radicals together form a —$C(CH_3)_2$—$C(CH_3)_2$— bridge, and $X^3$ is bromine or iodine, to give a compound of the formula (I-C)

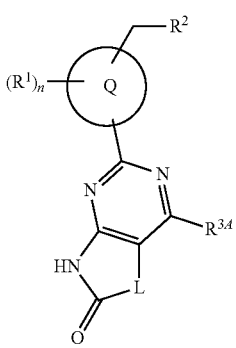

(I-C)

in which n, L, Q, 1e, $R^2$ and $R^{3A}$ are each as defined above, or

[D] reacting the compound of formula (IA) in an inert solvent in the presence of a suitable base with hydrazine hydrate to give a compound of the formula (IV)

(IV)

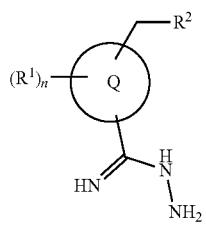

in which n, L, Q, 1e and R² are each as defined in claim 1,
reacting the compound of formula (IV) in an inert solvent with a compound of the formula (V)

(V)

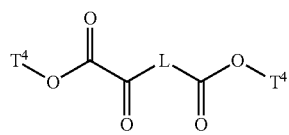

in which L is as defined in claim 1 and
T⁴ is $(C_1$-$C_4)$-alkyl
to give a compound of the formula (VI)

(VI)

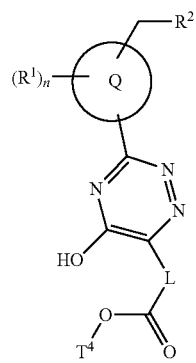

in which n, L, Q, R¹, R² and T⁴ are each as defined above,
converting the compound of formula (VI) using phosphoryl chloride into a compound of the formula (VII)

(VII)

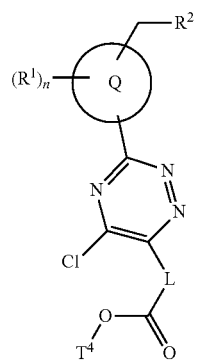

in which n, L, Q, R¹, R² and T⁴ are each as defined above, and reacting the compound of formula (VII) with ammonia to give a compound of the formula (VIII)

(VIII)

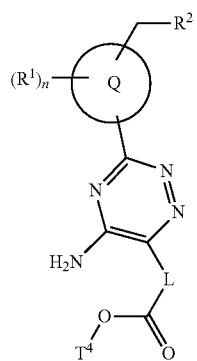

in which n, L, Q, 1e, R² and T⁴ are each as defined above,
and cyclizing the compound of formula (VIII) in an inert solvent, optionally in the presence of a suitable base, to give a compound of the formula (I-D)

(I-D)

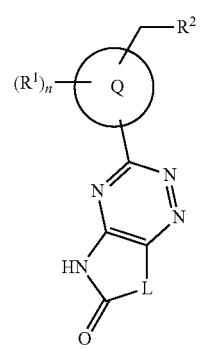

in which n, L, Q, 1e and R² are each as defined in claim 1,
or
[E] reacting a compound of the formula (X)

(X)

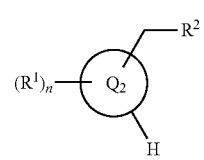

in which n, R¹ and R² are each as defined in claim 1 and the ring Q² is a group of the formula (a-1)

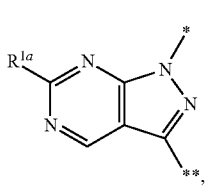

-continued

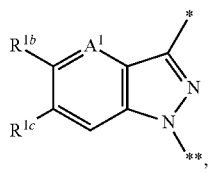
(b-1a)

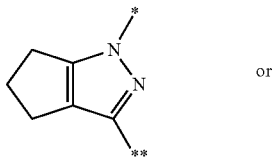
(1-1a)

or

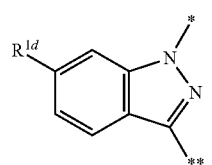
(1-1b)

where
* is the attachment site to —CH$_2$—R$^2$,
** is the attachment site to the hydrogen atom, and
A$^1$, R$^{1a}$, R$^{1b}$, R$^{1c}$, and R$^{1d}$ are each defined in claim 1;
in an inert solvent, optionally in the presence of a suitable base, with a compound of the formula (XI)

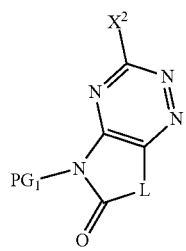
(XI)

in which L is as defined in claim 1,
X$^2$ is chlorine or bromine and
PG$^1$ is a suitable amino protecting group, especially p-methoxybenzyl, to give a compound of the formula (XII)

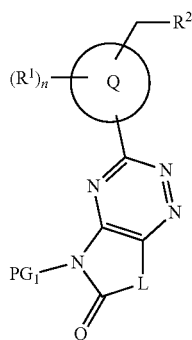
(XII)

in which n, L, Q$_2$, R$^1$, R$^2$ and PG$^1$ are each as defined above,
the protecting group PG$^1$ is subsequently detached therefrom to give a compound of the formula (I-E)

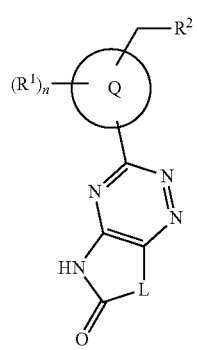
(I-E)

in which n, L, Q$_2$, R$^1$ and R$^2$ are each as defined above,
and, optionally, reacting a compound of formula (I-A), (I-B), (I-C), (I-D) or (I-E) with the appropriate (i) solvent and/or (ii) acid or bases to produce a salt thereof.

7. A pharmaceutical composition, comprising a compound claim 1 and an inert, nontoxic, pharmaceutically suitable excipient.

* * * * *